United States Patent
Liu et al.

(10) Patent No.: US 11,680,293 B1
(45) Date of Patent: Jun. 20, 2023

(54) METHODS AND COMPOSITIONS FOR AMPLIFYING DNA AND GENERATING DNA SEQUENCING RESULTS FROM TARGET-ENRICHED DNA MOLECULES

(71) Applicant: Paragon Genomics, Inc., Fremont, CA (US)

(72) Inventors: Zhitong Liu, Foster City, CA (US);
David Debruyne, Hayward, CA (US);
Jack Dong, San Ramon, CA (US);
Michael Clark, Pleasanton, CA (US);
Yutao Fu, San Marcos, CA (US);
Chenyu Li, Hayward, CA (US);
Vidushi Kapoor, Fremont, CA (US);
Kalyani Patankar, Wheeling, IL (US)

(73) Assignee: Paragon Genomics, Inc., Fremont, CA (US)

( * ) Notice: Subject to any disclaimer, the term of this patent is extended or adjusted under 35 U.S.C. 154(b) by 0 days.

(21) Appl. No.: 17/726,480

(22) Filed: Apr. 21, 2022

(51) Int. Cl.
*C12Q 1/6874* (2018.01)
*C12N 15/10* (2006.01)
*C12Q 1/6806* (2018.01)
*C12Q 1/6855* (2018.01)

(52) U.S. Cl.
CPC ....... *C12Q 1/6874* (2013.01); *C12N 15/1065* (2013.01); *C12Q 1/6806* (2013.01); *C12Q 1/6855* (2013.01)

(58) Field of Classification Search
CPC .............. C12Q 1/6874; C12Q 1/6806; C12Q 1/6855; C12Q 1/6869; C12Q 2525/191; C12Q 2563/179; C12N 15/1065
See application file for complete search history.

(56) References Cited

U.S. PATENT DOCUMENTS

| | | | |
|---|---|---|---|
| 4,683,195 A | 7/1987 | Mullis et al. | |
| 4,683,202 A | 7/1987 | Mullis | |
| 4,965,188 A | 10/1990 | Mullis et al. | |
| 5,168,038 A | 12/1992 | Tecott et al. | |
| 5,210,015 A | 5/1993 | Gelfand et al. | |
| 5,399,491 A | 3/1995 | Kacian et al. | |
| 5,539,082 A | 7/1996 | Nielsen et al. | |
| 5,750,341 A | 5/1998 | Macevicz | |
| 5,854,033 A | 12/1998 | Lizardi | |
| 5,925,517 A | 7/1999 | Tyagi et al. | |
| 6,174,670 B1 | 1/2001 | Wittwer et al. | |
| 6,670,461 B1 | 12/2003 | Wengel et al. | |
| 8,586,310 B2 | 11/2013 | Mitra et al. | |
| 8,673,560 B2 | 3/2014 | Leamon et al. | |
| 8,685,678 B2 | 4/2014 | Casbon et al. | |
| 9,464,318 B2 | 10/2016 | Liu | |
| 9,556,427 B2 | 1/2017 | Ji | |
| 9,752,188 B2 | 9/2017 | Schmitt et al. | |
| 10,100,358 B2 | 10/2018 | Liu et al. | |
| 10,421,993 B2 | 9/2019 | Liu et al. | |
| 10,941,453 B1 | 3/2021 | Liu et al. | |
| 11,479,807 B2 * | 10/2022 | Kennedy | C12Q 1/6806 |
| 2004/0185484 A1 | 9/2004 | Costa et al. | |
| 2006/0234264 A1 | 10/2006 | Hardenbol | |
| 2008/0014634 A1 | 1/2008 | Greener et al. | |
| 2009/0123913 A1 | 5/2009 | Barany et al. | |
| 2009/0203085 A1 | 8/2009 | Kum | |
| 2013/0261027 A1 | 10/2013 | Li et al. | |
| 2014/0227705 A1 | 8/2014 | Vogelstein et al. | |
| 2014/0322716 A1 | 10/2014 | Robins | |
| 2014/0329245 A1 | 11/2014 | Spier et al. | |
| 2014/0357500 A1 | 12/2014 | Vigneault et al. | |
| 2014/0378317 A1 | 12/2014 | Fu et al. | |
| 2015/0087027 A1 | 3/2015 | Makarov et al. | |
| 2016/0024493 A1 | 1/2016 | Robins | |
| 2016/0053253 A1 | 2/2016 | Salathia et al. | |
| 2016/0122753 A1 | 5/2016 | Mikkelsen et al. | |
| 2016/0312276 A1 | 10/2016 | Fu et al. | |
| 2017/0114406 A1 | 4/2017 | Hansen et al. | |
| 2017/0226498 A1 | 8/2017 | Zheng et al. | |
| 2018/0010176 A1 | 1/2018 | Patel | |
| 2018/0030515 A1 | 2/2018 | Regev et al. | |
| 2018/0163201 A1 | 6/2018 | Larson | |
| 2019/0010489 A1 | 1/2019 | Chang et al. | |

(Continued)

FOREIGN PATENT DOCUMENTS

| | | |
|---|---|---|
| CN | 101575597 A | 11/2009 |
| JP | H04262799 A | 9/1992 |

(Continued)

OTHER PUBLICATIONS

Aboul-Maaty et al.; Extraction of high-quality genomic DNA from different plant orders applying a modified CTAB-based method; Bulletin of the National Research Centre; 43(1): 10 pages, doi 10.1186/S42269-019-0066-1; Dec. 2019.

Allawi et al.; Thermodynamics and NMR of internal GO T mismatches in DNA; Biochemistry; 36(340; pp. 10581-10594; Aug. 1997.

Altschul et al.; Gapped blast and psi-blast: a new generation of protein database search programs; Nucleic Acids Research: 25(17); pp. 3389-3402; Sep. 1997.

Anderson et al.; Protocol; a versatile, inexpensive, high-throughput plant genomic DNA extraction method suitable for genotyping-by-sequencing: Plant Methods; 14(1); 10 pages, doi.org/10.1186/s13007-018-0336-1; Dec. 2018.

(Continued)

*Primary Examiner* — David C Thomas
(74) *Attorney, Agent, or Firm* — Shay Glenn LLP

(57) ABSTRACT

Methods, apparatuses and compositions for generating highly sensitive and accurate sequencing results of massive parallel sequencing (NGS). The methods and compositions may be referred to as SubDivision-Seq, and may comprise two parts. The first part includes making a target-enriched DNA library, organizing the UMIs on DNA molecules to form primary clones and subdividing the primary clones into subclones. The second part includes sequencing the DNA library by NGS, deducing consensus sequence from each subclone, then deducing consensus sequence in each primary clone.

24 Claims, 19 Drawing Sheets

Specification includes a Sequence Listing.

(56) References Cited

U.S. PATENT DOCUMENTS

| | | | |
|---|---|---|---|
| 2019/0112648 | A1 | 4/2019 | Schaal et al. |
| 2020/0109437 | A1 | 4/2020 | Chang et al. |
| 2020/0156071 | A1 | 5/2020 | Hansen et al. |
| 2020/0208143 | A1 | 7/2020 | Liu et al. |
| 2020/0256861 | A1 | 8/2020 | Johnston et al. |
| 2021/0180051 | A1 | 6/2021 | Liu et al. |
| 2021/0277461 | A1* | 9/2021 | Glezer ................. C12Q 1/6855 |
| 2021/0363517 | A1 | 11/2021 | Liu et al. |
| 2022/0220543 | A1* | 7/2022 | Salk ..................... C12Q 1/6869 |

FOREIGN PATENT DOCUMENTS

| | | | |
|---|---|---|---|
| WO | WO2005/095605 | A1 | 10/2005 |
| WO | WO2006/127423 | A2 | 11/2006 |
| WO | WO2006/138444 | A2 | 12/2006 |
| WO | WO2008/061193 | A2 | 5/2008 |
| WO | WO2012/149438 | A1 | 11/2012 |
| WO | WO2015/063154 | A1 | 5/2015 |
| WO | WO2016/040901 | A1 | 3/2016 |
| WO | WO2016/170147 | A1 | 10/2016 |

OTHER PUBLICATIONS

Babon et al.: The use of resolvases T4 endonuclease VII and T7 endonuclease I in mutation detection; in Methods in Molecular Biology; vol. 152: DNA Repair Protocols: Prokaryotic systems; Edited by R. Vaughan; © Humana Press Inc.; Totowa, NJ; pp. 187-199; Jul. 2000.

Bernard et al.; Color multiplexing hybridization probes using the apolipoprotein E locus as a model system for genotyping; Anal. Biochem.; 273(2); pp. 221-228; Sep. 10, 1999.

Casbon et al.; A method for counting PCR template molecules with application to next-generation sequencing; Nucleic Acids Res.; 39(12); 8 pages; e81.doi: 10.1093/nar/gkr217; Jul. 2011.

Chen et al.; Generation and analysis of a barcode-tagged insertion mutant library in the fission yeast Schizosaccharomyces pombe: BMC Genomics; 13(1); 18 pages; retrieved from the internet (http://www.biomedcentral.com/1471-2164/13/161; Dec. 2012.

Crooke et al.; Section review biologicais and immunologicals: Progress in the development and patenting of antisense drug discovery technology; Expert Opinion on Therapeutic Patents; 6(9); pp. 855-870; Sep. 1, 1996.

Fu et al.; Counting individual DNA molecules by the stochastic attachment of diverse labels; Proc. Natl. Acad. Sci. USA; 108(22); pp. 9026-9031; May 31, 2011.

Fuhrmann et al.; Removal of mismatched bases from synthetic genes by enzymatic mismatch cleavage; Nucleic Acids Research; 33(6); 8 pages; doi:10.1093/nar/gni058; Jan. 2005.

Gregory et al.; Targeted single molecule mutation detection with massively parallel sequencing; Nucleic Acids Res.; 44(3); 11 pages; e22. doi:10.1093/nar/gkv915; Feb. 18, 2016.

Hill-Ambroz et al.; Modified rapid DNA extraction protocol for high throughput microsatellite analysis in wheat; Crop Science; 42(6); pp. 2088-2091; 4 pages, doi: 10.2135/cropsci2002.2088; Nov. 2002.

Hoffmann et al.; DNA bar coding and pyrosequencing to identify rare HIV drug resistance mutations; Nucleic Acids Res.; 35(13); 8pages; e91, doi:10.1093/nar/gkm435; ; Jun. 18, 2007.

Illumnia; Nextera XT Library Prep: Tips and Troubleshooting; retrieved from the internet (https://www.iliumina.com/content/dam/illumina-marketing/documents/products/technotes/nextera-xt-troubleshooting-technical-note.pdf); 6 pages;on May 5, 2021.

Illumina; RNA sequencing methods; 122 pages; retrieved from the internet (https://www.iliumina.com/content/dam/iilumina-marketing/documents/products/research_reviews/rna-sequencing-methods-review-web.pdf) on Mar. 23, 2022.

Juvonen et al.; Amplification Facilitators and Pre-Processing Methods for PCR Detection of Strictly Anaerobic Beer-Spoilage Bacteria of the Class Clostridia in Brewery Samples; Journal of the Institute of Brewing and Distilling; 115(3); pp. 167-176; Aug. 1, 2009.

Kanehisa ; Use of statistical criteria for screening potential homologies in nucleic acid sequences; Nucleic Acids Res.; 12(1 prt 1); pp. 203-213; Jan. 11, 1984.

Kasajima; Successful tips of DNA extraction and PCR of plants for beginners; Trends in Research; 1(3): 1-2, 5 pages: doi:10.15761/TR.1000115; Sep. 2018.

Kivioja et al.; Counting absolute numbers of molecules using unique molecular identifiers; Nat. Methods; 9(1); pp. 72-74; (Author Manuscript); Nov. 20, 2011.

Leone et al; Molecular beacon probes combined with amplification by NASBA enable homogeneous, real-time detection of RNA; Nucleic Acids Res.; 26(9); pp. 2150-2155; May 1, 1998.

Li et al.; A universal method for direct PCR amplification of plant tissues; Analytical Methods; 9(11); pp. 1800-1805; 6 pages, doi: 10.1039/C6AY03156K; (the year of publication is sufficiently earlier than the effective U.S. filing date and any foreign priority date so that the particular month of publication is not in issue) 2017.

Lowell et al.; Heteroduplex resolution using T7 endonuclease I in microbial community analyses; Bio Techniques; 28(4); pp. 676-681; Apr. 2000.

Mackay et al.: Real-time PCR in virology: Nucleic Acids Research; 30(6); pp. 1292-1305; Mar. 15, 2002.

Mardis; The impact of next-generation sequencing technology on genetics; Treand In Genetics; 24(3); pp. 133-141; Mar. 1, 2008.

Mcdonough et al.; Use of FFPE-derived DNA in next generation sequencing: DNA extraction methods; Plos one; 14(4); 15 pages; doi: 10.1371/journal.pone.0211400; April 2019.

Mesmaeker et al.; Backbone modifications in oligonucleotides and peptide nucleic acid systems; Current Opinion in Structural Biology; 5(3); pp. 343-355; Jun. 1995.

Needleman et al.; A general method applicable to the search for similarities in the amino acid sequence of two proteins; Journal of Molecular Biology; 48(3); pp. 443-453; May 1970.

Newman et al.; Integrated digital error suppression for imptoved detection of circulating tumor DNA; Nature Biotechnology; 34(5); pp. 547-555, doi: 10.1038/nbt.3520; (Author Manuscript); May 2016.

Phallen et al.; Direct detection of early-stage cancers using circulating tumor DNA; Sci. Transl. Med.; 9(403); pii: eaan2415. doi: 10.1126/scritranslmed.aan2415; Aug. 16, 2017.

Qiu et al.; Evaluation of PCR-generated chimeras, mutations, and heteroduplexes with 16S rRNA gene-based cloning. Applied and Environmental Microbiology. 67(2): pp. 880-887; Feb. 1, 2001.

Rana et al.; Optimized nuclear pellet method for extracting next-generation sequencing quality genomic DNA from fresh leaf tissue; Methods and protocols; 2(2):54; 11 pages, doi: 10.3390/mps2020054; ; June 2019.

Schmitt et al.; Detection of ultra-rare mutations by next-generation sequencing; Proc. Natl. Acad. Sci. USA; 109(36); pp. 14508-14513; Sep. 4, 2012.

Shendure et al.; Next-generation DNA sequencing; Nature Biotechnology; 26(10); pp. 1135-1145; Oct. 2008.

Smith et al.; Comparison of biosequences; Advances in Applied Mathematics; 2(4); pp. 482-489; Dec. 1981.

Stahlberg et al.; Simple, multiplexed, PCR-based barcoding of DNA enables sensitive mutation detection in liquid biopsies using sequencing; Nucleic Acids Res.; 44(11); pp. 1-7; e105. doi: 10.1093/nar/gkw224; June 20, 2016.

Stoler et al.; Streamlined analysis of duplex sequencing data with du novo; Genome Biology; 17(1); 10 pages; DOI 10.1186/s13059-016-1039-4; Dec. 2016.

Su et al.; Next-generation sequencing and its applications in molecular diagnostics; Expert Rev. Mol. Diagn.; 11(3); pp. 333-343; Apr. 2011.

Takishita et al.; Genetic diversity of microbial eukaryotes in anoxic sediment of the saline meromictic lake namako-ike (japan): on the detection of anaerobic or anoxic-tolerant lineages of eukaryotes; Protist: 158(1); pp. 51-64; Jan. 2007.

Tan et al.; DNA, RNA, and protein extraction: the past and the present: Journal of Biomedicine and Biotechnology; Hindawi Publishing Corporation; 10 pages, doi:10.1155/2009/574398; Nov. 2009.

(56) References Cited

OTHER PUBLICATIONS

Uhlman et al.; Antisense oligonucleotides: a new therapeutic principle; Chemical Reviews; 90(4); pp. 543-584; Jun. 1, 1990.

Von Post et al.; A high-throughput DNA extraction method for barley seed; Euphytica; 130(2); pp. 255-260; 6 pages, doi 10.1023/A:1022863006134; Mar. 2003.

Wang et al.; A rapid and cheap protocol for preparation of PCR templates in peanut: Electronic Journal of Biotechnology; 12(2); pp. 9-10; 7 pages, doi 10.2225/vol12-issue2-fulltext-11; Apr. 2009.

Wang et al.; A simple method of preparing plant samples for PCR; Nucleic Acids Research; 21(17); pp. 4153-4154; Aug. 1993.

Wang et al.; Targeted sequencing of both DNA strands barcoded and captured individually by RNA probes to identify genome-wide ultra-rare mutations; Scientific Reports: 7(1); 14 pages; 3356 DOI:10.1038/s41598-017-03448-8; Jun. 13, 2017.

Wang et al.; Use of template switching oligos (TS oligos, TSOs) for efficient cDNA library construction; 4 pages, retrieved from the internet (https://www.idtdna.com/pages/education/decoded/article/use-of-template-switching-oligos-(ts-oligos-tsos)-for-efficient-cdna-library-construction) on Mar. 23, 2022.

Werner et al.; Direct amplification and NaOH extraction: two rapid and simple methods for preparing bryophyte DNA for polymerase chain reaction (PCR); Journal of Bryology; 24(2); pp. 127-131; 5 pages, doi: 10.1179/037366802125000980; Jun. 2002.

Young et al.; Efficient isolation of genes by using antibody probes; Proc. Natl. Acad. Sci.USA; 80(5); pp. 1194-1198; Mar. 1983.

Zhang et al.; Elimination of primer-dimer effect in SYBR green I real-time RT-PCR using 4-step program. Chinese Journal of Biochemistry and Molecular Biology; 2004; 20(3); pp. 387-392; (Machine Translated English Abstract); Dec. 31, 2003.

Zhang et al.; The impact of next-generation sequencing on genomics; J. Genet. Genomics; 38(3); pp. 95-109; (Author Manuscript) Mar. 20, 2011.

Lin et al.; A convenient method to remove primer dimer in polymerase chain reaction; Journal of Xinxiang Medical College; 29(6); pp. 617-418, 421; (Machine Translated English Abstract); Jun. 5, 2012.

Liu et al.; U.S. Appl. No. 16/741,272 entitled "Methods and compositions for preparation of crude lysate of nucleic acids," filed Jan. 13, 2020.

Illumina; An introduction to next-generation sequencing technology; Illumina Inc; 2015; retrieved from the internet (https://www/illumina.com/content/dam/illumina-marketing/documents/products/illumina_sequencing_introduction.pdf) on Nov. 1, 2022.

Kohn et al.; Single-Cell Semiconductor Sequencing; Methods in Molecular Biology; Chapter 18; 148; pp. 247-284, 2017.

* cited by examiner

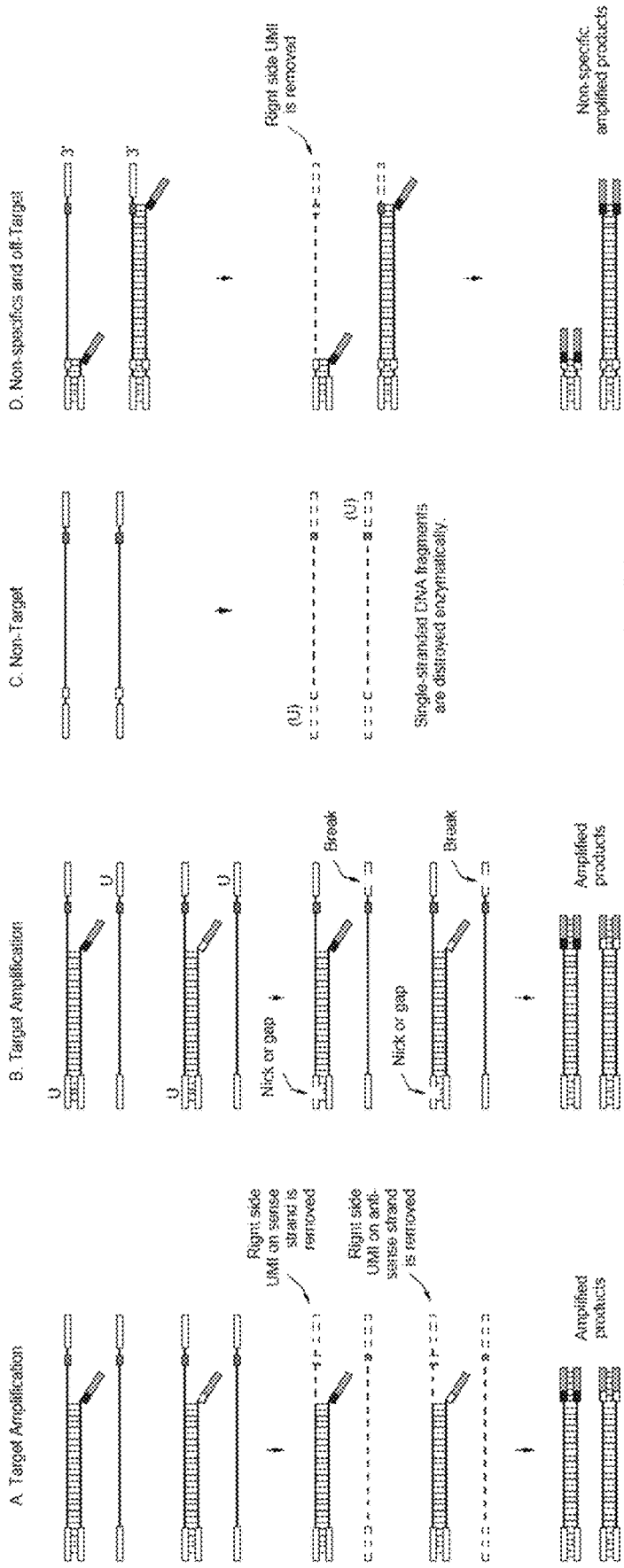

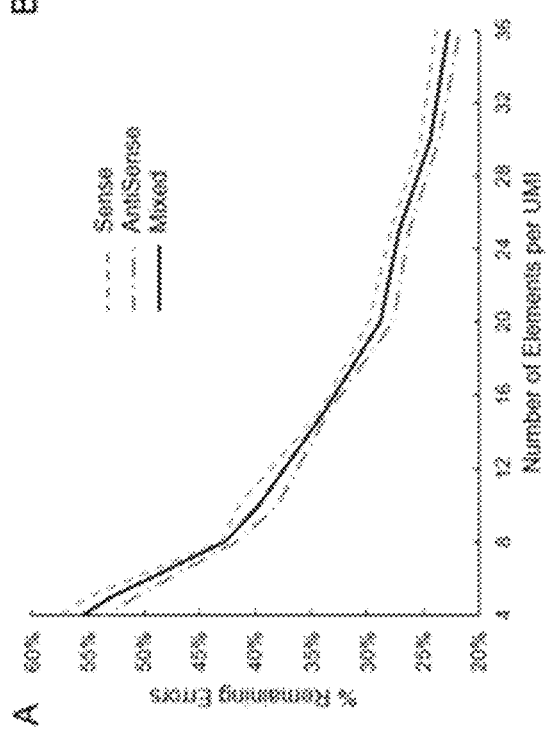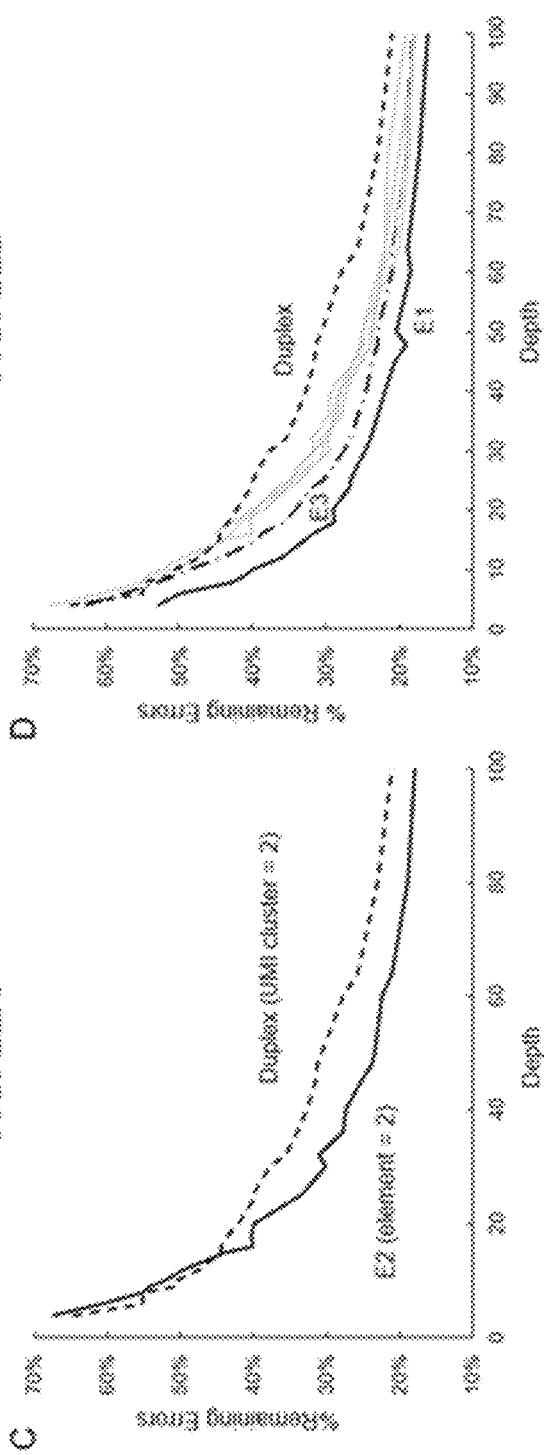
FIG. 12A
FIG. 12B
FIG. 12C
FIG. 12D

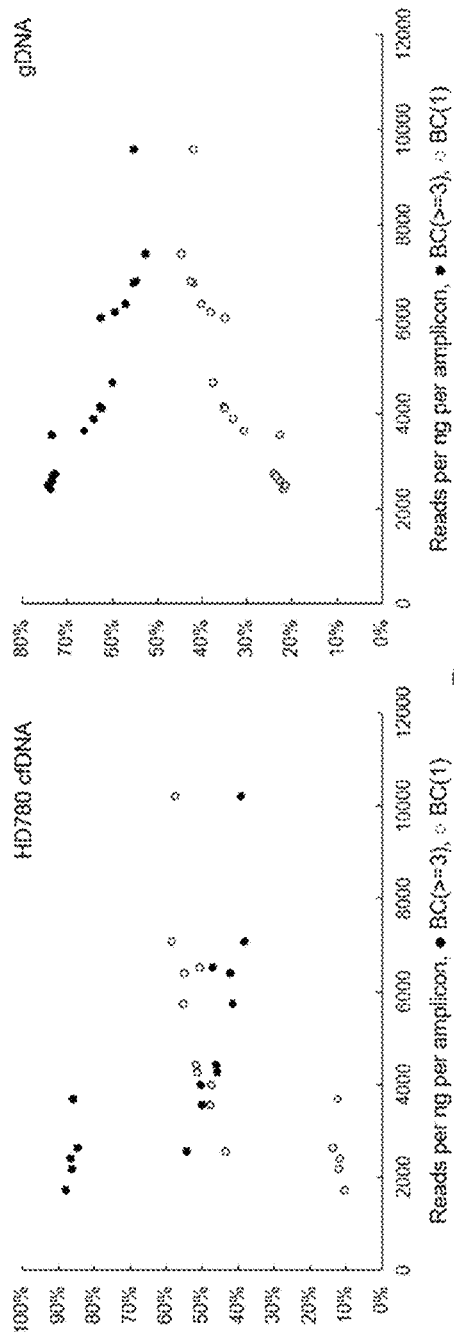
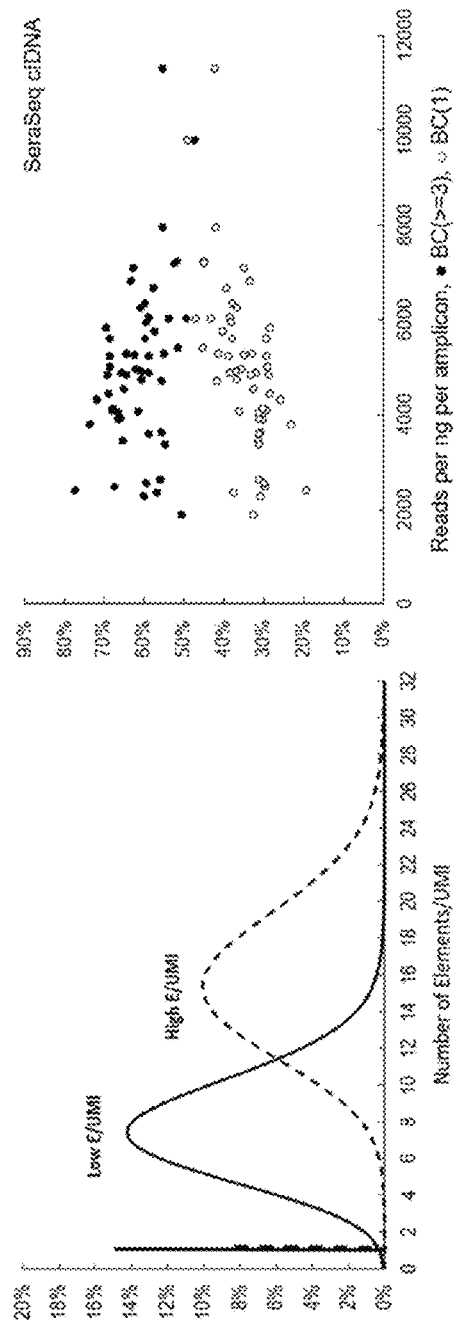
FIG. 15A
FIG. 15B
FIG. 15C
FIG. 15D

Codes for finding consensus sequence.
```
function [reSult, ConS] = consensusdata(M, Templ,
ClusterSize, Grp)
% inputs are (1) M = matrix of digitized sequences, (2) Templ
= ref sequence
% (3) ClusterSize = number of elements per group, (4) Grp =
number of groups
% outputs are (1) reSult = % number of correct bases, (2)
Cons = consensus sequences
%
% Example 1, first dimension consensus:
% M= paste; Templ = paste;
% ClusterSize = 2;
% Grp = 100; (Note 2X100=Rows of M)
% [reSult, ConS] = consensusdata(M, Templ, ClusterSize, Grp);
% copy(reSult);
% copy(ConS);
%

M1 = [1;2;3;4];
A = size(M,1);

% ClusterSize = 2;
% Grp = 1;

InterConS = zeros(4*A(1,1)/ClusterSize, 150);
ConS = zeros(A/ClusterSize, 150);

%genearte consensus sequence matrix
y = 1;
z = 1;
for g = 1:Grp
    InterConS(y:g*4, :) = histc(M(z:g*ClusterSize, :),M1);
    y = y + 4;
    z = z + ClusterSize;
end checkMax = zeros(Grp, 150);
InterMax = zeros(4*A(1,1)/ClusterSize, 150);
interconSenS = zeros(Grp, 150);
```

FIG. 16A

```
i = 1;
for g = 1:Grp
    for j = 1:150
        if InterConS(i, j) == max(InterConS(i:g*4, j))
            InterMax(i, j) = 1;
        else
            InterMax(i, j) = 0;
        end
        if InterConS(i+1, j) == max(InterConS(i:g*4, j))
            InterMax(i+1, j) = 2;
        else
            InterMax(i+1, j) = 0;
        end
        if InterConS(i+2, j) == max(InterConS(i:g*4, j))
            InterMax(i+2, j) = 3;
        else
            InterMax(i+2, j) = 0;
        end
        if InterConS(i+3, j) == max(InterConS(i:g*4, j))
            InterMax(i+3, j) = 4;
        else
            InterMax(i+3, j) = 0;
        end
    end
    i = i + 4;
end z = 1;
for g = 1:Grp
    checkMax(g, :) = histc(InterMax(z:g*4, :),0);
    z = z +4;
end z = 1;
for g = 1:Grp
    interconSenS(g, :) = sum(InterMax(z:g*4, :));
    z = z +4;
end
```

FIG. 16B

```
% find consensus seq without 2 bases are equally in max
for n = 1:Grp
    for m = 1:150
        if checkMax(n, m) == 3
            ConS(n, m) = interconSenS(n, m);
        else
            ConS(n, m) = 0;
        end
    end
end % ConS is the final consensus sequence, it is zero if 2 bases
are equally max.

% count the percentage of (1) correct bases and (2) errors
interResult = zeros(Grp,150);
reSult = zeros(Grp,1);
for n = 1:Grp
    for m = 1:150
        if ConS(n, m) == Templ(1,m)
            interResult(n, m) = 1;
        else
            interResult(n, m) = 0;
        end
    end
end reSult(:,1) = sum(interResult, 2)/150;

% reSult(:,2) = 1 - reSult(:,1);
copy(reSult);
% copy(ConS);

end
```

FIG. 16C

```
function reSult2 = consensusdata2(M, Templ, ClusterSize, Grp)
% deduce a vector of 2nd consensus data using a matrix of 1st
dimemsional consensus
% inputs are (1) M = matrix of digitized sequences, (2) Templ =
ref sequence
% (3) ClusterSize = number of elements per group, (4) Grp =
number of groups
% outputs are (1) reSult2 = % number of correct bases
%
% Example:
% M= paste; Templ = paste;
% ClusterSize = 2;
% Grp = 1;
% reSult2 = consensusdata2(M, Templ, ClusterSize, Grp);
% copy(reSult);

%M = a matrix of 1D consensus with even # of rows
B = size(M,1);
reSult2 = zeros(B/ClusterSize, 1);

y = 1;
for k = 1:B/ClusterSize
    [reSult, ~] = consensusdata(M(y:k*ClusterSize, :), Templ,
ClusterSize, Grp);
    reSult2(k,1) = reSult;
    y = y + ClusterSize;
end
end
```

FIG. 16D

METHODS AND COMPOSITIONS FOR AMPLIFYING DNA AND GENERATING DNA SEQUENCING RESULTS FROM TARGET-ENRICHED DNA MOLECULES

CLAIM OF PRIORITY

None.

SEQUENCE LISTING

The instant application contains a Sequence Listing which has been filed electronically in ASCII format and is hereby incorporated by reference in its entirety. Said ASCII copy, created on Apr. 22, 2022, is named 13982-706-200_ST25.txt and is 18 KB in size.

INCORPORATION BY REFERENCE

All publications and patent applications mentioned in this specification are herein incorporated by reference in their entirety to the same extent as if each individual publication or patent application was specifically and individually indicated to be incorporated by reference, and for any purpose. When definitions of terms in incorporated references appear to differ from the definitions provided in the present teachings, the definition provided in the present teachings shall control.

BACKGROUND

Unique molecular identifiers (UMIs), or molecular barcodes, have been used widely in massive parallel sequencing (e.g., next generation sequencing, NGS) since its introduction in 2011, and helps improve the sensitivity of NGS while providing a quantitative tool for the measurement of mutations. The adoption of UMI in NGS ushers in an era of liquid biopsy. After ten years of development of various UMI technologies, UMI has been successfully used in liquid biopsy tests involving several types of cancers in advanced stages. However, many problems persist when UMI technology is used in testing early-stage cancers. The first major problem is that the detection of rare mutations (below 0.5% variant allele frequency) is unreliable and varies widely between assays, represented by the high levels of the false positives and false negatives. The second challenge is the sampling of rare ctDNA fragments. The root cause for these two major problems arises from the techniques used in making the libraries for liquid biopsy.

UMI, in the form of a stretch of random bases or degenerate nucleotides, was first used to label the target molecules through either PCR or ligation. Subsequently, many variations of both PCR- and ligation-based methods were developed. These include (but are not limited to) the PCR-based methods of TAM-seq, eTAM-seq, SAFE-SeqS, SiMSen-Seq, Kou 2016, AmpliSeq HD, and the ligation-based methods of Duplex-Seq, Tec-Seq, Kukita 2015, SPE, SPE-Duplex UMI, CAPP-Seq, iDES eCAPP-Seq, SLHC-Seq. Recently, several novel approaches have emerged. These include TARDIS, which is a hybrid of ligation and linear PCR, and ATOM-Seq, where UMI is added onto target via attaching and extending a loop-stem UMI adapter.

PCR-based technologies often use 2 to 3 cycles of PCR to assign one or a few UMIs to one target molecule, so that a quantitative ratio between UMI and the target is preserved. A limited number of PCR cycles is critical to avoid introducing redundant UMIs onto the same target molecule. However, this requirement hinders the amplification of the rare ctDNA targets to a level that is high enough for efficient downstream DNA manipulations. Ligation-based methods usually utilize unique approaches to minimize the loss of the precious ctDNA, maximize the efficiency of adapter ligation and avoid the base errors during end-repairing the target molecules. The requirement of quantitative assignment of UMI to target molecules also places a limit on the PCR amplification of the targets, unless the sequences of UMIs on both sense and antisense strands are complementary (such as in Duplex-Seq, discussed below). The limitation of target amplification contributes, at least partially, to the difficulties in sampling rare ctDNA targets.

One of the most important functions of UMI is its power to reduce random errors that are frequently observed in NGS. UMI allows condensing the sequences in each UMI clone into a consensus sequence, where the random errors on individual sequences are eliminated. The majority of the above-mentioned methods organize the target molecules with UMI to form a one-dimensional UMI array, and deduce consensus sequence once. We call this category of techniques single consensus methods. However, single consensus is ineffective to remove errors, especially those in low (<0.5%) variant allele frequencies. The inefficient power of single consensus techniques exacerbates the problem of detecting rare mutations.

Duplex-Seq is a promising alternative, but also suffers from a number of problems. In addition to the one-dimensional array of UMIs, Duplex-Seq recognizes the complementary UMIs on both sense and antisense strand of the same molecule and forms a matrix of two-dimensional UMIs providing a double consensus technique. The complementary nature of the UMIs on both strands of the same molecule allows the target DNA to be well amplified from a few nanograms to the level of micrograms. This allows the targets to be easily enriched downstream by hybridization capture, and has demonstrated superior power in removing random errors, and detecting rare mutations with ultra-high sensitivity and accuracy. However, a major problem has persisted since its introduction. Duplex-Seq requires a complementary pair of UMIs on the same molecule to be recovered, however, the sequences of UMIs changes (in other words, the random errors occur in the sequences of UMIs) during the process of making the library and sequencing. Only ~5-15% of the recovered UMIs are recognizable to be complementary in Duplex-Seq. This major drawback requires a very large amount of DNA be used in making library, a deep depth of sequencing, and a considerably high cost of sequencing.

The strategy of double consensus has demonstrated its power in sensitivity and accuracy, as well as the popularity of the method itself. It has further sparked many other attempts that utilize various approaches to reach the effect of a two-dimensional UMI matrix. These methods include a few improvement of the Duplex-Seq (e.g., BotSeqS, PECC-Seq, NanoSeq), several rolling cycle related methods and Pro-Seq, which colonizes UMIs on the same molecule; BiSeqS, which creates strand asymmetry via bisulfite conversion; MAPs, which splits a sample into two pools; and PhasED, which detects multiple mutations on one target.

Unfortunately all of these technique suffer from problems and disadvantages that may skew the results and add additional time and cost. What is needed are methods and compositions that may address these limitations.

SUMMARY OF THE DISCLOSURE

Described herein are methods and compositions (including kits), for reducing base errors in sequencing double-stranded DNA targets and methods of amplifying a plurality of target specific double-stranded DNA targets. These methods may be referred to generally as "SubDivision-Seq" techniques, and may address the major technical problems of existing UMI technology: sensitivity and accuracy in detecting low quantities of ctDNA, low UMI utilization rate in double consensus, and high sequencing cost. This methods and compositions described herein form a two-dimensional matrix of UMIs and forms the first dimensional UMI array through the UMIs placed on one-side (either 5' or 3' end) of the target molecules. These methods and compositions may allow low quantities of sample DNA to be amply amplified together with the first dimensional UMIs without creating redundant UMIs. After amplification, these methods subdivide the primary UMI clones into subclones through the UMIs placed on the other side of the molecules. Double consensus may be deduced by condensing the sequences within each subclone of UMI, and by the sequences within each primary UMI clone. These techniques do not require a complementary pair of UMIs to be recovered, nor a matched number of subclones representing the sense and antisense strand to co-exist within the primary UMI clone. These techniques may reach a high sensitivity and accuracy through initial DNA amplification and double consensus, and may significantly improve the efficiency of UMIs usage while reducing sequencing cost.

In general, the methods and compositions (including systems and kits) described herein relate to the amplification of nucleotide sequences, or the making of DNA libraries. In particular, the methods, compositions and systems described herein relate to increasing the sensitivity and accuracy of amplifying multiple different DNA fragments and reducing random errors of nucleotide incorporation during amplification and/or sequencing. The methods and compositions described herein may include analyzing unique molecular identifier (UMI) or molecular barcode and target DNA by massive parallel sequencing or high throughput sequencing (next generation sequencing, NGS).

Described herein are methods (e.g., strategies, techniques, etc.) and compositions (e.g., systems, kits, etc.) for generating highly sensitive and accurate sequencing results of massive parallel sequencing (NGS). The methods and compositions described herein may be referred to as SubDivision-Seq. SubDivision-Seq may comprise two parts (FIG. 1). The first part includes making a target-enriched DNA library, organizing the UMIs on DNA molecules to form primary clones and subdividing the primary clones into subclones. The second part includes sequencing the DNA library by NGS and nucleotide sequence analysis.

The first part of the technique may include amplifying each of the target DNA molecule into a primary clone defined by UMIs attached onto them, and subdividing the primary clone into subclones by using a plurality of UMI-containing target-specific primers (the panel) plus further amplification. In the first part, for example, the UMIs may be placed on specific positions of an adapter and each reverse primer of a target-specific primer panel. The primary clones are formed through ligation of the UMI-containing adapter onto to target DNA molecules, followed by PCR amplification. Each of the primary clone is subdivided into subclones through the annealing and extension of the panel to the amplified DNA molecules, followed by removing single-stranded DNA regions and molecules, and PCR amplification. A targeted DNA library is made after finishing the above process. In each primary clone, the DNA molecules share the same UMI sequence on one side of the molecules, while on the opposite side, the UMIs form multiple subclones. In a different phrasing of the same concept, the UMIs are organized into a two-dimensional matrix.

The second part of the technique may include sequencing the DNA library by massive parallel sequencing (high throughput sequencing, NGS), sorting the UMIs on one side of the molecules into primary clones, and sorting the UMIs on the other side of the molecules into subclones within each primary clone. These processes may include correcting base errors in the sequence of UMI and examining the length of the molecule and the end sequence on the side of the primary UMI. It further includes deducing consensus sequence within each subclone, deducing consensus sequence within each primary clone (from the consensus sequences obtained from subclones), and removing random errors that associate in NGS.

SubDivision-Seq differs from other techniques involving UMIs in deploying UMIs and deducing consensus sequences (FIGS. 2A-2C). Most UMI methods form a one-dimensional matrix of UMI, in contrary, Duplex-Seq and SubDivision-Seq form a two-dimensional matrix of UMI. However, Duplex-Seq requires the presence of two UMI clones, representing the sense and antisense strand of the same molecule, respectively, and the UMIs on these two clones are complementary. These two clones retain their lineage to the two strands of the original DNA molecule. It depends on the Y-shaped double-stranded UMI adapter that is used in ligation. Condensing of the two clones leads to two consensus sequences, which are used to deduce the final consensus sequence. In contrast, SubDivision-Seq employs multiple subclones (≥3) within each primary clone. It doesn't mandatorily require the subclones to be derived from both sense and antisense strand, nor an equal number of clones representing the sense and antisense strand are necessary. In fact, the sense and antisense strand loss their identity after the subdivision. The subclones are a mixture of sense and antisense strand in any number and combinations. SubDivision-Seq doesn't depend on any specific type of adapters, it accepts both single-stranded and double-stranded adapters. SubDivision-Seq requires ≥3 subclones for each primary clone, and use ≥3 consensus sequences derived from subclones for the final sequence condensing in each primary clone.

In one example, SubDivision-Seq starts from end repair and phosphorylating the 5' ends of the DNA fragments (FIG. 3). A DNA adapter is then ligated to the ends of the DNA fragments on both sides. The DNA adapter comprises a UMI region and a universal primer region. The DNA fragments are amplified with a universal primer in PCR. A panel of target-specific primers is then annealed onto the amplified DNA fragments, followed by extension, wherein each of this target-specific primers comprises a target specific region, a UMI region and a second universal primer region, wherein at least two and up to one hundred thousand target specific primers are included, and wherein the target specific primers are forward, or reverse, or both forward and reverse PCR primers. The single stranded regions in the resulting structures, as well as the remaining primers and primer-dimers, are then reduced or removed enzymatically. The target DNA molecules are amplified in a second PCR with a pair of universal primers. The sample indexes and sequencing primers are simultaneously added during the second PCR. The finished library is ready for massive parallel sequencing.

In one example, SubDivision-Seq starts from end repair and phosphorylating the 5' ends of the DNA fragments (FIG. 4). A DNA adapter is then ligated to the ends of the DNA fragments on both sides. The DNA adapter comprises a universal primer region. The DNA fragments are amplified with a universal primer in PCR. The primary clones are formed and identified by the nucleotide sequences and the length of the DNA molecules. A panel of target-specific primers is then annealed onto the amplified DNA fragments, followed by extension, wherein each of this target-specific primers comprises a target specific region, a UMI region and a second universal primer region, wherein at least two and up to one hundred thousand target specific primers are included, and wherein the target specific primers are forward, or reverse, or both forward and reverse PCR primers. The single stranded regions in the resulting structures, as well as the remaining primers and primer-dimers, are then reduced or removed enzymatically. The target DNA molecules are amplified by a second PCR with a pair of universal primers. The sample indexes and sequencing primers are simultaneously added during the second PCR. The finished library is ready for massive parallel sequencing.

In one example, a sample-index-containing UMI adapter is ligated onto the DNA fragments, and a hybridization capture of target molecules is applied following the amplification and pooling of samples (FIG. 5). SubDivision-Seq starts from end repair and phosphorylating the 5' ends of the DNA fragments. A DNA adapter is then ligated to the ends of the DNA fragments on both sides. The DNA adapter comprises a universal primer region, a UMI region and a sample barcode region. The DNA fragments are amplified with a universal primer in PCR. Multiple samples with different sample indexes are pooled. The target molecules are enriched by hybridization capture with a pool of target-specific oligos. A panel of target-specific primers is then annealed onto the amplified DNA fragments, followed by extension, wherein each of this target-specific primers comprises a target specific region, a UMI region and a second universal primer region, wherein at least two and up to one hundred thousand target specific primers are included, and wherein the target specific primers are forward, or reverse, or both forward and reverse PCR primers. The single stranded regions in the resulting structures, as well as the remaining primers and primer-dimers, are then reduced or removed enzymatically. The target DNA molecules are amplified by a second PCR with a pair of universal primers. The sample indexes and sequencing primers are simultaneously added during the second PCR. The finished library is ready for massive parallel sequencing.

In one example, a deoxyuridine (dU)-containing universal primer is used to amplify DNA fragments after adapter ligation (FIG. 6). SubDivision-Seq starts from end repair and phosphorylating the 5' ends of the DNA fragments. A DNA adapter is then ligated to the ends of the DNA fragments on both sides. The DNA adapter comprises a universal primer region and a UMI region. The DNA fragments are amplified with a dU-containing universal primer in PCR. A panel of target-specific primers is then annealed onto the amplified DNA fragments, followed by extension, wherein each of this target-specific primers comprises a target specific region, a UMI region and a second universal primer region, wherein at least two and up to one hundred thousand target specific primers are included, and wherein the target specific primers are forward, or reverse, or both forward and reverse PCR primers. The Us in the resulting structures are cleaved by uracil DNA glycosylase and apurinic/apyrimidinic endonuclease, leaving nicks at dU sites on double-stranded DNA and breaks at dU sites on single-stranded DNA. The target DNA molecules are amplified by a second PCR with a pair of universal primers, while the non-target DNA molecules are un-amplifiable. The sample indexes and sequencing primers are simultaneously added during the second PCR. The finished library is ready for massive parallel sequencing.

In one example, the method of SubDivision-Seq is used to amplify a plurality of DNA targets with hybridization capture. It starts from end repair and phosphorylating the 5' ends of the DNA fragments. A DNA adapter is then ligated to the ends of the DNA fragments on both sides. The DNA adapter comprises a universal primer region, a sample barcode region and optionally a UMI region. The DNA fragments are amplified with a universal primer in PCR. Multiple samples with different sample indexes are pooled. The target molecules are enriched by hybridization capture with a pool of target-specific oligos. A panel of target-specific primers is then annealed onto the amplified DNA fragments, followed by extension, wherein each of this target-specific primers comprises a target specific region, a second universal primer region and optionally a UMI region, wherein at least two and up to one hundred thousand target specific primers are included, and wherein the target specific primers are forward, or reverse, or both forward and reverse PCR primers. The single stranded regions in the resulting structures, as well as the remaining primers and primer-dimers, are then reduced or removed enzymatically. The target DNA molecules are amplified by a second PCR with a pair of universal primers.

In one example, the method of SubDivision-Seq is used to amplify a plurality of DNA targets without hybridization capture. It starts from end repair and phosphorylating the 5' ends of the DNA fragments. A DNA adapter is then ligated to the ends of the DNA fragments on both sides. The DNA adapter comprises a universal primer region and optionally a UMI region. The DNA fragments are amplified with a universal primer in PCR. A panel of target-specific primers is then annealed onto the amplified DNA fragments, followed by extension, wherein each of this target-specific primers comprises a target specific region, a second universal primer region and optionally a UMI region, wherein at least two and up to one hundred thousand target specific primers are included, and wherein the target specific primers are forward, or reverse, or both forward and reverse PCR primers. The single stranded regions in the resulting structures, as well as the remaining primers and primer-dimers, are then reduced or removed enzymatically. The target DNA molecules are amplified by a second PCR with a pair of universal primers.

In one example, the method of SubDivision-Seq is used to amplify a plurality of DNA targets with a dU-containing universal primer. It starts from end repair and phosphorylating the 5' ends of the DNA fragments. A DNA adapter is then ligated to the ends of the DNA fragments on both sides. The DNA adapter comprises a universal primer region and optionally a UMI region. The DNA fragments are amplified with a dU-containing universal primer in PCR. A panel of target-specific primers is then annealed onto the amplified DNA fragments, followed by extension, wherein each of this target-specific primers comprises a target specific region, a second universal primer region and optionally a UMI region, wherein at least two and up to one hundred thousand target specific primers are included, and wherein the target specific primers are forward, or reverse, or both forward and reverse PCR primers. The Us in the resulting structures are cleaved by uracil DNA glycosylase and apurinic/apyrimidinic endonuclease, leaving nicks at dU sites on double-stranded DNA and breaks at dU sites on single-stranded DNA. The target DNA molecules are amplified by a second PCR with a pair of universal primers, while the non-target DNA molecules are un-amplifiable.

Any method and strategy of adapter design and ligation reactions, in which the UMIs on the adapter form clones through PCR amplification, may be used in the methods and compositions described herein (FIGS. 7A-7C). For example, ligating a single-stranded UMI-containing DNA adapter to the 5' ends of the DNA molecules, or ligating a double-stranded UMI-containing DNA adapter to the both ends of the DNA molecules, or ligating a single-stranded UMI-containing DNA adapter to the 3' ends of the DNA molecules, may be equally well suited for the strategies, systems, methods and compositions described herein. For a second example, the above mentioned single-stranded UMI-containing DNA adapter may contain a stretch of RNA, and/or contain modifications at 5' and/or 3' end. For a further example, the above mentioned double-stranded UMI-containing DNA adapter may contain a complementary region of UMI, or a non-complementary region of UMI. The above examples do not intend to exhaust the possibilities of the methods and strategies of adapter design and ligation reactions. There may exist an unlimited number of methods to attach a UMI-containing adapter to the target DNA molecules. But they all fall within the concept of forming primary UMI clones and subdividing each primary UMI clone into subclones, or forming a two-dimensional matrix.

Many other examples of the concepts of SubDivision Seq are possible. These may include, but not limited to, using a panel of forward target specific primers, or a panel of both forward and reverse target specific primers, using various adapters, using various combinations of PCR and hybridization capture, switching a region of nucleotide sequence through utilizing U-containing primer and enzymatic manipulations, etc. It is almost impossible to exhaust the number and the types of these variations in details and in depictions. All of these examples, through various designs and technical approaches, may include the concept of dividing a primary UMI clone (or UMI cluster) derived from a double-stranded DNA molecule or a single-stranded DNA molecule into multiplex UMI subclones (or subclusters).

In the foregoing examples, one or more of the method steps is conducted in manual mode or in an automated mode or a combination thereof. In particular examples each of the method steps is carried out in automated mode. In some examples the foregoing methods further comprise at least one purification step. In particular examples a purification step is carried out only after the second PCR. In other particular examples a purification is carried out after the digestion step and an additional purification is carried out after the second PCR. In some examples the hybridization capture uses a plurality of biotin-labeled target specific oligos for capturing with streptavidin-coupled magnetic beads. In some of the examples the primer-dimer byproducts are removed from the resulting library. In some of the examples the primer-dimer byproducts are reduced from the resulting library. In certain examples, primer-dimer byproducts are eliminated. In some examples, the foregoing methods comprise digestion reagent selected from any one or a combination of T4 endonuclease VII, T7 endonuclease I, endonuclease I, endonuclease V, Nth endonuclease III, endonuclease VII, endonuclease VIII, uracil DNA glycosylase (UDG), apurinic endonuclease (e.g., APE1), RecJf, formamidopyrimidine [fapy]-DNA glycosylase (fpg), nuclease S1, nuclease P1, mung bean nuclease, nuclease CEL I, T4 DNA polymerase, T7 DNA polymerase, phi29 DNA polymerase. In some examples the foregoing methods comprise digestion reagent selected from any one or a combination of uracil DNA glycosylase (UDG), apurinic endonuclease (e.g., APE1) and formamidopyrimidine [fapy]-DNA glycosylase (fpg). In some examples, the foregoing methods further comprise analyzing the nucleotide sequence of the resulting targeted DNA library. Such analyzing comprises sequencing by traditional sequencing reactions, high throughput next generation sequencing, targeted multiplex array sequence detection, or any combination of two or more of the foregoing. In some examples, the foregoing methods further comprise deducing the consensus sequence from each UMI cluster of at least one target molecule in the sample. In other examples, the foregoing methods further comprise determining the abundance of at least one of the target nucleic acid sequences in the sample. In specific examples, the foregoing methods further comprise determining the low frequency allele(s) in a sample.

The methods and compositions described herein may be used with and/or may modify those described in U.S. patent application Ser. No. 15/290,981, filed on Oct. 11, 2016, which claims priority as a continuation-in-part to U.S. patent application Ser. No. 15/041,644, filed on Feb. 11, 2016, now U.S. Pat. No. 9,464,318, and titled "METHODS AND COMPOSITIONS FOR REDUCING NON-SPECIFIC AMPLIFICATION PRODUCTS", which claims priority to U.S. provisional patent applications: U.S. Provisional Patent Application No. 62/114,788, titled "A METHOD FOR ELIMINATING NONSPECIFIC AMPLIFICATION PRODUCTS IN MULTIPLEX PCR" and filed on Feb. 11, 2015; and U.S. Provisional Patent Application No. 62/150,600, titled "METHODS AND COMPOSITIONS FOR REDUCING NON-SPECIFIC AMPLIFICATION PRODUCTS" and filed Apr. 21, 2015. Each of these applications is herein incorporated by reference in its entirety. These methods and compositions described herein may be used with and/or may also modify those described in international patent application no. PCT/US2018/013143 and U.S. patent application Ser. No. 15/867,031, filed on Jan. 10, 2018, which claims priority to U.S. provisional patent applications: U.S. Provisional Patent Application No. 62/444,704, titled "METHODS AND COMPOSITIONS FOR REDUCING REDUNDANT MOLECULAR BARCODES CREATED IN PRIMER EXTENSION REACTIONS" and filed on Jan. 10, 2017. Each of these applications is herein incorporated by reference in its entirety.

For example, described herein are methods of reducing base errors in sequencing double-stranded DNA targets, wherein each primary clone of DNA target is subdivided into subclones along the course of DNA amplifications, wherein base errors are reduced by finding consensus sequence in each subclone and then in each primary clone. In some examples, the method includes: forming primary clones from double-stranded DNA molecules by: ligating an adapter to the ends of a plurality of double-stranded DNA molecules, wherein the adapter comprises a UMI and a first universal primer for PCR amplification, and the UMI comprises at least one degenerate or semi-degenerate base sequence, and amplifying the adapter-DNA complexes with the universal primer, resulting in each strand of the DNA molecule producing a clone of itself; subdividing each primary clone into subclones comprising: annealing and extending a plurality of target specific primers to the primary clones, wherein each of the target specific primer comprises a target-specific region, a UMI and a second universal primer for PCR amplification, resulting in each primary clone is subdivided into multiple subclones defined by the UMIs on the target specific primers on one side of the resulting molecules, while each primary clone is still identifiable by the UMI from the adapter on the other side of the resulting molecules, enzymatically removing the single-stranded regions from 3' ends in the above DNA structures, and amplifying the resulting products using the first and second universal primers; and removing base errors after sequencing, comprising: sorting sequences into primary clones by UMIs on the adaptors on one side of the molecules and the sequences of target molecules, then sorting each primary clone into subclones by the UMIs on the target specific primers on the other side of the molecules, and deducing consensus sequence from each subclone, then deducing consensus sequence in each primary clone from the consensus sequences obtained from the subclones within each primary clone.

A method of reducing base errors in sequencing double-stranded DNA targets, wherein each primary clone of DNA target is subdivided into subclones along the course of DNA amplifications, and wherein base errors are reduced by finding consensus sequence in each subclone and then in each primary clone, may include: forming primary clones from double-stranded DNA molecules by: ligating an adapter to the ends of a plurality of double-stranded target DNA molecules, wherein the adapter comprises a first universal primer for PCR amplification, wherein each primary clone is identified by the nucleotide sequences at both ends and the length of the DNA molecule, and amplifying the adapter-target complexes with the universal primer, resulting in each strand of the target molecule producing a clone of itself; subdividing each primary clone into subclones by: annealing and extending a plurality of target specific primers to the primary clones, wherein each of the target primer comprises a target-specific region, a UMI and a second universal primer for PCR amplification, resulting in each primary clone is subdivided into multiple subclones defined by the UMIs on the target specific primers of the resulting molecules, enzymatically removing the single-stranded regions from 3' ends in the above DNA structures, and amplifying the resulting products using the first and second universal primers; and removing base errors after sequencing by: sorting sequences into primary clones by the nucleotide sequences and the lengths of the target molecules, then sorting each primary clone into subclones by the UMIs on the target specific primers, and deducing consensus sequence from each subclone, then deducing consensus sequence in each primary clone from the consensus sequences obtained from the subclones within each primary clone.

A method of reducing base errors in sequencing double-stranded DNA targets, wherein each primary clone of DNA target is subdivided into subclones along the course of DNA amplifications, wherein base errors are reduced by finding consensus sequence in each subclone and then in each primary clone, may include: forming primary UMI clones from double-stranded DNA molecules by: ligating an adapter to the ends of a plurality of double-stranded DNA molecules, wherein the adapter comprises a UMI, a first universal primer for PCR amplification and a sample barcode, wherein the UMI comprises at least one degenerate or semi-degenerate base sequence; amplifying the adapter-DNA complexes with the universal primer, resulting in each strand producing a clone of itself; pooling samples and target enrichment by hybridization capture, including pooling together the amplified plurality of DNA molecules from multiple samples amplifying the adapter-DNA, followed by hybridization and capturing with a plurality of target specific oligos, wherein each of the target specific oligo is tagged with biotin moiety for capturing with streptavidin-coupled magnetic beads; subdividing each primary UMI clone into UMI subclones by: annealing and extending a plurality of target specific primers to the primary UMI clones, wherein each of the target primer comprises a target-specific region, a UMI and a second universal primer for PCR amplification, resulting in each primary clone is subdivided into multiple subclones defined by the UMIs on the target primers on one side of the resulting molecules, while each primary clone is still identifiable by the UMI from the adapter on the other side of the resulting molecules; enzymatically removing the single-stranded regions from 3' ends in the above DNA structures; and amplifying the resulting products using the first and second universal primers; and removing base errors after sequencing by: sorting sequences into primary UMI clones by UMI on one side of the molecules and the sequences of the plurality of the amplified targets, then sorting each primary clone into subclones by the UMI on the other side of the molecules, and deducing consensus sequence from each subclone, then deducing consensus sequence in each primary clone from the consensus sequences obtained from the subclones within each primary clone.

In any of the methods described herein, ligating the adapter may further comprise: blunting ends and phosphorylating the 5' ends of the DNA molecules, and/or ligating ssDNA adapter to 5' end of the DNA molecules, and/or ligating ssDNA adapter to 3' end of the DNA molecules, and/or ligating dsDNA adapter to the double strands of the DNA molecules, and/or ligating one strand of dsDNA adapter to 5' end of the DNA molecules, and/or ligating one strand of dsDNA adapter to 3' end of the DNA molecules, and/or tagging a ssDNA adapter by template switching.

In any of these methods described herein, the degenerate or semi-degenerate bases in UMI of the adapter ma have between 0 to 20 random bases.

Amplifying the adapter-DNA complex may comprise amplifying with one universal primer by PCR or linear amplification. Amplifying the adapter-DNA complexes may comprise amplifying with a pair of universal primers by PCR. In any of these methods or compositions, one or both of the universal primers may have one or multiple Us replacing Ts. The degenerate or semi-degenerate bases in the UMI of the target specific primer may have between 0 to 20 random bases. The preferred numbers of the random bases in the UMI of the target specific primer are 2, 3 and 4.

The plurality of target specific primers may be a panel of reverse primers, or a panel of forward primers, or a panel of both forward and reverse primers. The number of the plurality of target specific primers may be between 2-100,000.

In any of these examples, enzymatically removing the single-stranded regions may comprise removing single stranded DNA regions and single stranded DNA by using 3' to 5' single-strand DNA specific exonuclease. Enzymatically removing the single-stranded regions may further comprise, for U-containing universal primers, creating nicks in double stranded DNA and breaks in single stranded DNA at the sites of Us by using UDG and APE 1, or UDG and fpg, or UDG and Endo IV. Enzymatically removing the single-stranded regions may further comprise, for U-containing universal primers, removing single stranded DNA regions and single stranded DNA by using 3' to 5' single-strand DNA specific exonuclease, and creating nicks in double stranded DNA and breaks in single stranded DNA at the sites of Us by using UDG and APE 1, or UDG and fpg, or UDG and Endo IV.

In any of these methods, amplifying the resulting products may include adding sample barcodes. Any of these methods may include hybridization capture after amplifying the adapter-DNA complexes. In any of these methods deducing consensus sequence may further comprises calculating mutation frequency based on the number of clones of a specific mutation.

Also described herein are methods of amplifying a plurality of target-specific double-stranded DNA targets, the method comprising: amplifying the full spectrum of the DNA molecules in the sample by: ligating an adapter to the ends of a plurality of double-stranded DNA molecules, wherein the adapter comprises a first universal primer for PCR amplification and a UMI with at least one degenerate or semi-degenerate base sequence, and a sample barcode, and amplifying the adapter-target complexes with the universal primer; pooling samples and target enrichment by hybridization capture, comprising: pooling together the amplified plurality of DNA molecules from multiple samples after amplifying the adapter-target complexes, followed by hybridization and capturing with a plurality of target specific oligos, wherein each of the target specific oligo is tagged with biotin moiety for capturing with streptavidin-coupled magnetic beads; and amplifying a plurality of target specific double-stranded DNA targets by: annealing and extending a plurality of target specific primers to the hybridization capturing enriched DNA molecules, wherein each of the target primer comprises a target-specific region and a second universal primer for PCR amplification, each of the target primer further comprising a UMI with at least one degenerate or semi-degenerate base sequence, enzymatically removing the single-stranded regions from 3' ends in the above DNA structures, so that to make the non-target DNA un-amplifiable, and amplifying the resulting products using the first and second universal primers.

A method of amplifying a plurality of target specific double-stranded DNA targets may include: amplifying the full spectrum of the DNA molecules in the sample by: ligating an adapter to the ends of a plurality of double-stranded DNA molecules, wherein the adapter comprises a first universal primer for PCR amplification and a UMI with at least one degenerate or semi-degenerate base sequence, and optionally a sample barcode, and amplifying the adapter-target complexes with the universal primer; and amplifying a plurality of target specific double-stranded DNA targets by: annealing and extending a plurality of target specific primers to the DNA molecules, wherein each of the target primer comprises a target-specific region and a second universal primer for PCR amplification, wherein each of the target primers may further comprise a UMI with at least one degenerate or semi-degenerate base sequence, and enzymatically removing the single-stranded regions from 3' ends in the above DNA structures, so that to make the non-target DNA un-amplifiable, and amplifying the resulting products using the first and second universal primers.

A method of amplifying a plurality of target specific double-stranded DNA targets may include: amplifying the full spectrum of the DNA molecules in the sample by: ligating an adapter to the ends of a plurality of double-stranded DNA molecules, wherein the adapter comprises a first universal primer for PCR amplification, a UMI with at least one degenerate or semi-degenerate base sequence, and a sample barcode, and amplifying the adapter-target complexes with a U-containing universal primer; and amplifying a plurality of target specific double-stranded DNA targets by: annealing and extending a plurality of target specific primers to the DNA molecules, wherein each of the target primer comprises a target-specific region and a second universal primer for PCR amplification, each of the target primer may further comprise a UMI with at least one degenerate or semi-degenerate base sequence, creating nicks in double stranded DNA and breaks in single stranded DNA at the sites of Us by using UDG and APE 1, or UDG and fpg, or UDG and Endo IV, so that to make the non-target DNA un-amplifiable, and amplifying the resulting products using the first and second universal primers.

All of the methods and apparatuses described herein, in any combination, are herein contemplated and can be used to achieve the benefits as described herein.

BRIEF DESCRIPTION OF THE DRAWINGS

A better understanding of the features and advantages of the methods and apparatuses described herein will be obtained by reference to the following detailed description that sets forth illustrative embodiments, and the accompanying drawings of which:

FIGS. 8A-8D schematically illustrates techniques for making non-target DNA un-amplifiable. FIG. 8A shows removing single-stranded DNA regions and single-stranded DNA by a 3'→5' single stranded DNA specific exonuclease. FIG. 8B illustrates removing the universal primer binding site by using a dU-containing universal primers and digesting with UDG and APE 1 subsequently. FIG. 8C illustrates non-target DNA fragments are either destroyed or un-amplifiable. FIG. 8D illustrates target-specific primers may potentially bind to UMI region and generate non-specific products and off-target products.

FIGS. 12A-12D are graphs showing additional simulations and comparison with Duplex Seq. FIG. 12A is a comparison among separate sense and antisense strand, and randomly mixed sense and antisense strands. FIG. 12B shows a comparison between two UMI Clusters with mixed sense & antisense elements and Duplex Seq (two UMI Clusters with separate sense & antisense elements). FIG. 12C is a comparison between SubDivision Seq with 2 elements per UMI subclone and Duplex Seq at the same sequencing depth. FIG. 12D shows a comparison between SubDivision Seq with and Duplex Seq at the same sequencing depth.

FIG. 13A shows the probability of UMI collision of UMI containing 10-16 bases at 5-20 ng of input DNA. FIG. 13B is a graph showing validation of UMI collision by the recovered number of HGEs. FIG. 13C is a graph showing validation of UMI collision by the observed conversion rate.

FIGS. 15A-15D show fewer UMI errors were observed at low sequencing depth. FIG. 15A is a graph of a group of cfDNA libraries that were sequenced at increasingly higher depth, the lowest depth generated the lowest number of UMI clusters with 1 element and the highest number of UMI clusters with ≥3 elements. FIG. 15B shows similar results were found with a group of genomic DNA libraries. FIG. 15C shows the number of UMI clusters with 1 element was presumed to be lower at high sequencing depth when the number of elements per UMI clone is increased and the total number of UMI clones remains unchanged, but this didn't happen. FIG. 15D shows similar results were found collectively in cfDNA libraries sequenced at various depth.

FIGS. 16A-16D show one example of codes for finding consensus sequence as described herein.

DETAILED DESCRIPTION

Figure 1:
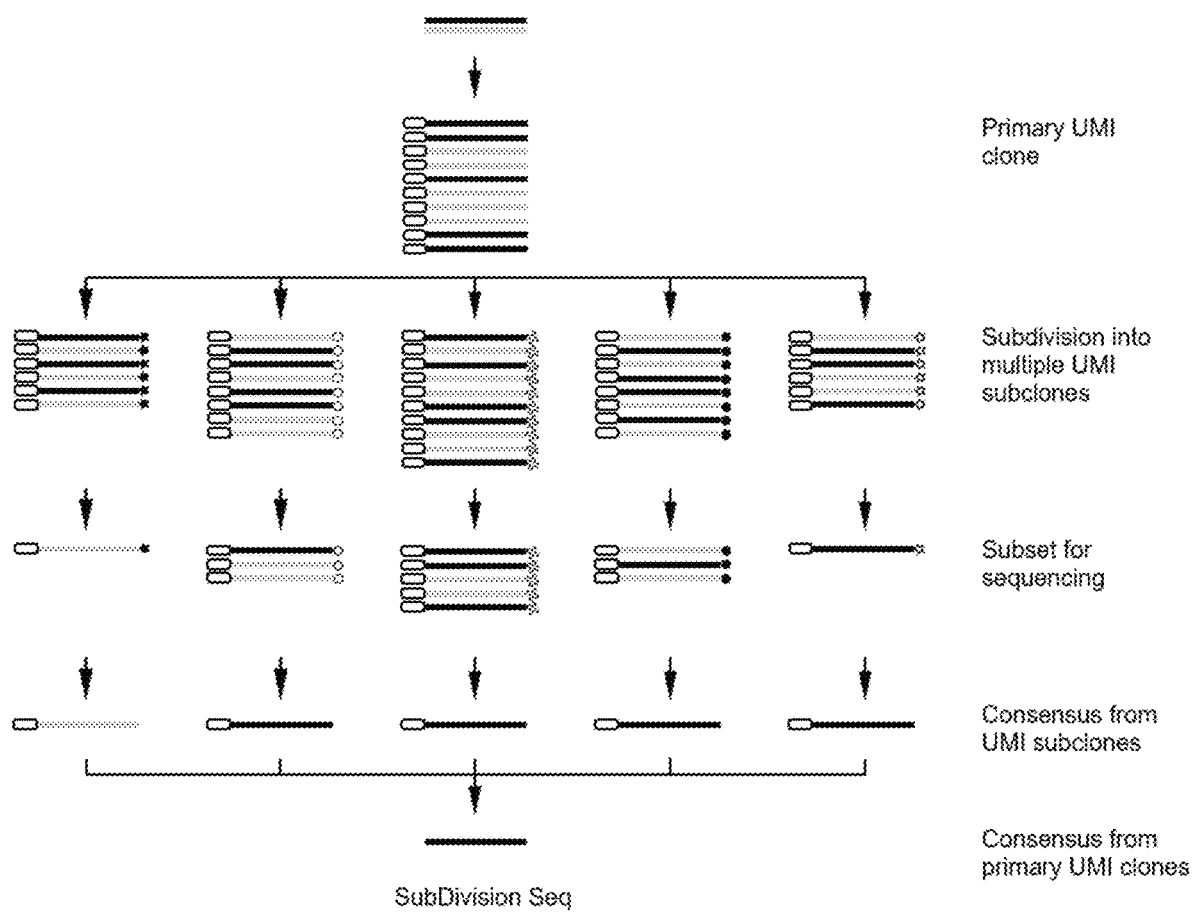
FIG. 1 schematically illustrates SubDivision-Seq, showing forming a primary UMI clone from one double-stranded DNA molecule, and subdividing the primary UMI clone into multiple UMI subclones.
Figure 2:
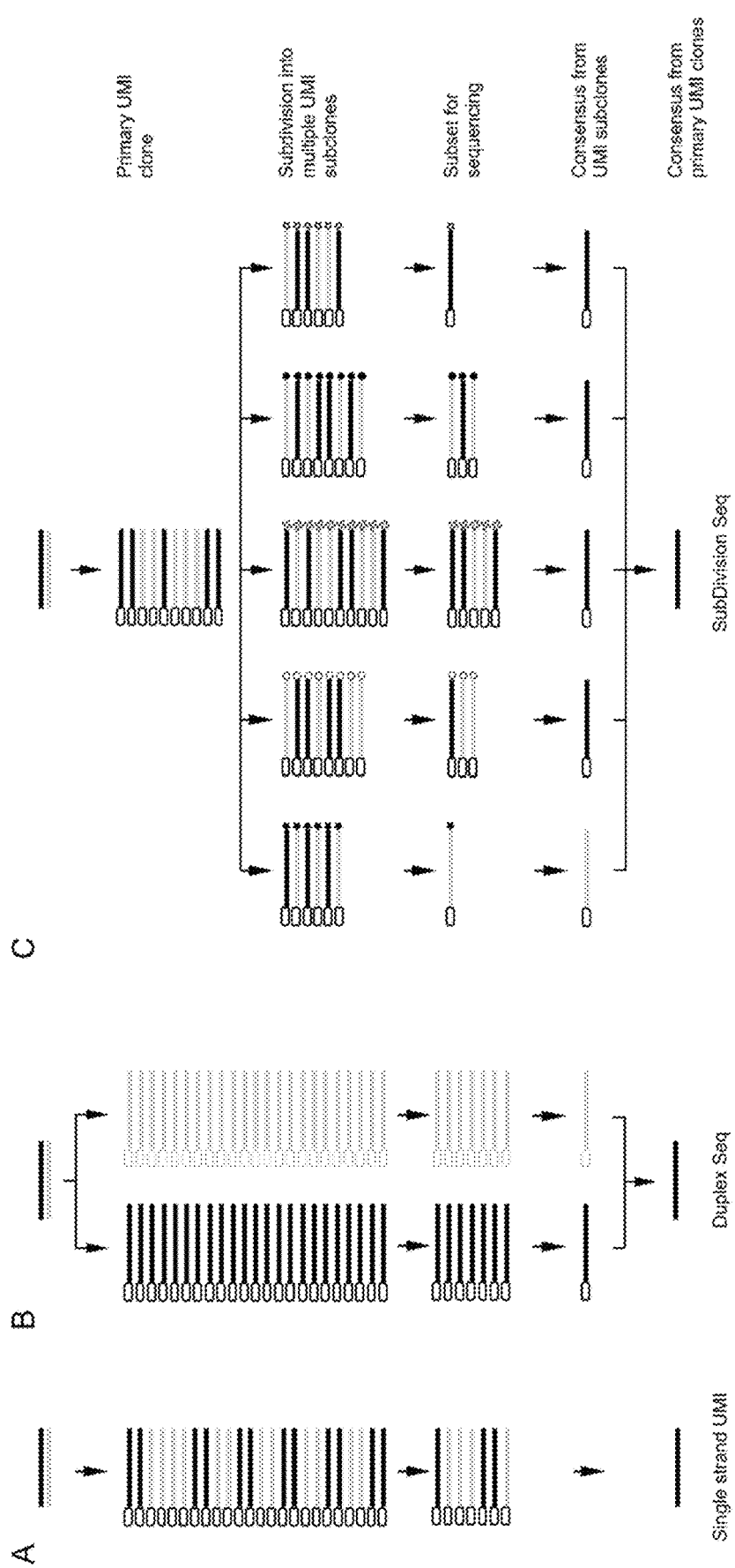
FIGS. 2A-2C schematically illustrates differences between SubDivision-Seq and other UMI containing technologies, including Single strand UMI (FIG. 2A), and Duplex Seq (FIG. 2B) as compared to SubDivision-Seq (FIG. 2C).
Figure 3:
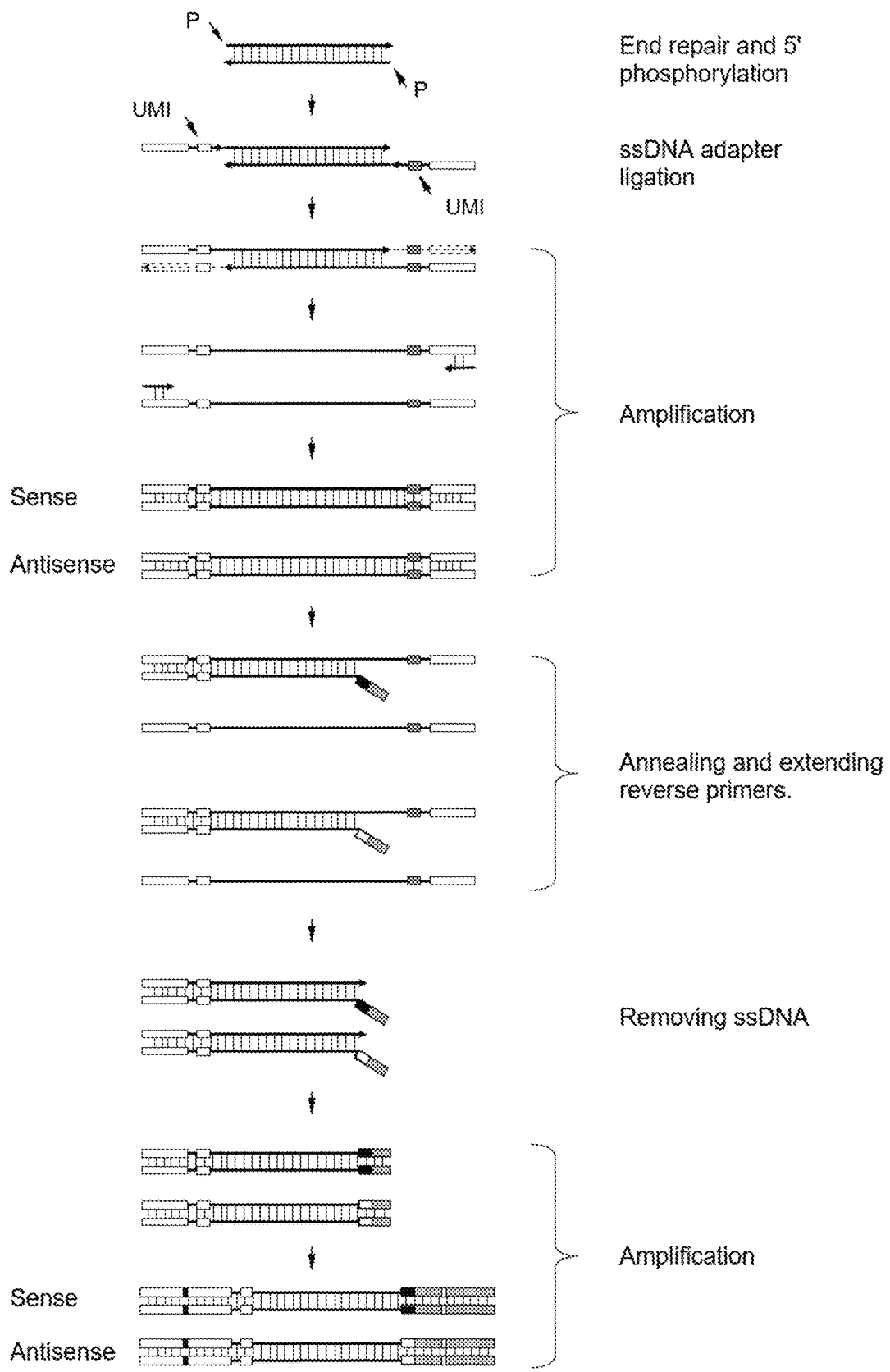
FIG. 3 schematically illustrates an example of SubDivision-Seq, ligating a single stranded an adapter to the 5' end of double stranded DNA molecules.
Figure 4:
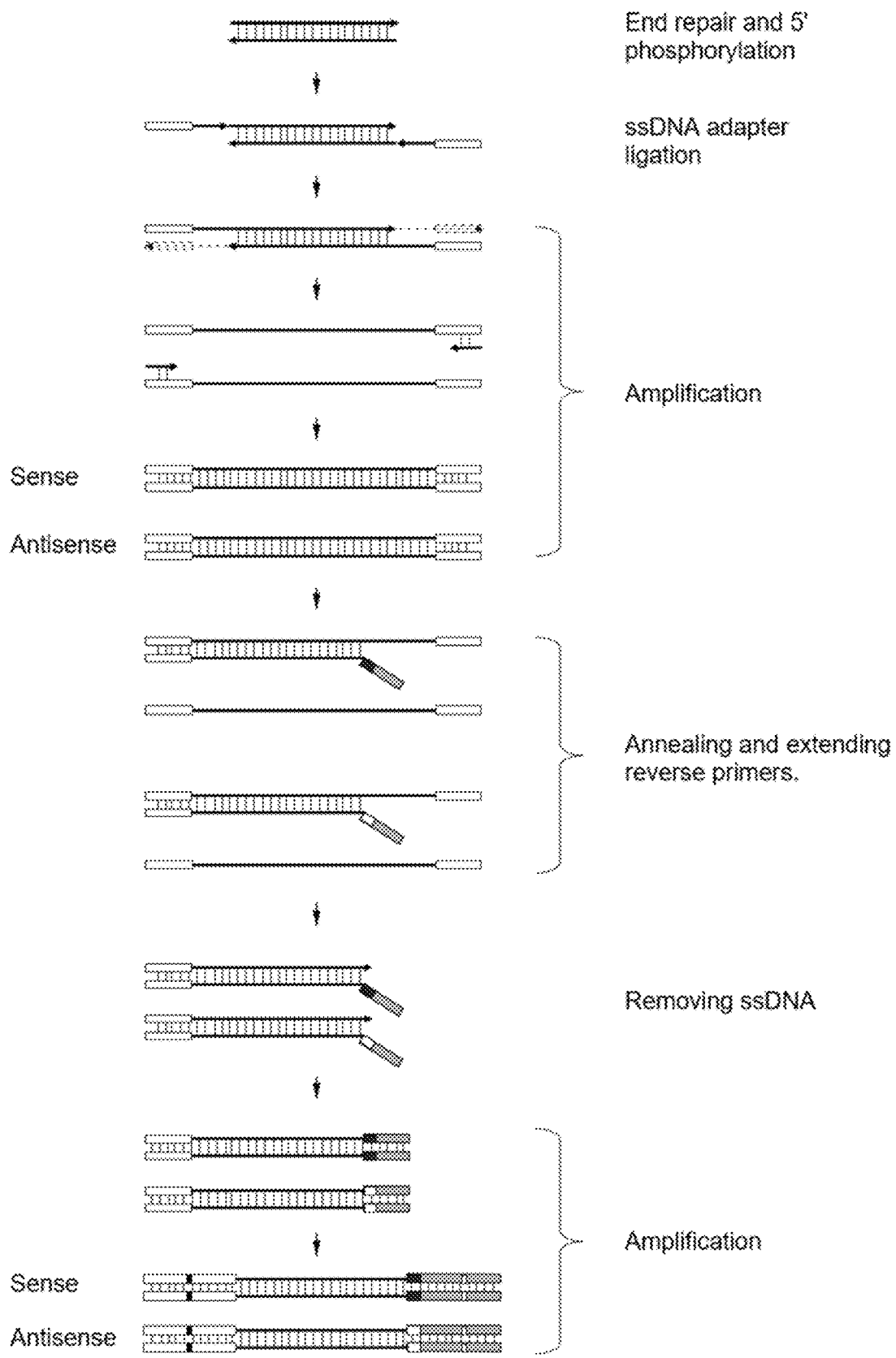
FIG. 4 schematically illustrates an example of SubDivision-Seq, employing nucleotide sequence and length of target DNA to identify primary clones.
Figure 5:
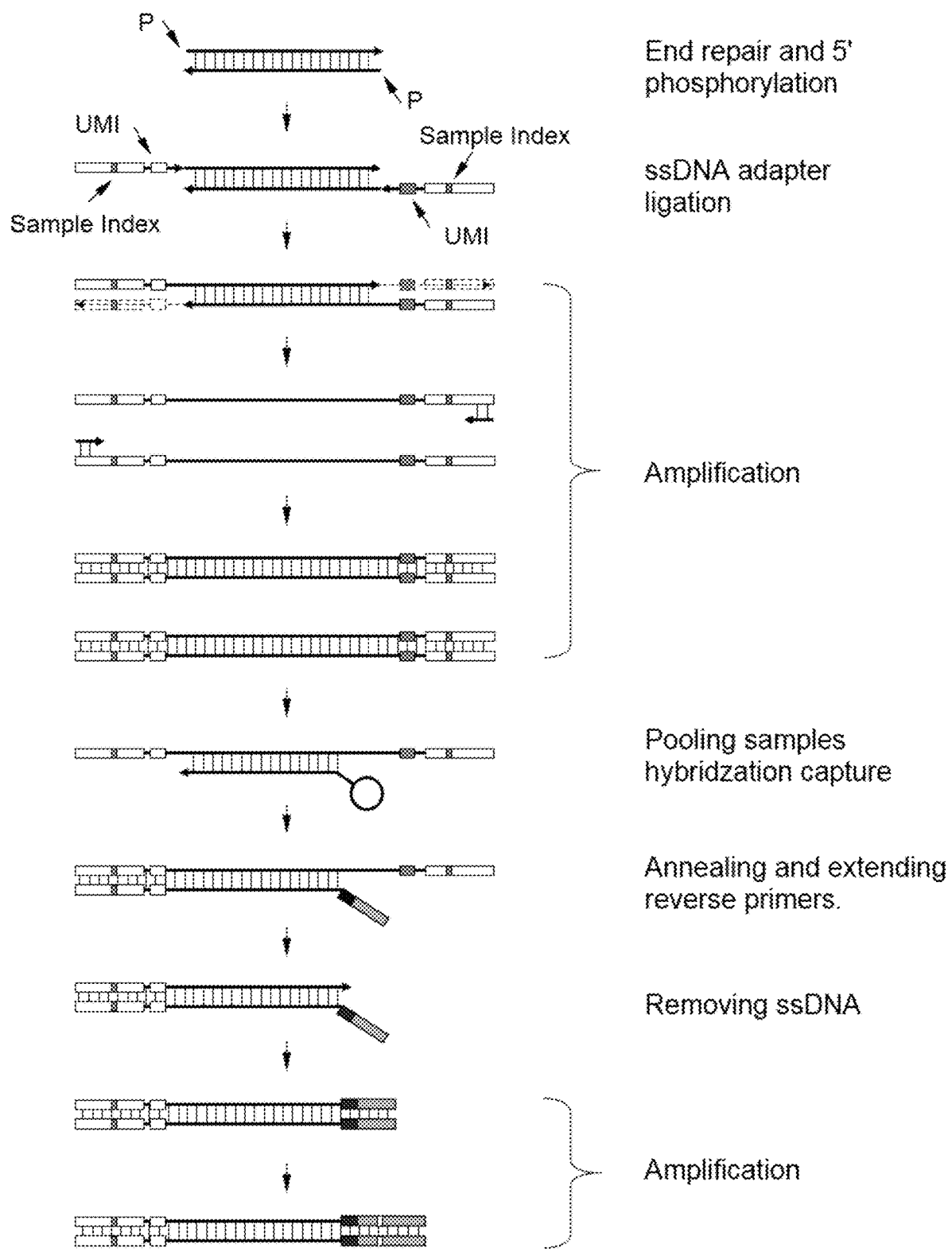
FIG. 5 schematically illustrates an example of SubDivision-Seq, employing hybridization capture.
Figure 6:
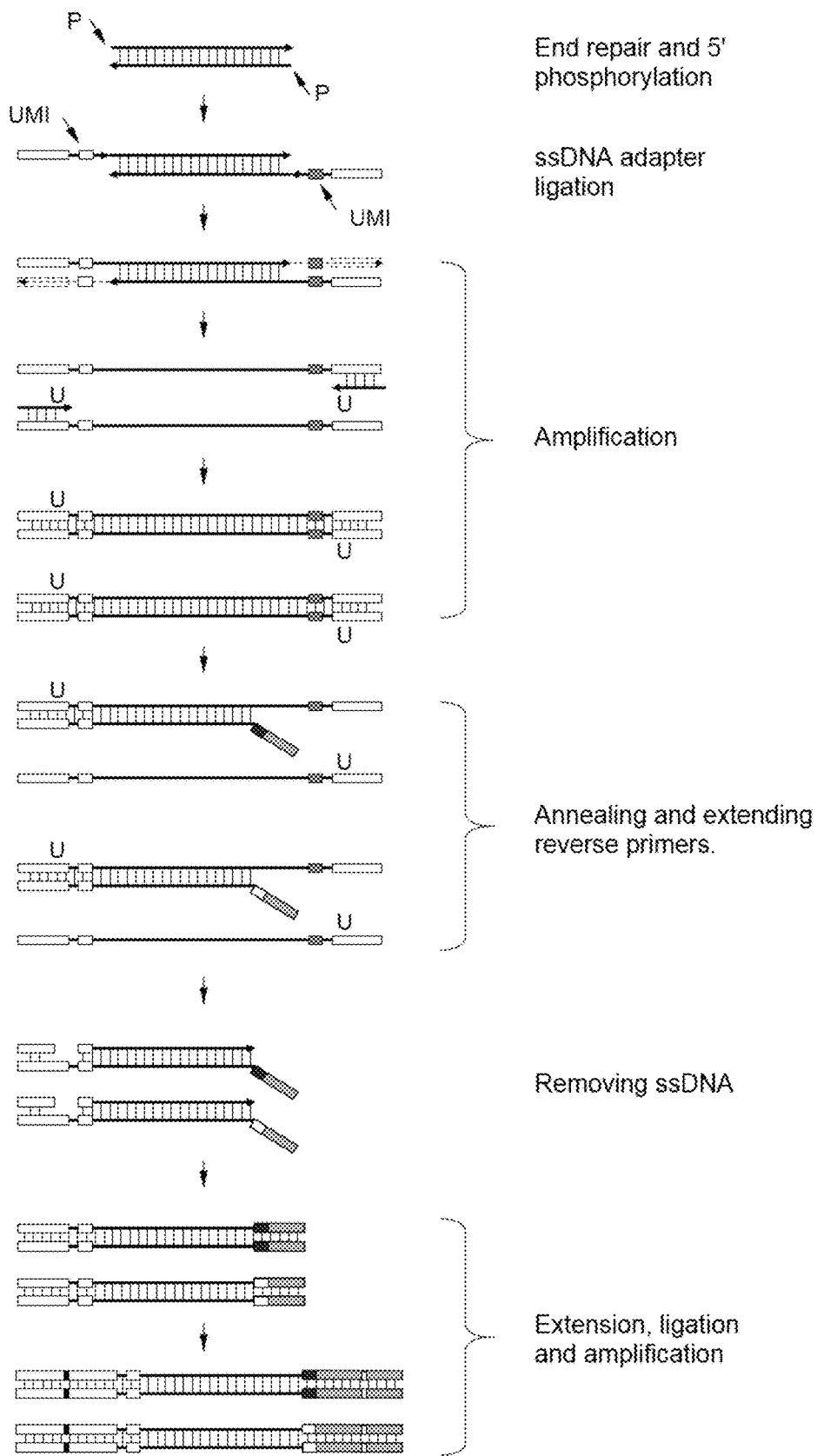
FIG. 6 schematically illustrates an example of SubDivision-Seq, employing a dU-containing universal primer.
Figure 7A:
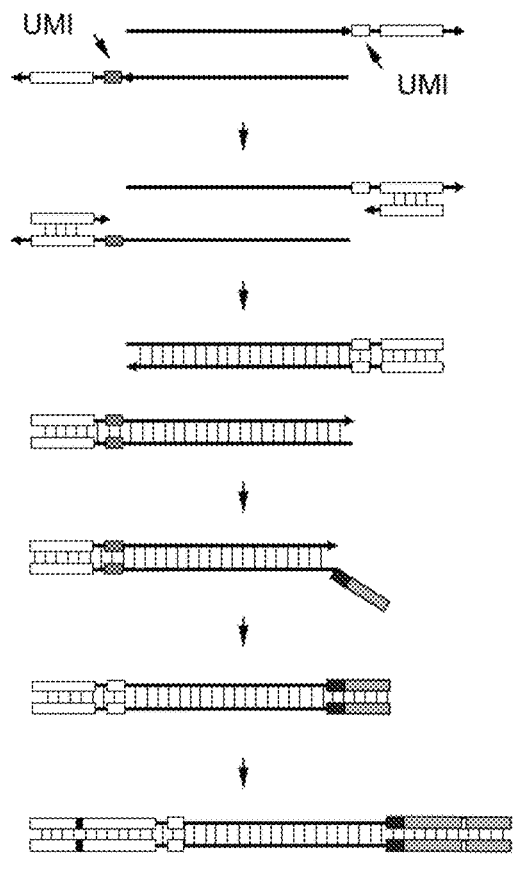
FIGS. 7A and 7B and 7C schematically illustrates examples of design and strategy of adapters and ligation reactions.
Figure 7B:
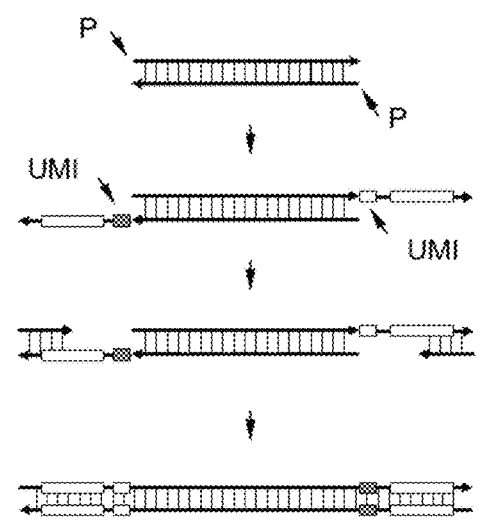
Figure 7C:
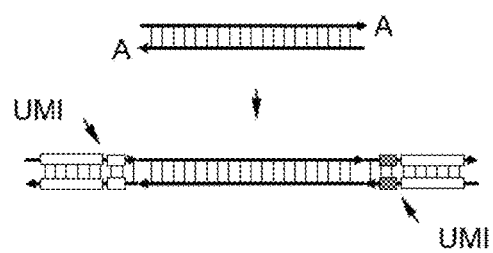

In general, described herein are strategies, systems, methods and compositions that may be used to generating highly sensitive and accurate sequencing results of NGS through the use of UMI. Unless otherwise defined, all technical and scientific terms used herein have the same meaning as commonly understood by one of ordinary skill in the art to which this invention belongs. Still, certain elements are defined for the sake of clarity and ease of reference.

Unless otherwise defined, scientific and technical terms used in connection with the invention described herein shall have the meanings that are commonly understood by those of ordinary skill in the art. Further, unless otherwise required by context, singular terms shall include pluralities and plural terms shall include the singular. Generally, nomenclatures utilized in connection with, and techniques of, cell and tissue culture, molecular biology, and protein and oligo- or polynucleotide chemistry and hybridization used herein are those well-known and commonly used in the art. Standard techniques are used, for example, for nucleic acid purification and preparation, chemical analysis, recombinant nucleic acid, and oligonucleotide synthesis. Enzymatic reactions and purification techniques are performed according to manufacturer's specifications or as commonly accomplished in the art or as described herein. Techniques and procedures described herein are generally performed according to conventional methods well known in the art and as described in various general and more specific references that are cited and discussed throughout the instant specification. See, e.g., Sambrook et al., Molecular Cloning: A Laboratory Manual (Third ed., Cold Spring Harbor Laboratory Press, Cold Spring Harbor, N.Y. 2000). Unless specifically provided, any nomenclature utilized in connection with, and laboratory procedures and techniques described herein are those well-known and commonly used in the art. As utilized in accordance with embodiments provided herein, the following terms, unless otherwise indicated, shall be understood to have the following meanings:

As used herein, "amplify", "amplifying" or "amplification reaction" and their derivatives, refer generally to an action or process whereby at least a portion of a nucleic acid molecule (referred to as a template nucleic acid molecule) is replicated or copied into at least one additional nucleic acid molecule. The additional nucleic acid molecule optionally includes sequence that is substantially identical or substantially complementary to at least some portion of the template nucleic acid molecule. A template target nucleic acid molecule may be single-stranded or double-stranded. The additional resulting replicated nucleic acid molecule may independently be single-stranded or double-stranded. In some examples, amplification includes a template-dependent in vitro enzyme-catalyzed reaction for the production of at least one copy of at least some portion of a target nucleic acid molecule or the production of at least one copy of a target nucleic acid sequence that is complementary to at least some portion of a target nucleic acid molecule. Amplification optionally includes linear or exponential replication of a nucleic acid molecule. In some examples, such amplification is performed using isothermal conditions; in other examples, such amplification can include thermocycling. In some examples, the amplification is a multiplex amplification that includes simultaneous amplification of a plurality of target sequences in a single amplification reaction. At least some target sequences can be situated on the same nucleic acid molecule or on different target nucleic acid molecules included in a single amplification reaction. In some examples, "amplification" includes amplification of at least some portion of DNA- and/or RNA-based nucleic acids, whether alone, or in combination. An amplification reaction can include single or double-stranded nucleic acid substrates and can further include any amplification processes known to one of ordinary skill in the art. In some examples, an amplification reaction includes polymerase chain reaction (PCR). In some examples, an amplification reaction includes isothermal amplification.

As used herein, "amplification conditions" and derivatives (e.g., conditions for amplification, etc.) generally refers to conditions suitable for amplifying one or more nucleic acid sequences.

Amplification can be linear or exponential. In some examples, amplification conditions include isothermal conditions or alternatively include thermocycling conditions, or a combination of isothermal and thermocycling conditions. In some examples, conditions suitable for amplifying one or more target nucleic acid sequences includes polymerase chain reaction (PCR) conditions. Typically, amplification conditions refer to a reaction mixture that is sufficient to amplify nucleic acids such as one or more target sequences, or to amplify an amplified target sequence ligated or attached to one or more adaptors, e.g., an adaptor-attached amplified target sequence. Generally, amplification conditions include a catalyst for amplification or for nucleic acid synthesis, for example a polymerase; a primer that possesses some degree of complementarity to the nucleic acid to be amplified; and nucleotides, such as deoxyribonucleoside triphosphates (dNTPs) to promote extension of a primer once hybridized to a nucleic acid. Amplification conditions can require hybridization or annealing of a primer to a nucleic acid, extension of the primer and a denaturing step in which the extended primer is separated from the nucleic acid sequence undergoing amplification. Typically, though not necessarily, amplification conditions can include thermocycling. In some examples, amplification conditions include a plurality of cycles wherein steps of annealing, extending and separating are repeated. Typically, amplification conditions include cations such as Mg++ or Mn++ (e.g., MgCh, etc.) and can also optionally include various modifiers of ionic strength.

As used herein, "target sequence" "target nucleic acid sequence" or "target sequence of interest" and derivatives, refers generally to any single or double-stranded nucleic acid sequence that can be amplified or synthesized according to the disclosure, including any nucleic acid sequence suspected or expected to be present in a sample. In some examples, the target sequence is present in double-stranded form and includes at least a portion of the particular nucleotide sequence to be amplified or synthesized, or its complement, prior to the addition of target-specific primers or appended adaptors. Target sequences can include the nucleic acids to which primers useful in the amplification or synthesis reaction can hybridize prior to extension by a polymerase. In some examples, the term refers to a nucleic acid sequence whose sequence identity, ordering or location of nucleotides is determined by one or more of the methods of the disclosure.

The term "portion" and its variants, as used herein, when used in reference to a given nucleic acid molecule, for example a primer or a template nucleic acid molecule, comprises any number of contiguous nucleotides within the length of the nucleic acid molecule, including the partial or entire length of the nucleic acid molecule.

As used herein, "contacting" and its derivatives, when used in reference to two or more components, refers generally to any process whereby the approach, proximity, mixture or commingling of the referenced components is promoted or achieved without necessarily requiring physical contact of such components, and includes mixing of solutions containing any one or more of the referenced components with each other. The referenced components may be contacted in any particular order or combination and the particular order of recitation of components is not limiting. For example, "contacting A with B and C" encompasses examples where A is first contacted with B then C, as well as examples where C is contacted with A then B, as well as examples where a mixture of A and C is contacted with B, and the like. Furthermore, such contacting does not necessarily require that the end result of the contacting process be a mixture including all of the referenced components, as long as at some point during the contacting process all of the referenced components are simultaneously present or simultaneously included in the same mixture or solution. For example, "contacting A with B and C" can include examples wherein C is first contacted with A to form a first mixture, which first mixture is then contacted with B to form a second mixture, following which C is removed from the second mixture; optionally A can then also be removed, leaving only B. Where one or more of the referenced components to be contacted includes a plurality (e.g., "contacting a target sequence with a plurality of target-specific primers and a polymerase"), then each member of the plurality can be viewed as an individual component of the contacting process, such that the contacting can include contacting of any one or more members of the plurality with any other member of the plurality and/or with any other referenced component (e.g., some but not all of the plurality of target specific primers can be contacted with a target sequence, then a polymerase, and then with other members of the plurality of target-specific primers) in any order or combination.

As used herein, the term "primer" and its derivatives refer generally to any polynucleotide that can hybridize to a target sequence of interest. In some examples, the primer can also serve to prime nucleic acid synthesis. Typically, a primer functions as a substrate onto which nucleotides can be polymerized by a polymerase; in some examples, however, a primer can become incorporated into a synthesized nucleic acid strand and provide a site to which another primer can hybridize to prime synthesis of a new strand that is complementary to the synthesized nucleic acid molecule. A primer may be comprised of any combination of nucleotides or analogs thereof, which may be optionally linked to form a linear polymer of any suitable length. In some examples, a primer is a single-stranded oligonucleotide or polynucleotide. (For purposes of this disclosure, the terms 'polynucleotide" and "oligonucleotide" are used interchangeably herein and do not necessarily indicate any difference in length between the two). In some examples, a primer is double-stranded. If double stranded, a primer is first treated to separate its strands before being used to prepare extension products. Preferably, the primer is an oligodeoxyribonucleotide. A primer must be sufficiently long to prime the synthesis of extension products. Lengths of the primers will depend on many factors, including temperature, source of primer and the use of the method. In some examples, a primer acts as a point of initiation for amplification or synthesis when exposed to amplification or synthesis conditions; such amplification or synthesis can occur in a template-dependent fashion and optionally results in formation of a primer extension product that is complementary to at least a portion of the target sequence. Exemplary amplification or synthesis conditions can include contacting the primer with a polynucleotide template (e.g., a template including a target sequence), nucleotides and an inducing agent such as a polymerase at a suitable temperature and pH to induce polymerization of nucleotides onto an end of the target-specific primer. If double-stranded, the primer can optionally be treated to separate its strands before being used to prepare primer extension products. In some examples, the primer is an oligodeoxyribonucleotide or an oligoribonucleotide. In some examples, the primer can include one or more nucleotide analogs. The exact length and/or composition, including sequence, of the target-specific primer can influence many properties, including melting temperature (Tm), GC content, formation of secondary structures, repeat nucleotide motifs, length of predicted primer extension products, extent of coverage across a nucleic acid molecule of interest, number of primers present in a single amplification or synthesis reaction, presence of nucleotide analogs or modified nucleotides within the primers, and the like. In some examples, a primer can be paired with a compatible primer within an amplification or synthesis reaction to form a primer pair consisting or a forward primer and a reverse primer. In some examples, the forward primer of the primer pair includes a sequence that is substantially complementary to at least a portion of a strand of a nucleic acid molecule, and the reverse primer of the primer of the primer pair includes a sequence that is substantially identical to at least of portion of the strand. In some examples, the forward primer and the reverse primer are capable of hybridizing to opposite strands of a nucleic acid duplex. Optionally, the forward primer primes synthesis of a first nucleic acid strand, and the reverse primer primes synthesis of a second nucleic acid strand, wherein the first and second strands are substantially complementary to each other, or can hybridize to form a double-stranded nucleic acid molecule. In some examples, one end of an amplification or synthesis product is defined by the forward primer and the other end of the amplification or synthesis product is defined by the reverse primer. In some examples, where the amplification or synthesis of lengthy primer extension products is required, such as amplifying an exon, coding region, or gene, several primer pairs can be created than span the desired length to enable sufficient amplification of the region. In some examples, a primer can include one or more cleavable groups. In some examples, primer lengths are in the range of about 10 to about 60 nucleotides, about 12 to about 50 nucleotides and about 15 to about 40 nucleotides in length.

Typically, a primer is capable of hybridizing to a corresponding target sequence and undergoing primer extension when exposed to amplification conditions in the presence of dNTPS and a polymerase. In some instances, the particular nucleotide sequence or a portion of the primer is known at the outset of the amplification reaction or can be determined by one or more of the methods disclosed herein. In some examples, the primer includes one or more cleavable groups at one or more locations within the primer.

As used herein, "target-specific primer" and its derivatives, refers generally to a single stranded or double-stranded polynucleotide, typically an oligonucleotide, that includes at least one sequence that is at least 50% complementary, typically at least 75% complementary or at least 85% complementary, more typically at least 90% complementary, more typically at least 95% complementary, more typically at least 98% or at least 99% complementary, or identical, to at least a portion of a nucleic acid molecule that includes a target sequence. In such instances, the target-specific primer and target sequence are described as "corresponding" to each other. In some examples, the target-specific primer is capable of hybridizing to at least a portion of its corresponding target sequence (or to a complement of the target sequence); such hybridization can optionally be performed under standard hybridization conditions or under stringent hybridization conditions. In some examples, the target-specific primer is not capable of hybridizing to the target sequence, or to its complement, but is capable of hybridizing to a portion of a nucleic acid strand including the target sequence, or to its complement. In some examples, the target-specific primer includes at least one sequence that is at least 75% complementary, typically at least 85% complementary, more typically at least 90% complementary, more typically at least 95% complementary, more typically at least 98% complementary, or more typically at least 99% complementary, to at least a portion of the target sequence itself; in other examples, the target-specific primer includes at least one sequence that is at least 75% complementary, typically at least 85% complementary, more typically at least 90% complementary, more typically at least 95% complementary, more typically at least 98% complementary, or more typically at least 99% complementary, to at least a portion of the nucleic acid molecule other than the target sequence. In some examples, the target-specific primer is substantially non-complementary to other target sequences present in the sample; optionally, the target-specific primer is substantially non-complementary to other nucleic acid molecules present in the sample. In some examples, nucleic acid molecules present in the sample that do not include or correspond to a target sequence (or to a complement of the target sequence) are referred to as "non-specific" sequences or "non-specific nucleic acids". In some examples, the target-specific primer is designed to include a nucleotide sequence that is substantially complementary to at least a portion of its corresponding target sequence. In some examples, a target-specific primer is at least 95% complementary, or at least 99% complementary, or identical, across its entire length to at least a portion of a nucleic acid molecule that includes its corresponding target sequence. In some examples, a target-specific primer can be at least 90%, at least 95% complementary, at least 98% complementary or at least 99% complementary, or identical, across its entire length to at least a portion of its corresponding target sequence. In some examples, a forward target-specific primer and a reverse target-specific primer define a target-specific primer pair that can be used to amplify the target sequence via template-dependent primer extension. Typically, each primer of a target-specific primer pair includes at least one sequence that is substantially complementary to at least a portion of a nucleic acid molecule including a corresponding target sequence but that is less than 50% complementary to at least one other target sequence in the sample. In some examples, amplification can be performed using multiple target-specific primer pairs in a single amplification reaction, wherein each primer pair includes a forward target-specific primer and a reverse target-specific primer, each including at least one sequence that substantially complementary or substantially identical to a corresponding target sequence in the sample, and each primer pair having a different corresponding target sequence. In some examples, the target-specific primer can be substantially non-complementary at its 3' end or its 5' end to any other target-specific primer present in an amplification reaction. In some examples, the target-specific primer can include minimal cross hybridization to other target-specific primers in the amplification reaction. In some examples, target-specific primers include minimal cross-hybridization to non-specific sequences in the amplification reaction mixture. In some examples, the target-specific primers include minimal self-complementarity. In some examples, the target-specific primers can include one or more cleavable groups located at the 3' end. In some examples, the target-specific primers can include one or more cleavable groups located near or about a central nucleotide of the target-specific primer. In some examples, one of more targets-specific primers includes only non-cleavable nucleotides at the 5' end of the target-specific primer. In some examples, a target specific primer includes minimal nucleotide sequence overlap at the 3' end or the 5' end of the primer as compared to one or more different target-specific primers, optionally in the same amplification reaction. In some examples 1, 2, 3, 4, 5, 6, 7, 8, 9, 10 or more, target-specific primers in a single reaction mixture include one or more of the above examples. In some examples, substantially all of the plurality of target-specific primers in a single reaction mixture includes one or more of the above examples.

As used herein, the term "adaptor" denotes a nucleic acid molecule that can be used for manipulation of a polynucleotide of interest. In some examples, adaptors are used for amplification of one or more target nucleic acids. In some examples, the adaptors are used in reactions for sequencing. In some examples, an adaptor has one or more ends that lack a 5' phosphate residue. In some examples, an adaptor comprises, consists of, or consist essentially of at least one priming site. Such priming site containing adaptors can be referred to as "primer" adaptors. In some examples, the adaptor priming site can be useful in PCR processes. In some examples an adaptor includes a nucleic acid sequence that is substantially complementary to the 3' end or the 5' end of at least one target sequences within the sample, referred to herein as a gene specific target sequence, a target specific sequence, or target specific primer. In some examples, the adaptor includes nucleic acid sequence that is substantially non-complementary to the 3' end or the 5' end of any target sequence present in the sample. In some examples, the adaptor includes single stranded or double-stranded linear oligonucleotide that is not substantially complementary to an target nucleic acid sequence. In some examples, the adaptor includes nucleic acid sequence that is substantially non-complementary to at least one, and preferably some or all of the nucleic acid molecules of the sample. In some examples, suitable adaptor lengths are in the range of about 10-75 nucleotides, about 12-50 nucleotides and about 15-40 nucleotides in length. Generally, an adaptor can include any combination of nucleotides and/or nucleic acids. In some aspects, adaptors include one or more cleavable groups at one or more locations. In some examples, the adaptor includes sequence that is substantially identical, or substantially complementary, to at least a portion of a primer, for example a universal primer. In some examples, adaptors include a tag sequence to assist with cataloguing, identification or sequencing. In some examples, an adaptor acts as a substrate for amplification of a target sequence, particularly in the presence of a polymerase and dNTPs under suitable temperature and pH.

As used herein, "polymerase" and its derivatives, generally refers to any enzyme that can catalyze the polymerization of nucleotides (including analogs thereof) into a nucleic acid strand. Typically but not necessarily, such nucleotide polymerization can occur in a template-dependent fashion. Such polymerases can include without limitation naturally occurring polymerases and any subunits and truncations thereof, mutant polymerases, variant polymerases, recombinant, fusion or otherwise engineered polymerases, chemically modified polymerases, synthetic molecules or assemblies, and any analogs, derivatives or fragments thereof that retain the ability to catalyze such polymerization. Optionally, the polymerase can be a mutant polymerase comprising one or more mutations involving the replacement of one or more amino acids with other amino acids, the insertion or deletion of one or more amino acids from the polymerase, or the linkage of parts of two or more polymerases. Typically, the polymerase comprises one or more active sites at which nucleotide binding and/or catalysis of nucleotide polymerization can occur. Some exemplary polymerases include without limitation DNA polymerases and RNA polymerases. The term "polymerase" and its variants, as used herein, also refers to fusion proteins comprising at least two portions linked to each other, where the first portion comprises a peptide that can catalyze the polymerization of nucleotides into a nucleic acid strand and is linked to a second portion that comprises a second polypeptide. In some examples, the second polypeptide can include a reporter enzyme or a processivity-enhancing domain. Optionally, the polymerase can possess 5' exonuclease activity or terminal transferase activity. In some examples, the polymerase can be optionally reactivated, for example through the use of heat, chemicals or re-addition of new amounts of polymerase into a reaction mixture. In some examples, the polymerase can include a hot-start polymerase and/or an aptamer based polymerase that optionally can be reactivated.

The terms "identity" and "identical" and their variants, as used herein, when used in reference to two or more nucleic acid sequences, refer to similarity in sequence of the two or more sequences (e.g., nucleotide or polypeptide sequences). In the context of two or more homologous sequences, the percent identity or homology of the sequences or subsequences thereof indicates the percentage of all monomeric units (e.g., nucleotides or amino acids) that are the same (i.e., about 70% identity, preferably 75%, 80%, 85%, 90%, 95%, 98% or 99% identity). The percent identity can be over a specified region, when compared and aligned for maximum correspondence over a comparison window, or designated region as measured using a BLAST or BLAST 2.0 sequence comparison algorithms with default parameters described below, or by manual alignment and visual inspection. Sequences are said to be "substantially identical" when there is at least 85% identity at the amino acid level or at the nucleotide level. Preferably, the identity exists over a region that is at least about 25, 50, or 100 residues in length, or across the entire length of at least one compared sequence. A typical algorithm for determining percent sequence identity and sequence similarity are the BLAST and BLAST 2.0 algorithms, which are described in Altschul et al, Nuc. Acids Res. 25:3389-3402 (1997). Other methods include the algorithms of Smith & Waterman, Adv. Appl. Math. 2:482 (1981), and Needleman & Wunsch, J. Mol. Biol. 48:443 (1970), etc. Another indication that two nucleic acid sequences are substantially identical is that the two molecules or their complements hybridize to each other under stringent hybridization conditions.

The terms "complementary" and "complement" and their variants, as used herein, refer to any two or more nucleic acid sequences (e.g., portions or entireties of template nucleic acid molecules, target sequences and/or primers) that can undergo cumulative base pairing at two or more individual corresponding positions in antiparallel orientation, as in a hybridized duplex. Such base pairing can proceed according to any set of established rules, for example according to Watson-Crick base pairing rules or according to some other base pairing paradigm. Optionally there can be "complete" or "total" complementarity between a first and second nucleic acid sequence where each nucleotide in the first nucleic acid sequence can undergo a stabilizing base pairing interaction with a nucleotide in the corresponding antiparallel position on the second nucleic acid sequence. "Partial" complementarity describes nucleic acid sequences in which at least 20%, but less than 100%, of the residues of one nucleic acid sequence are complementary to residues in the other nucleic acid sequence. In some examples, at least 50%, but less than 100%, of the residues of one nucleic acid sequence are complementary to residues in the other nucleic acid sequence. In some examples, at least 70%, 80%, 90%, 95% or 98%, but less than 100%, of the residues of one nucleic acid sequence are complementary to residues in the other nucleic acid sequence. Sequences are said to be "substantially complementary" when at least 85% of the residues of one nucleic acid sequence are complementary to residues in the other nucleic acid sequence. In some examples, two complementary or substantially complementary sequences are capable of hybridizing to each other under standard or stringent hybridization conditions. "Non-complementary" describes nucleic acid sequences in which less than 20% of the residues of one nucleic acid sequence are complementary to residues in the other nucleic acid sequence. Sequences are said to be "substantially non-complementary" when less than 15% of the residues of one nucleic acid sequence are complementary to residues in the other nucleic acid sequence. In some examples, two non-complementary or substantially non-complementary sequences cannot hybridize to each other under standard or stringent hybridization conditions. A "mismatch" is present at any position in the two opposed nucleotides are not complementary. Complementary nucleotides include nucleotides that are efficiently incorporated by DNA polymerases opposite each other during DNA replication under physiological conditions. In a typical example, complementary nucleotides can form base pairs with each other, such as the A-T/U and G-C base pairs formed through specific Watson-Crick type hydrogen bonding, or base pairs formed through some other type of base pairing paradigm, between the nucleobases of nucleotides and/or polynucleotides in positions antiparallel to each other. The complementarity of other artificial base pairs can be based on other types of hydrogen bonding and/or hydrophobicity of bases and/or shape complementarity between bases.

As used herein, "amplified target sequences" and its derivatives, refers generally to a nucleic acid sequence produced by the amplification of/amplifying the target sequences using target-specific primers and the methods provided herein. The amplified target sequences may be either of the same sense (the positive strand produced in the second round and subsequent even-numbered rounds of amplification) or antisense (i.e., the negative strand produced during the first and subsequent odd-numbered rounds of amplification) with respect to the target sequences. For the purposes of this disclosure, amplified target sequences are typically less than 50% complementary to any portion of another amplified target sequence in the reaction.

As used herein, terms "ligating", "ligation" and derivatives refer generally to the act or process for covalently linking two or more molecules together, for example, covalently linking two or more nucleic acid molecules to each other. In some examples, ligation includes joining nicks between adjacent nucleotides of nucleic acids. In some examples, ligation includes forming a covalent bond between an end of a first and an end of a second nucleic acid molecule. In some examples, for example examples wherein the nucleic acid molecules to be ligated include conventional nucleotide residues, the ligation can include forming a covalent bond between a 5' phosphate group of one nucleic acid and a 3' hydroxyl group of a second nucleic acid thereby forming a ligated nucleic acid molecule. In some examples, any means for joining nicks or bonding a 5' phosphate to a 3' hydroxyl between adjacent nucleotides can be employed. In an exemplary example, an enzyme such as a ligase can be used.

As used herein, "ligase" and its derivatives, refers generally to any agent capable of catalyzing the ligation of two substrate molecules. In some examples, the ligase includes an enzyme capable of catalyzing the joining of nicks between adjacent nucleotides of a nucleic acid. In some examples, a ligase includes an enzyme capable of catalyzing the formation of a covalent bond between a 5' phosphate of one nucleic acid molecule to a 3' hydroxyl of another nucleic acid molecule thereby forming a ligated nucleic acid molecule. Suitable ligases may include, but not limited to, T4 DNA ligase; T7 DNA ligase; Taq DNA ligase, and *E. coli* DNA ligase.

As defined herein, a "cleavable group" generally refers to any moiety that once incorporated into a nucleic acid can be cleaved under appropriate conditions. For example, a cleavable group can be incorporated into a target-specific primer, an amplified sequence, an adaptor or a nucleic acid molecule of the sample. In an exemplary example, a target-specific primer can include a cleavable group that becomes incorporated into the amplified product and is subsequently cleaved after amplification, thereby removing a portion, or all, of the target-specific primer from the amplified product. The cleavable group can be cleaved or otherwise removed from a target-specific primer, an amplified sequence, an adaptor or a nucleic acid molecule of the sample by any acceptable means. For example, a cleavable group can be removed from a target-specific primer, an amplified sequence, an adaptor or a nucleic acid molecule of the sample by enzymatic, thermal, photo-oxidative or chemical treatment. In one aspect, a cleavable group can include a nucleobase that is not naturally occurring. For example, an oligodeoxyribonucleotide can include one or more RNA nucleobases, such as uracil that can be removed by a uracil glycosylase. In some examples, a cleavable group can include one or more modified nucleobases (such as 7-methylguanine, 8-oxo-guanine, xanthine, hypoxanthine, 5,6-dihydrouracil or 5-methylcytosine) or one or more modified nucleosides (i.e., 7-methylguanosine, 8-oxo-deoxyguanosine, xanthosine, inosine, dihydrouridine or 5-methylcytidine). The modified nucleobases or nucleotides can be removed from the nucleic acid by enzymatic, chemical or thermal means. In one example, a cleavable group can include a moiety that can be removed from a primer after amplification (or synthesis) upon exposure to ultraviolet light (i.e., bromodeoxyuridine). In another example, a cleavable group can include methylated cytosine. Typically, methylated cytosine can be cleaved from a primer for example, after induction of amplification (or synthesis), upon sodium bisulfite treatment. In some examples, a cleavable moiety can include a restriction site. For example, a primer or target sequence can include a nucleic acid sequence that is specific to one or more restriction enzymes, and following amplification (or synthesis), the primer or target sequence can be treated with the one or more restriction enzymes such that the cleavable group is removed. Typically, one or more cleavable groups can be included at one or more locations with a target-specific primer, an amplified sequence, an adaptor or a nucleic acid molecule of the sample.

As used herein, "digestion", "digestion step" and its derivatives, generally refers to any process by which a cleavable group is cleaved or otherwise removed from a target-specific primer, an amplified sequence, an adaptor or a nucleic acid molecule of the sample. In some examples, the digestion step involves a chemical, thermal, photo-oxidative or digestive process.

As used herein, the term "hybridization" is consistent with its use in the art, and generally refers to the process whereby two nucleic acid molecules undergo base pairing interactions. Two nucleic acid molecule molecules are said to be hybridized when any portion of one nucleic acid molecule is base paired with any portion of the other nucleic acid molecule; it is not necessarily required that the two nucleic acid molecules be hybridized across their entire respective lengths and in some examples, at least one of the nucleic acid molecules can include portions that are not hybridized to the other nucleic acid molecule. The phrase "hybridizing under stringent conditions" and its variants refers generally to conditions under which hybridization of a target-specific primer to a target sequence occurs in the presence of high hybridization temperature and low ionic strength. As used herein, the phrase "standard hybridization conditions" and its variants refers generally to conditions under which hybridization of a primer to an oligonucleotide (i.e., a target sequence), occurs in the presence of low hybridization temperature and high ionic strength. In one exemplary example, standard hybridization conditions include an aqueous environment containing about 100 mm magnesium sulfate, about 500 mM Tris-sulfate at pH 8.9, and about 200 mM ammonium sulfate at about 50-55° C., or equivalents thereof.

As used herein, the term "end" and its variants, when used in reference to a nucleic acid molecule, for example a target sequence or amplified target sequence, can include the terminal 30 nucleotides, the terminal 20 and even more typically the terminal 15 nucleotides of the nucleic acid molecule. A linear nucleic acid molecule comprised of linked series of contiguous nucleotides typically includes at least two ends. In some examples, one end of the nucleic acid molecule can include a 3' hydroxyl group or its equivalent, and can be referred to as the "3' end" and its derivatives. Optionally, the 3' end includes a 3' hydroxyl group that is not linked to a 5' phosphate group of a mononucleotide pentose ring. Typically, the 3' end includes one or more 5' linked nucleotides located adjacent to the nucleotide including the unlinked 3' hydroxyl group, typically the 30 nucleotides located adjacent to the 3' hydroxyl, typically the terminal 20 and even more typically the terminal 15 nucleotides. Generally, the one or more linked nucleotides can be represented as a percentage of the nucleotides present in the oligonucleotide or can be provided as a number of linked nucleotides adjacent to the unlinked 3' hydroxyl. For example, the 3' end can include less than 50% of the nucleotide length of the oligonucleotide. In some examples, the 3' end does not include any unlinked 3' hydroxyl group but can include any moiety capable of serving as a site for attachment of nucleotides via primer extension and/or nucleotide polymerization. In some examples, the term "3' end" for example when referring to a target-specific primer, can include the terminal 10 nucleotides, the terminal 5 nucleotides, the terminal 4, 3, 2 or fewer nucleotides at the 3' end. In some examples, the term "3' end" when referring to a target-specific primer can include nucleotides located at nucleotide positions 10 or fewer from the 3' terminus. As used herein, "5' end", and its derivatives, generally refers to an end of a nucleic acid molecule, for example a target sequence or amplified target sequence, which includes a free 5' phosphate group or its equivalent. In some examples, the 5' end includes a 5' phosphate group that is not linked to a 3' hydroxyl of a neighboring mononucleotide pentose ring. Typically, the 5' end includes to one or more linked nucleotides located adjacent to the 5' phosphate, typically the 30 nucleotides located adjacent to the nucleotide including the 5' phosphate group, typically the terminal 20 and even more typically the terminal 15 nucleotides. Generally, the one or more linked nucleotides can be represented as a percentage of the nucleotides present in the oligonucleotide or can be provided as a number of linked nucleotides adjacent to the 5' phosphate. For example, the 5' end can be less than 50% of the nucleotide length of an oligonucleotide. In another exemplary example, the 5' end can include about 15 nucleotides adjacent to the nucleotide including the terminal 5' phosphate. In some examples, the 5' end does not include any unlinked 5' phosphate group but can include any moiety capable of serving as a site of attachment to a 3' hydroxyl group, or to the 3' end of another nucleic acid molecule. In some examples, the term "5' end" for example when referring to a target-specific primer, can include the terminal 10 nucleotides, the terminal 5 nucleotides, the terminal 4, 3, 2 or fewer nucleotides at the 5' end. In some examples, the term "5' end" when referring to a target-specific primer can include nucleotides located at positions 10 or fewer from the 5' terminus. In some examples, the 5' end of a target-specific primer can include only non-cleavable nucleotides, for example nucleotides that do not contain one or more cleavable groups as disclosed herein, or a cleavable nucleotide as would be readily determined by one of ordinary skill in the art. A "first end" and a "second end" of a polynucleotide refer to the 5' end or the 3' end of the polynucleotide. Either the first end or second end of a polynucleotide can be the 5' end or the 3' end of the polynucleotide; the terms "first" and "second" are not meant to denote that the end is specifically the 5' end or the 3' end.

As used herein "tag," "barcode," "unique tag" or "tag sequence" and its derivatives, refers generally to a unique short (6-14 nucleotide) nucleic acid sequence within an adaptor or primer that can act as a 'key' to distinguish or separate a plurality of amplified target sequences in a sample. For the purposes of this disclosure, a barcode or unique tag sequence is incorporated into the nucleotide sequence of an adaptor or primer. As used herein, "barcode sequence" denotes a nucleic acid fixed sequence that is sufficient to allow for the identification of a sample or source of nucleic acid sequences of interest. A barcode sequence can be, but need not be, a small section of the original nucleic acid sequence on which the identification is to be based. In some examples a barcode is 5-20 nucleic acids long. In some examples, the barcode is comprised of analog nucleotides, such as L-DNA, LNA, PNA, etc. As used herein, "unique tag sequence" denotes a nucleic acid sequence having at least one random sequence and at least one fixed sequence. A unique tag sequence, alone or in conjunction with a second unique tag sequence, is sufficient to allow for the identification of a single target nucleic acid molecule in a sample. A unique tag sequence can, but need not, comprise a small section of the original target nucleic acid sequence. In some examples a unique tag sequence is 2-50 nucleotides or base-pairs, or 2-25 nucleotides or base-pairs, or 2-10 nucleotides or base-pairs in length. A unique tag sequence can comprise at least one random sequence interspersed with a fixed sequence.

As used herein, "comparable maximal minimum melting temperatures" and its derivatives, refers generally to the melting temperature (Tm) of each nucleic acid fragment for a single adaptor or target-specific primer after digestion of a cleavable groups. The hybridization temperature of each nucleic acid fragment generated by an adaptor or target-specific primer is compared to determine the maximal minimum temperature required preventing hybridization of a nucleic acid sequence from the target-specific primer or adaptor or fragment or portion thereof to a respective target sequence. Once the maximal hybridization temperature is known, it is possible to manipulate the adaptor or target-specific primer, for example by moving the location of one or more cleavable group(s) along the length of the primer, to achieve a comparable maximal minimum melting temperature with respect to each nucleic acid fragment to thereby optimize digestion and repair steps of library preparation.

As used herein, "addition only" and its derivatives, refers generally to a series of steps in which reagents and components are added to a first or single reaction mixture. Typically, the series of steps excludes the removal of the reaction mixture from a first vessel to a second vessel in order to complete the series of steps. Generally, an addition only process excludes the manipulation of the reaction mixture outside the vessel containing the reaction mixture. Typically, an addition-only process is amenable to automation and high-throughput.

As used herein, "polymerizing conditions" and its derivatives, refers generally to conditions suitable for nucleotide polymerization. In typical examples, such nucleotide polymerization is catalyzed by a polymerase. In some examples, polymerizing conditions include conditions for primer extension, optionally in a template-dependent manner, resulting in the generation of a synthesized nucleic acid sequence. In some examples, the polymerizing conditions include polymerase chain reaction (PCR). Typically, the polymerizing conditions include use of a reaction mixture that is sufficient to synthesize nucleic acids and includes a polymerase and nucleotides. The polymerizing conditions can include conditions for annealing of a target-specific primer to a target sequence and extension of the primer in a template dependent manner in the presence of a polymerase. In some examples, polymerizing conditions can be practiced using thermocycling. Additionally, polymerizing conditions can include a plurality of cycles where the steps of annealing, extending, and separating the two nucleic strands are repeated. Typically, the polymerizing conditions include a cation such as $MgCl_2$. Generally, polymerization of one or more nucleotides to form a nucleic acid strand includes that the nucleotides be linked to each other via phosphodiester bonds, however, alternative linkages may be possible in the context of particular nucleotide analogs.

As used herein, the term "nucleic acid" refers to natural nucleic acids, artificial nucleic acids, analogs thereof, or combinations thereof, including polynucleotides and oligonucleotides. As used herein, the terms "polynucleotide" and "oligonucleotide" are used interchangeably and mean single-stranded and double-stranded polymers of nucleotides including, but not limited to, 2'-deoxyribonucleotides (nucleic acid) and ribonucleotides (RNA) linked by internucleotide phosphodiester bond linkages, e.g. 3'-5' and 2'-5', inverted linkages, e.g. 3'-3' and 5'-5', branched structures, or analog nucleic acids. Polynucleotides have associated counter ions, such as H+, NH4+, trialkylammonium, Mg2+, Na+ and the like. An oligonucleotide can be composed entirely of deoxyribonucleo tides, entirely of ribonucleotides, or chimeric mixtures thereof. Oligonucleotides can be comprised of nucleobase and sugar analogs. Polynucleotides typically range in size from a few monomeric units, e.g. 5-40, when they are more commonly frequently referred to in the art as oligonucleotides, to several thousands of monomeric nucleotide units, when they are more commonly referred to in the art as polynucleotides; for purposes of this disclosure, however, both oligonucleotides and polynucleotides may be of any suitable length. Unless denoted otherwise, whenever a oligonucleotide sequence is represented, it will be understood that the nucleotides are in 5' to 3' order from left to right and that "A" denotes deoxyadenosine, "C" denotes deoxycytidine, "G" denotes deoxyguanosine, "T" denotes thymidine, and "LP denotes deoxyuridine. As discussed herein and known in the art, oligonucleotides and polynucleotides are said to have "5' ends" and "3' ends" because mononucleotides are typically reacted to form oligonucleotides via attachment of the 5' phosphate or equivalent group of one nucleotide to the 3' hydroxyl or equivalent group of its neighboring nucleotide, optionally via a phosphodiester or other suitable linkage.

As used herein, the term "polymerase chain reaction" ("PCR") refers to the method of K. B. Mullis U.S. Pat. Nos. 4,683,195 and 4,683,202, hereby incorporated by reference, which describe a method for increasing the concentration of a segment of a polynucleotide of interest in a mixture of genomic DNA without cloning or purification. This process for amplifying the polynucleotide of interest consists of introducing a large excess of two oligonucleotide primers to the DNA mixture containing the desired polynucleotide of interest, followed by a precise sequence of thermal cycling in the presence of a DNA polymerase. The two primers are complementary to their respective strands of the double stranded polynucleotide of interest. To effect amplification, the mixture is denatured and the primers then annealed to their complementary sequences within the polynucleotide of interest molecule. Following annealing, the primers are extended with a polymerase to form a new pair of complementary strands. The steps of denaturation, primer annealing and polymerase extension can be repeated many times (i.e., denaturation, annealing and extension constitute one "cycle"; there can be numerous "cycles") to obtain a high concentration of an amplified segment of the desired polynucleotide of interest. The length of the amplified segment of the desired polynucleotide of interest (amplicon) is determined by the relative positions of the primers with respect to each other, and therefore, this length is a controllable parameter. By virtue of repeating the process, the method is referred to as the "polymerase chain reaction" (hereinafter "PCR"). Because the desired amplified segments of the polynucleotide of interest become the predominant nucleic acid sequences (in terms of concentration) in the mixture, they are said to be "PCR amplified". As defined herein, target nucleic acid molecules within a sample including a plurality of target nucleic acid molecules are amplified via PCR. In a modification to the method discussed above, the target nucleic acid molecules can be PCR amplified using a plurality of different primer pairs, in some cases, one or more primer pairs per target nucleic acid molecule of interest, thereby forming a multiplex PCR reaction. Using multiplex PCR, it is possible to simultaneously amplify multiple nucleic acid molecules of interest from a sample to form amplified target sequences. It is also possible to detect the amplified target sequences by several different methodologies (e.g., quantitation with a bioanalyzer or qPCR, hybridization with a labeled probe; incorporation of biotinylated primers followed by avidin-enzyme conjugate detection; incorporation of 32P-labeled deoxynucleotide triphosphates, such as dCTP or dATP, into the amplified target sequence). Any oligonucleotide sequence can be amplified with the appropriate set of primers, thereby allowing for the amplification of target nucleic acid molecules from genomic DNA, cDNA, formalin-fixed paraffin-embedded DNA, fine-needle biopsies and various other sources. In particular, the amplified target sequences created by the multiplex PCR process as disclosed herein, are themselves efficient substrates for subsequent PCR amplification or various downstream assays or manipulations.

As defined herein "multiplex amplification" refers to selective and non-random amplification of two or more target sequences within a sample using at least one target-specific primer. In some examples, multiplex amplification is performed such that some or all of the target sequences are amplified within a single reaction vessel. The "plexy" or "plex" of a given multiplex amplification refers generally to the number of different target-specific sequences that are amplified during that single multiplex amplification. In some examples, the plexy can be about 12-plex, 24-plex, 48-plex, 96-plex, 192-plex, 384-plex, 768-plex, 1536-plex, 3072-plex, 6144-plex or higher.

Methods for Making Libraries with or without UMI

The methods and compositions described herein may include procedures that allow preparation of multiplexed, UMI-containing libraries suitable for massive parallel sequencing and downstream analysis. The methods described herein may comprise procedures that can also be utilized for the purpose of amplifying a plurality of DNA targets. The methods optionally allow for incorporation of one or more UMI sequences; or for incorporation of hybridization capture, deoxyuridine-containing nucleotide, etc., if so desired. Certain methods comprise streamlined and use-friendly workflows.

In one example, methods for preparing a UMI-containing library of target nucleic acid sequences are provided. In some examples, methods comprise removing the 3' protruding ends and phosphorylating the 5' ends of the DNA fragments; ligating A DNA adapter to the ends of the DNA fragments on both sides; amplifying the DNA fragments with a universal primer in PCR; annealing and extending a panel of target-specific primers onto the amplified DNA fragments; enzymatically removing the single stranded regions as well as the remaining primers and primer-dimers; further amplifying the target DNA molecules with a second PCR with a pair of universal primers. The DNA adapter used in the methods herein comprises a UMI region and a universal primer region. Each of the target-specific primers of the panel comprises a target specific region, a UMI region and a second universal primer region, wherein at least two and up to one hundred thousand target specific primers are included, and wherein the target specific primers are forward, or reverse, or both forward and reverse PCR primers. The pair of universal primers comprises sample indexes and sequencing primers that are simultaneously added onto the DNA targets during the second PCR. The finished library is ready for massive parallel sequencing.

In certain examples, the DNA adapter used in the methods herein comprises a universal primer region. The primary clones are formed and identified by the nucleotide sequences and the length of the DNA molecules.

In some examples, the DNA adapter used in the methods herein comprises a universal primer region, a sample barcode, and a UMI region, multiple samples with different sample barcodes are pooled after adapter ligation, and a hybridization capture of target molecules by a pool of target-specific oligos is applied following the pooling of samples. The methods comprise removing the 3' protruding ends and phosphorylating the 5' ends of the DNA fragments; ligating A DNA adapter to the ends of the DNA fragments on both sides; pooling multiple samples with different sample barcodes; amplifying the DNA fragments with a universal primer in PCR; enriching the target molecules by hybridization capture with a pool of target-specific oligos; annealing and extending a panel of target-specific primers onto the amplified DNA fragments; enzymatically removing the single stranded regions as well as the remaining primers and primer-dimers; further amplifying the target DNA molecules with a second PCR with a pair of universal primers. Each of the target-specific primers of the panel comprises a target specific region, a UMI region and a second universal primer region, wherein at least two and up to one hundred thousand target specific primers are included, and wherein the target specific primers are forward, or reverse, or both forward and reverse PCR primers. The pair of universal primers comprises sample indexes and sequencing primers that are simultaneously added onto the DNA targets during the second PCR. The finished library is ready for massive parallel sequencing.

In one examples, a deoxyuridine-containing universal primer is used to amplify DNA fragments after adapter ligation. The methods comprise removing the 3' protruding ends and phosphorylating the 5' ends of the DNA fragments; ligating A DNA adapter to the ends of the DNA fragments on both sides; amplifying the DNA fragments with a deoxyuridine-containing universal primer in PCR; annealing and extending a panel of target-specific primers onto the amplified DNA fragments; enzymatically cleaving the Us in the resulting structures by uracil DNA glycosylase and apurinic/apyrimidinic endonuclease; further amplifying the target DNA molecules with a second PCR with a pair of universal primers. The DNA adapter used in the methods herein comprises a UMI region and a universal primer region. Each of the target-specific primers of the panel comprises a target specific region, a UMI region and a second universal primer region, wherein at least two and up to one hundred thousand target specific primers are included, and wherein the target specific primers are forward, or reverse, or both forward and reverse PCR primers. The pair of universal primers comprises sample indexes and sequencing primers that are simultaneously added onto the DNA targets during the second PCR. The finished library is ready for massive parallel sequencing.

In certain examples, the methods described herein may include procedures that are utilized for the purpose of amplifying a plurality of DNA targets. The methods comprise removing the 3' protruding ends and phosphorylating the 5' ends of the DNA fragments; ligating A DNA adapter to the ends of the DNA fragments on both sides; amplifying the DNA fragments with a universal primer in PCR; annealing and extending a panel of target-specific primers onto the amplified DNA fragments; enzymatically removing the single stranded regions as well as the remaining primers and primer-dimers; and optionally further amplifying the target DNA molecules with a second PCR with a pair of universal primers. The DNA adapter comprises a universal primer region, and optionally a UMI region. Each of the target-specific primers comprises a target specific region, a second universal primer region and optionally a UMI region, wherein at least two and up to one hundred thousand target specific primers are included, and wherein the target specific primers are forward, or reverse, or both forward and reverse PCR primers. Additionally optionally, the single stranded regions in the resulting structures, as well as the remaining primers and primer-dimers, are then reduced or removed enzymatically. The target DNA molecules are optionally amplified by a second PCR with a pair of universal primers.

In some examples, the DNA adapter used in the methods herein comprises a universal primer region, a sample barcode, and a UMI region. Multiple samples with different sample barcodes are pooled after adapter ligation, and a hybridization capture of target molecules by a pool of target-specific oligos is applied following the pooling of samples.

In one example, a deoxyuridine-containing universal primer is used to amplify DNA fragments after adapter ligation. Uracil DNA glycosylase and apurinic/apyrimidinic endonuclease are utilized to cleave the resulting structures after annealing and extending a panel of target-specific primers onto the DNA targets.

In some examples, many methods and strategies of adapter design and ligation reactions are utilized in the methods described herein. These methods and strategies include, but not limited to, ligating a single-stranded UMI-containing DNA adapter to the 5' ends of the DNA molecules, ligating a double-stranded UMI-containing DNA adapter to the both ends of the DNA molecules, ligating a single-stranded UMI-containing DNA adapter to the 3' ends of the DNA molecules. In some examples, the above mentioned single-stranded UMI-containing DNA adapter contains a stretch of RNA, modifications at 5' and/or 3' end, a complementary region of UMI, or a non-complementary region of UMI. The above examples do not intend to exhaust the possibilities of the methods and strategies of adapter design and ligation reactions. There may exist an unlimited number of methods to attach a UMI-containing adapter to the target DNA molecules. But they all fall within the concept of forming primary UMI clones and subdividing each primary UMI clone into subclones, or forming a two-dimensional matrix.

Many other examples of the concepts of SubDivision Seq are possible. These may include, but not limited to, using a panel of forward target specific primers, or a panel of both forward and reverse target specific primers, using various adapters, using various combinations of PCR and hybridization capture, switching a region of nucleotide sequence through utilizing U-containing primer and enzymatic manipulations, etc. It is almost impossible to exhaust the number and the types of these variations in details and in depictions. All of these examples, through various designs and technical approaches, materialize the concept of dividing a primary UMI clone (or UMI cluster) derived from a double-stranded DNA molecule or a single-stranded DNA molecule into multiplex UMI subclones (or subclusters).

In some examples, the large (Klenow) fragment of DNA polymerase I (NEB M0210L) is used to make blunt ends, and T4 Polynucleotide Kinase (NEB M0201L) is used to phosphorylate the 5' ends of the DNA fragments in the end repair reactions. In some examples, 1× Ligation buffer (50 mM Tris-HCl, pH7.5, 10 mM $MgCl_2$, 0.5 mM ATP, 5 mM DTT) is used in the end repair reactions. Blunting ends and phosphorylation reactions may be done sequentially, or combined in a single reaction. Klenow fragment of DNA polymerase I may introduce base errors at the ends of DNA fragments. In some examples, exonuclease VII (NEB M0379L) is used to shorten the 5' and 3' overhang to ≤7 nucleotides, then T4 DNA polymerase (NEB M0203L) is used to blunt both ends in the presence of dNTP. In some examples, exonuclease T (Also known as RNase T, NEB M0265L) is used to remove 3' protruding ends to avoid the base errors introduced by Klenow fragment. In this case, a single stranded adapter is ligated to the resulting 5' blunt ends and the preexisting 5' protruding ends of the DNA fragments. In some examples, mung bean nuclease (NEB M0250L), the buffers and the conditions suggested by the supplier are used to make blunt ends. In some examples, the end repair reactions are incubated at 25° C. for 40 minutes and the enzymes are subsequently inactivated at 65° C. for 20 minutes. In some examples, the damaged bases are repair simultaneously by a cocktail of enzymes, which include but not limited to endonuclease IV (NEB M0304S), formamidopyrimidine [fapy]-DNA glycosylase (NEB M0240S), uracil-DNA glycosylase (NEB M0280S), T4 pyrimidine DNA glycosylase (NEB M0308S) and endonuclease VIII (NEB M0299S).

In some examples, a single stranded DNA adapter is ligated to the DNA fragments. In some examples, the single stranded DNA adapter comprises a universal primer region, a UMI region, and a short stretch of RNA. In some cases, the UMI region comprises 16 random bases and the short stretch of RNA comprises four ribonucleotides, such as rArArArA. In some cases, the UMI region comprises 12 random bases and the short stretch of RNA comprises four random ribonucleotides, such as rNrNrNrN. T4 RNA Ligase 1 (NEB M0204L) is used to ligate the single stranded DNA adapter to the 5' blunt ends and the preexisting 5' protruding ends of the DNA fragments. In some examples, the adapter and T4 RNA Ligase 1 are added to the end repair reactions. In some cases, the resulting ligation reaction is supplemented with 20-30% PEG3000, or 20-30% PEG6000, or 20-30% PEG8000. In some cases, the resulting ligation reaction is additionally supplemented with 0.1~1 mM ATP. In some cases, the ligation reaction is incubated at 37° C. for 2 hours, or at 37° C. for 4 hours, or at 37° C. for 8 hours, or at 37° C. for 16 hours, or at 37° C. for 24 hours. In some cases, the enzymes in the ligation reaction are subsequently inactivated at 65° C. for 20 minutes.

In some examples, the remaining single stranded DNA adapters in the ligation reaction are removed after the ligation reaction. In some cases, exonuclease T is used to digest the remaining single stranded DNA adapters by incubating at 25° C. for 40 minutes and 65° C. for 20 minutes.

In some examples, the DNA fragments are amplified with a universal primer in PCR after the ligation. In some cases, the universal primer contains one deoxyuridine, or two deoxyuridines, or three deoxyuridines, or four deoxyuridines. These deoxyuridines replace the pre-existing deoxythymidines. In some cases, the universal primer does not contain deoxyuridine. Before starting the PCR, the 3' recessive ends of the DNA fragments are extended by a DNA polymerase. In some cases, a non-hot-start Taq polymerase is used to extend the 3' recessive ends over the short stretch of RNA on the template strand. Other kinds of thermophilic DNA polymerase may not be able to use the short stretch of RNA as template for DNA synthesis. The extension of the 3' recessive ends should be done prior to the start of PCR, where double stranded DNA fragments are denatured and the hot-start Taq DNA polymerase is activated. In some cases, the initial extension reaction comprises an incubation at 65° C. for 10 min with a non-hot-start Taq polymerase, then a PCR of 5~20 cycles follows.

In some examples, one cycle of PCR is used to extend a panel of target specific primers that are annealed to the amplified DNA fragments. In some cases, a hot-start Taq polymerase is used. In some cases, a panel of forward target specific primers, or a panel of reverse target specific primers, a panel of forward and reverse target specific primers, is used. Each target specific primer of the panel may optionally contain a UMI region. In some cases, the UMI region comprises 2, or 3, or 4, or up to 16 random bases.

In some examples, the target-specific primers may comprise any appropriate plurality of primers or pairs of primers, such as 5 primers or pairs of primers or more (e.g., at least 5 primers or pairs of primers) of target-specific primers, such as 10 primers or pairs of primers or more (e.g., at least 10 primers or pairs of primers) of target-specific primers, between 5 and 100,000 primers or pairs of primers, between 5 and 1000 primers or pairs of primers, between 1,000 to 100,000 primers or pairs of primers, over 100,000 primers or pairs of primers of target-specific primers, etc., between 10 and 100,000 primers or pairs of primers, between 10 and 1000 primers or pairs of primers, etc. Although five or more primers or pairs of primers are specified and may be preferable, less than five pairs may be used (e.g., two or more primers or pairs of primers, three or more primers or pairs of primers, four or more primers or pairs of primers, five or more primers or pairs of primers, or six or more primers or pairs of primers, may be used). The target-specific primers may also comprise any appropriate plurality of primers plus any appropriate plurality of pairs of primers, such as 5 primers plus 5 pairs of primers.

In some examples, the types of primers that may be used may include unmodified oligonucleotides, modified oligonucleotides, peptide nucleic acid (PNA); modified primers may contain one or more than one 5-methyl deoxycytidine and/or 2,6-diaminopurine, dideoxyinosine, dideoxyuridine, and biotin labeled oligonucleotides. One and/or both primers can contain barcodes or other sequences that allow for identification; one and/or both primers can contain adapter sequences.

In some examples, the single stranded regions and the single strand DNA fragments resulting from the annealing and extension of the panel are reduced or eliminated, thereby the non-target templates, non-specific products, and the remaining primers of the panel are rendered un-amplifiable in the optional downstream PCR. In the meanwhile, one of the primary UMI is also destroyed, making it possible for subdividing the primary UMI clones into multiple UMI subclones defined by the UMIs on the panel (FIGS. 8A-8D). In some cases, Exonuclease I (NEB M0293L) is used to reduce or eliminate the single stranded regions and the single strand DNA fragments. In some cases, 1~100 units of Exonuclease I are incubated in 1× Exonuclease I Reaction Buffer (67 mM Glycine-KOH pH 9.5, 6.7 mM $MgCl_2$, 10 mM β-ME) at 37° C. for 10~40 minutes.

In some examples, a dU containing universal primer is used to amplify the DNA fragments, after the annealing and extension of the panel of target specific primers, the non-target DNA fragments are rendered un-amplifiable by making breaks on the DNA chain at the sites of dUs. In some cases, 1~100 units of UDG (NEB M0280L) and 1~100 units of APE 1 (NEB M0282L) are incubated with DNA products at 37° C. for 20~40 minutes and 65° C. for 20 minutes.

In some examples the foregoing methods comprise digestion reagent selected from any one or a combination of T4 endonuclease VII, T7 endonuclease I, endonuclease I, endonuclease V, Nth endonuclease III, endonuclease VII, endonuclease VIII, UDG, apurinic endonuclease (e.g., APE1), RecJf, formamidopyrimidine [fapy]-DNA glycosylase (fpg), nuclease S1, nuclease P1, mung bean nuclease, nuclease CEL I, T4 DNA polymerase, T7 DNA polymerase, phi29 DNA polymerase. In some examples the foregoing methods comprise digestion reagent selected from any one or a combination of UDG, apurinic endonuclease (e.g., APE1) and fpg.

In the foregoing examples, one or more of the method steps is conducted in manual mode or in an automated mode or a combination thereof. In particular examples each of the method steps is carried out in automated mode. In some examples the foregoing methods further comprise at least one purification step. In particular examples a purification step is carried out only after the second PCR. In other particular examples a purification is carried out after the digestion step and an additional purification is carried out after the second PCR.

In some examples the hybridization capture uses a plurality of biotin-labeled target specific oligos for capturing with streptavidin-coupled magnetic beads. In some of the examples the single stranded DNA regions, the single stranded DNA fragments, and the primer-dimer byproducts are removed from the resulting library. In some of the examples the single stranded DNA regions, the single stranded DNA fragments, and the primer-dimer byproducts are reduced from the resulting library. In certain examples, the single stranded DNA regions, the single stranded DNA fragments, and the primer-dimer byproducts are eliminated.

In some examples, the foregoing methods further comprise analyzing the nucleotide sequence of the resulting targeted DNA library. Such analyzing comprises sequencing by traditional sequencing reactions, high throughput next generation sequencing, targeted multiplex array sequence detection, or any combination of two or more of the foregoing. In some examples, the foregoing methods further comprise deducing the consensus sequence from each UMI cluster of at least one target molecule in the sample. In other examples, the foregoing methods further comprise determining the abundance of at least one of the target nucleic acid sequences in the sample. In specific examples, the foregoing methods further comprise determining the low frequency allele(s) in a sample.

In some examples, the UMI-containing adapter additionally contains a universal prime site, which is used for the amplification of the target DNA molecules. The universal prime site is placed 5' to the UMI region, therefore the UMI is amplified into clones by PCR. This design allows low level of ctDNA (for example, 1-5 ng of cfDNA) to be amplified into levels of micrograms. Offering sufficient quantities of sample DNA through amplification improves the efficiencies of downstream DNA manipulations, as well as the sensitivity. In some examples, the universal primer may be an unmodified single-stranded DNA oligo, or a modified single-stranded DNA oligo. In some examples, the universal primer may contain deoxyuridines (dU) replacing dT. Cleavage of the single-stranded DNA at sites of dU helps render the non-target DNA molecules un-amplifiable, as well as removing the unused universal primers before amplifying the target-specific molecules. In some examples, single-stranded DNA containing dU are cleaved by uracil DNA glycosylase (UDG) and apurinic/apyrimidinic endonuclease (e.g., human APE 1). In some examples, dU sites on single-stranded DNA are cleaved by using UDG and formamidopyrimidine [fapy]-DNA glycosylase (fpg).

In some examples, the panel contains a plurality of target-specific primers (e.g., >6, >10, >100, >1000, >10,000, etc.), each of the primer may additionally contain a region that serves as UMI and a region that serves as a second universal primer site. The panel may comprise reverse PCR primers, or forward PCR primers, or a combination of both forward and reverse primers. The panel is used to anneal onto the amplified DNA molecules, followed by a single round of extension. Then single-stranded regions and molecules are removed by any one or a combination of the following enzymes: exonuclease I, exonuclease VII, UDG, APE I, fpg. In some examples, the resulting DNA molecules may be further amplified wherein sample barcodes and sequencing adapters are added. The final library may be used in downstream analysis, such as NGS sequencing.

In the methods described above, the amplification of the target is not limited by the length of the DNA fragments, and the requirement of the presence of two target-specific primer sites on a short DNA fragment is eliminated. Any targets, short and long, that harbor one primer site, are amplified. The methods, apparatuses (e.g., systems) and compositions described herein may allow for amplifying and detecting target signals with significantly higher sensitivity from a limited amount of starting material, such as cfDNA. Further, the methods, apparatuses and compositions described herein may allow for amplifying and detecting structural change of DNA, such as fusion genes.

In general, the target nucleic acids may comprise DNA or RNA, for example, genomic DNA or cDNA, DNA purified from Formalin-fixed, Paraffin-embedded (FFPE) tissue samples (FFPE DNA), cell-free DNA (cfDNA) or circulating tumor DNA (ctDNA).

In some examples, the methods provided herein can be used for amplifying a plurality of short DNA fragments and reducing the random base errors. These methods may involve a plurality of DNA primers or oligonucleotides. The methods disclosed herein provide for optimized protocols such that short DNA fragments are amplified and random base errors are eliminated or reduced. Overall, the methods can relate to improved methods of nucleic acid library preparation.

The methods as disclosed herein can further involve contacting the reaction with a 3'→5' single-stranded DNA specific exonuclease for cleaving single-stranded DNA regions and the primers. As used herein, the term "contacting" equates with introducing such enzyme to a pre-existing mixture as described herein. The methods of the present disclosure can use a variety of single-stranded DNA specific exonucleases that can recognize and cleave single-stranded DNA regions in 3'→5' direction. The plural form will be used herein to refer to enzymes that bind to and cleave aberrant DNA structures. The single-stranded DNA regions include, without limitation, branched DNAs, Y-structures, heteroduplex loops, single stranded overhangs, mismatches, and other kinds of non-perfectly-matched DNAs. In some examples, the single-stranded DNA specific nuclease can reduce the amount of single-stranded DNA regions in the amplification reaction without reducing the amount of target-specific amplification products that do not contain single-stranded DNA regions. In other examples, both single-stranded DNA regions and target-specific amplification products can be reduced. In some cases, the reaction can be substantially free of single-stranded DNA regions. Substantially free of single-stranded DNA regions can mean that the amount of single-stranded DNA regions in the amplification reaction have been reduced by greater than 50%, 60%, 70%, 80%, 85%, 90%, 91%, 92%, 93%, 94%, 95%, 96%, 97%, 98%, 99%, up to 100%.

Examples of 3'→5' single-stranded DNA specific exonucleases that can be utilized to cleave single-stranded DNA regions in the methods provided herein include, without limitation, exonuclease T, exonuclease I. It should be understood that essentially any 3'→5' single-stranded DNA specific exonuclease or its mutant that can perform the methods of the disclosure as described herein is envisioned.

In some examples, the methods can involve inactivating the 3'→5' single-stranded DNA specific exonuclease in the reaction by incubating the reaction at 72° C. for 30 min. In other cases, the 3'→5' single-stranded DNA specific exonuclease in the reaction is inactivated at 65-72° C. for 10-40 min.

In some examples, the methods as disclosed herein involves the purification of DNA before multiplex PCR. An example method of DNA purification involves DNA purification column, or precipitation by adding one tenth volume of sodium acetate and two-fold volume of pure ethanol. Another example method of DNA purification involves absorption of DNA onto magnetic or paramagnetic microbeads and elution afterwards.

In some examples, the amplification products described herein can be used to prepare libraries for next-generation sequencing. The common sequences in the primer pairs are identical to part of adapters useful for next-generation sequencing applications. The adapters can be sequencing adapters useful on a next-generation sequencing platform (e.g., Illumina TruSeq adapters). For example, the methods, compositions and apparatuses described herein may be useful for next-generation sequencing by the methods commercialized by Illumina, as described in U.S. Pat. No. 5,750,341 (Macevicz); U.S. Pat. No. 6,306,597 (Macevicz); and U.S. Pat. No. 5,969,119 (Macevicz).

Particular reference will now be made to specific aspects and figures of the disclosure. Such aspects are provided by way of example only. Numerous variations, changes, and substitutions will now occur to those skilled in the art without departing from the disclosure.

EXAMPLES

The following examples are given for the purpose of illustrating various examples of the invention and are not meant to limit the present invention in any fashion. The present examples, along with the methods described herein are presently representative of preferred examples, are exemplary, and are not intended as limitations on the scope of the invention. Changes therein and other uses which are encompassed within the spirit of the invention as defined by the scope of the claims will occur to those skilled in the art.

Example 1. Ligation of Adaptor to DNA Fragments

Reagents:

10× Ligation buffer (500 mM Tris-HCl, pH7.5, 100 mM MgCl2, 5 mM ATP, 50 mM DTT)

50 uM Single-stranded 5' adaptor with UMI (Table 1, SEQ IDs NO: 1-8)

50% PEG8000 in water

T4 RNA Ligase 1 (NEB M0204L)

RNase T (NEB M0265L)

End Repair Reaction:

Add the Following Mix to Make a 16 µl Reaction:

| | |
|---|---|
| dH2O | 6 µl |
| DNA sample | 6 µl |
| 10× Ligation buffer | 2 µl |
| T4 PNK enzyme | 1 µl |
| RNase T | 1 µl |

Incubate at 25° C. for 40 minutes and 65° C. for 20 minutes.

Adapter Ligation:

Add the Following Mix to Make a 40 µl Ligation Reaction:

| | |
|---|---|
| End repair reaction (above) | 16 µl |
| 10× Ligation buffer | 2 µl |
| 50 uM Adapter (RNA) | 4 µl |
| 50% PEG3000 | 16 µl |
| T4 RNA Ligase1 | 2 µl |

Incubate at 37° C. for 2 hours.

Clean-Up:

Add the Following Reagent:

| | |
|---|---|
| Ligation reaction (above) | 40 µl |
| RNase T | 2 µl |

Incubate at 25° C. for 40 minutes and 65° C. for 20 minutes.

Add 64 µl magnetic beads, incubate at room temperature for 15 minutes, wash twice with 70% ethanol, add 10 ul TE buffer to the pellet of magnetic beads and resuspend.

Example 2. PCR Amplification with Universal Primer

Reagents:

5× $2^{nd}$ PCR mix with non-hot-start Taq polymerase (Paragon Genomics)

10 µM Universal primer for the first round of PCR (Table 1, SEQ IDs NO: 1-8)

First Round of PCR:

Add the Following Mix to Make a 40 µl Reaction:

| | |
|---|---|
| DNA sample (above) | 10 µl |
| dH2O | 18 µl |
| 5× $2^{nd}$ PCR mix | 8 µl |
| 10 µM Universal primer | 4 µl |

Run the Following Thermal Cycling Protocol:

| | |
|---|---|
| Initial incubation | 65° C., 10 min |
| Run 10 cycles: | |
| Denaturation | 98° C., 15 sec, 3° C./s |
| Annealing/Extension | 60° C., 75 sec, 2° C./s |
| Hold | 10° C., ∞ |

After PCR, add 64 µl magnetic beads, incubate at room temperature for 15 minutes, wash twice with 70% ethanol, elute DNA into 10 ul TE buffer.

Example 3. Annealing and Extension of a Panel of Target Specific Primers

Reagents:

5× mPCR mix (Paragon Genomics)

10× Target specific primer panel (Table 2, SEQ IDs NO: 9-61)

Annealing and Extension of a Panel:

Add the Following Mix in a Fresh Tube to Make a 20 µl Reaction:

| | |
|---|---|
| DNA sample (above) | 10 µl |
| dH2O | 4 µl |
| 5× mPCR mix | 4 µl |
| 10× panel | 2 µl |

Run the Following Thermal Cycling Protocol:

| | |
|---|---|
| Initial incubation | 95° C., 10 min |
| Denaturation | 98° C., 15 sec, 3° C./s |
| Annealing/Extension | 60° C., 5 min, 0.4° C./s |
| Hold | 10° C., ∞ |

After PCR, add 32 µl magnetic beads, incubate at room temperature for 15 minutes, wash twice with 70% ethanol, elute DNA into 10 ul TE buffer.

Example 4. Digestion and Amplification

Reagents:

10× Exonuclease I Reaction Buffer (670 mM Glycine-KOH pH 9.5, 67 mM MgCl2, 100 mM β-ME)

Exonuclease I (NEB M0293L)

5× $2^{nd}$ PCR mix with non-hot-start Taq polymerase (Paragon Genomics)

10 µM Universal primers for the second round of PCR (Table 1, SEQ IDs NO: 1-8)

Digestion Reaction:

Add the Following Mix to a Fresh Tube to Make a 20 µl Reaction:

| | |
|---|---|
| dH2O | 6 µl |
| DNA sample (above) | 10 µl |
| 10× Digestion buffer | 2 µl |
| Exonuclease 1 | 2 µl |

Incubate at 37° C. for 30 minutes.

After PCR, add 32 µl magnetic beads, incubate at room temperature for 15 minutes, wash twice with 70% ethanol, add 10 ul TE buffer to the pellet of magnetic beads and resuspend.

Second Round of PCR:

Add the Following Mix to the Above DNA Sample:

| | |
|---|---|
| DNA sample (above) | 10 µl |
| dH2O | 4 µl |
| 5× $2^{nd}$ PCR mix | 4 µl |
| 10 µM Universal primers | 2 µl |

Run the Following Thermal Cycling Protocol:

| | |
|---|---|
| Initial incubation | 65° C., 10 min |
| Run 14 cycles: | |
| Denaturation | 98° C., 15 sec, 3° C./s |
| Annealing/Extension | 60° C., 75 sec, 2° C./s |
| Hold | 10° C., ∞ |

After PCR, add 32 µl magnetic beads, incubate at room temperature for 15 minutes, wash twice with 70% ethanol, elute DNA into 10 ul TE buffer.

Example 5. Digestion of U-Containing DNA and Amplification

Reagents:

10× Ligation buffer (500 mM Tris-HCl, pH7.5, 100 mM MgCl2, 5 mM ATP, 50 mM DTT)

Uracil-DNA Glycosylase (UDG) (NEB M0280L)

APE 1 (NEB M0282L)

5× $2^{nd}$ PCR mix with non-hot-start Taq polymerase (Paragon Genomics)

10 µM Universal primers for the second round of PCR (Table 1, SEQ IDs NO: 1-8)

Digestion Reaction:

Add the Following Mix to a Fresh Tube to Make a 20 µl Reaction:

| | |
|---|---|
| dH2O | 6 µl |
| DNA (from annealing and extension) | 10 µl |
| 10× Ligation buffer | 2 µl |
| UDG | 1 µl |
| APE 1 | 1 µl |

Incubate at 37° C. for 30 minutes.

After PCR, add 32 µl magnetic beads, incubate at room temperature for 15 minutes, wash twice with 70% ethanol, add 10 ul TE buffer to the pellet of magnetic beads and resuspend.

Second Round of PCR:
Add the Following Mix to the DNA Sample:

| DNA sample (above) | 10 µl |
| --- | --- |
| dH2O | 4 µl |
| 5× $2^{nd}$ PCR mix | 4 µl |
| 10 µM Universal primers | 2 µl |

Run the Following Thermal Cycling Protocol:

| Initial incubation | 95° C., 10 min |
| --- | --- |
| Run 14 cycles: | |
| Denaturation | 98° C., 15 sec, 3° C./s |
| Annealing/Extension | 60° C., 75 sec, 2° C./s |
| Hold | 10° C., ∞ |

After PCR, add 32 µl magnetic beads, incubate at room temperature for 15 minutes, wash twice with 70% ethanol, elute DNA into 10 ul TE buffer.

Example 6. Large Number of UMI Clusters Helps Reduce the Number of Errors

CleanPlex UMI technology was used to demonstrate the effect of number of UMI clusters on the reduction of errors. Briefly, DNA targets were amplified with a panel in the multiplex PCR reaction for three cycles. After removing redundant barcodes, the products of multiplex PCR were further amplified with a pair of primers to produce the library. The panel contains 53 pairs of primers. Each primer contains a 3' end target specific region, a 16-base UMI region, and a 5' end universal primer region. Template DNA, NA12878 and NA18507 (Coriell Institute) were mixed at 0.2% NA12878 in NA18507 (0.2% NA12878/NA18507) by weight, with total concentration at 40 nanograms per microliter (ng/µl). Other reference DNA included HD780 from Horizon Discovery, and Seraseq ctDNA Mutation Mix v2 (Catalog Number 0710-0143) from SeraCare.

10 to 100 ng of DNA was amplified with 30 nM each of the primers by multiplex PCR. The reagents and the method of multiplex PCR were provided by Paragon Genomics Inc. (CleanPlex™ Targeted Library Kit, SKU: 816001), similar to what was described in U.S. patent application Ser. No. 15/290,981. The multiplex PCR was stopped after three cycles, followed by purification of the amplification products with magnetic beads, the DNA was treated with 2 µl of CP Digestion Reagent supplemented with 2 units of *E. coli* exonuclease VII at 37° C. for 20 minutes. The reaction was purified with magnetic beads, and amplified again with a pair of second amplification primers. The size, concentration and purity of these libraries were assayed in a 2100 Bio-Analyzer instrument (Agilent Technologies, catalog number G2938B). 1 µl of each library was assayed with a high sensitivity DNA analysis kit (Agilent Technologies, catalog number 5067-4626), according to the methods provided by the supplier.

These libraries were sequenced on an Illumina NextSeq sequencer with a high output flowcell at 2×150 bp read length. After sequencing, the sequence data were filtered to remove those that did not mapped onto the human reference genome, and those that did not mapped onto the defined targets of amplification. Each library was sort out by the sample indexes, each of the 53 DNA targets (amplicons) was also sorted out by their sequence. Within each amplicon, molecules derived from different cells were further sorted out by the UMIs, forming UMI "clusters". Each cluster contains a different number of elements (also referred to as "reads"). All of the reads within a specific UMI cluster had identical molecular barcodes. In order to maximize the number of elements in each UMI cluster, the molecular barcodes were further analyzed by their sequence and length, one base error of UMI was allowed, e.g., any molecular barcode that differed from another one by only one base was placed in the same family. The members of each family were used to deduce a consensus sequence of the target DNA.

Figure 9:
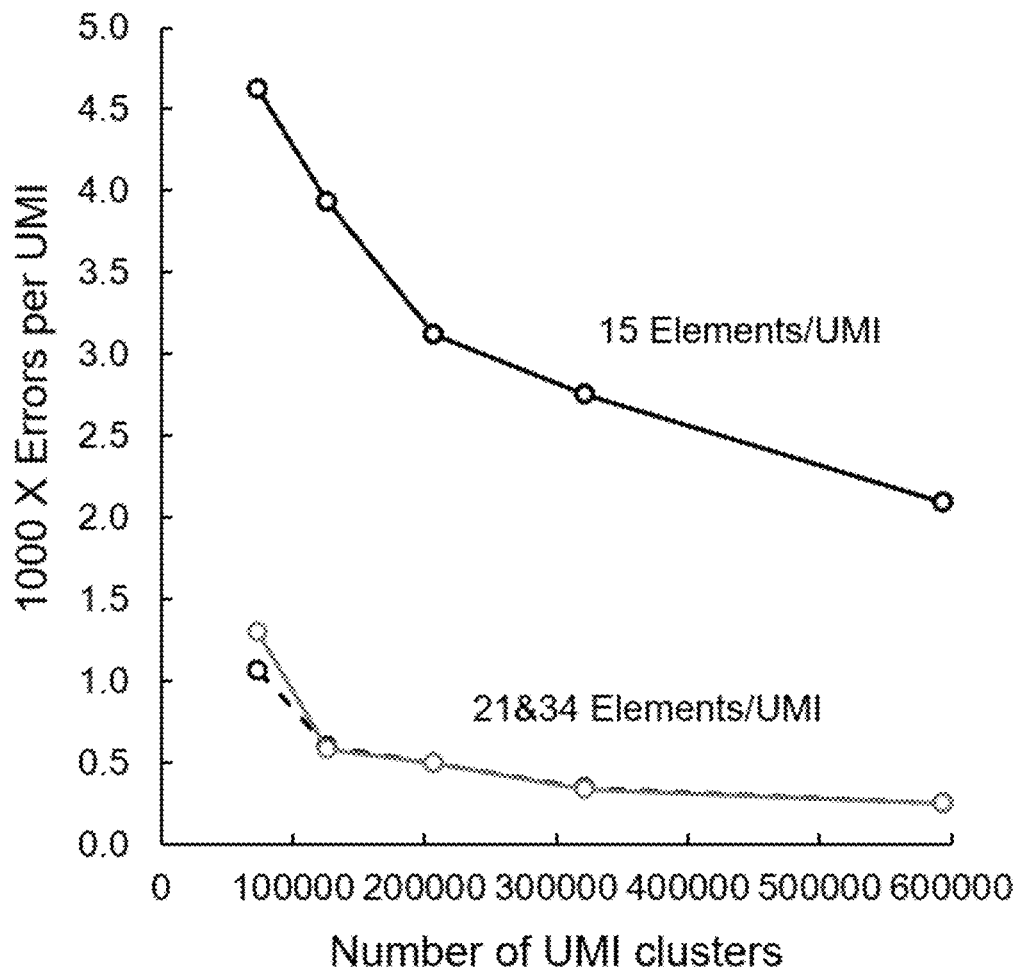
FIG. 9 is a graph showing that the number of errors can be reduced by increasing the number of UMI clusters, or by increasing the number of elements per UMI clone, or both.

The libraries were made from 10, 20, 30, 50, 100 ng of DNA and sequenced at low (averaged 15 element per UMI), mid (averaged 21 element per UMI) and high (averaged 34 element per UMI) sequencing depth. The recovered errors were plotted against the recovered number of UMI clusters at each sequencing depth (FIG. 9). It demonstrated that the number of errors declined with increasing number of UMI clusters in all sequencing depths, with conspicuous effect at 15 elements per UMI. It also showed that increasing sequencing depth, from 15 to 21 elements per UMI and at the similar number of UMI clusters, also helped reducing errors, with a plateaus at or before 34 elements per UMI.

Figure 10:
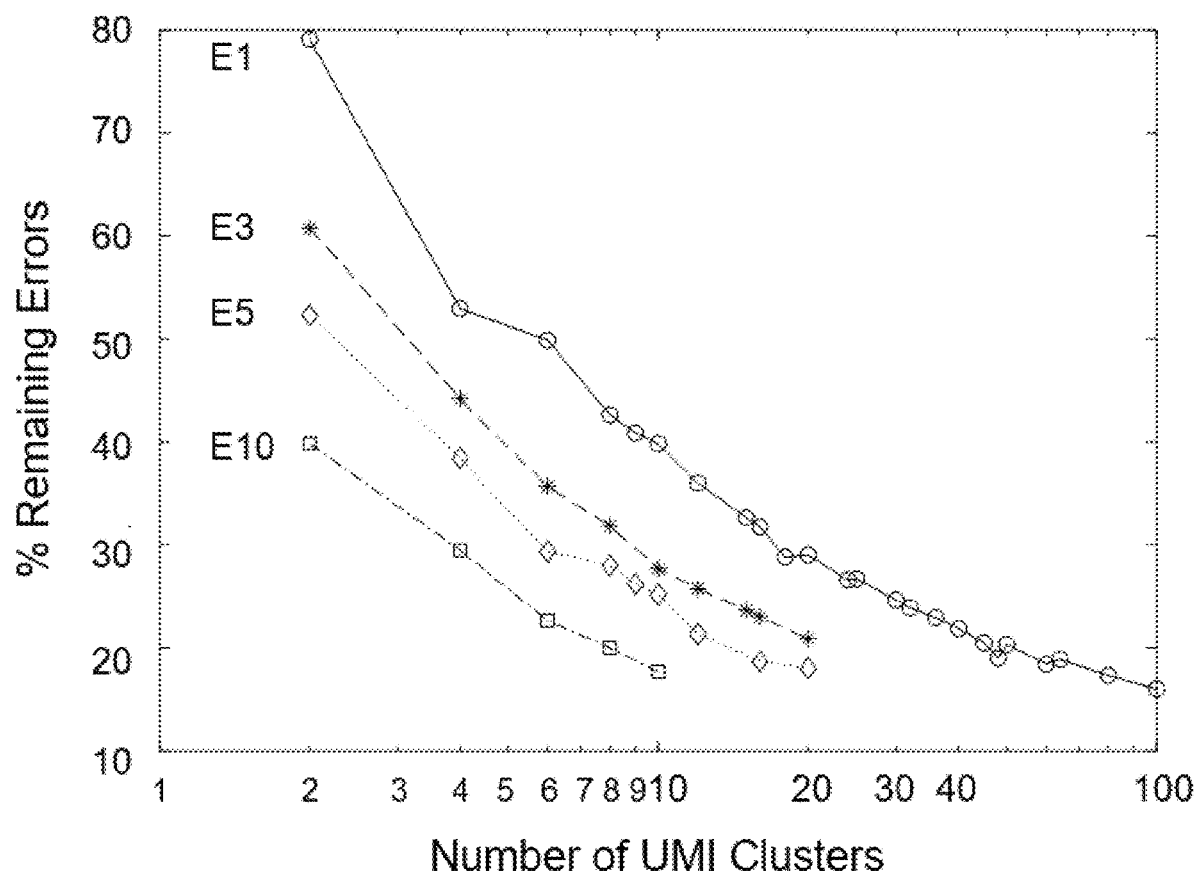
FIG. 10 is a graph showing the effect of the number of UMIs and the number of elements per UMI on error reduction by simulation. It was repeated found that the number of errors can be reduced by increasing the number of UMI clusters, or by increasing the number of elements per UMI clone, or both in simulation. It was further found that the total number of elements (the number of UMI clones and the number of elements per UMI clone, or the number of elements in a primary UMI clone) was the determinant factor.

Example 7. The Effect of the Number of UMIs and the Number of Elements Per UMI on Error Reduction by Simulation To simulate the effect of the number of UMIs and the number of elements per UMI on error reduction, a 150 bp base sequence of double-stranded DNA was digitized by converting A, T, G, C into 1, 2, 3, 4, respectively. This sequence was used to create a 200×150 matrix of bases. Random base errors, created as a matrix of 1, 2, 3 and 4, were assigned into the sequence matrix at 50%. Various UMIs and elements per UMI were then assigned into the matrix. The consensus base sequence was deduced by the codes in FIGS. 16A-16D. A result similar to FIG. 9 was found in simulation (FIG. 10). For example, the number of errors declined, at 10 elements per UMI, when the number of UMI clusters increased from 2 to 10. The same trend was found with 1, 3 and 5 elements per UMI. It was further found that a larger number of UMI subclones coupled with a smaller number of elements outperformed Duplex Seq when both were set at the same sequencing depth. For example, SubDivision Seq with 20 subclones each with 1 element out performed Duplex with 10 elements.

Figures 11A, 11B:
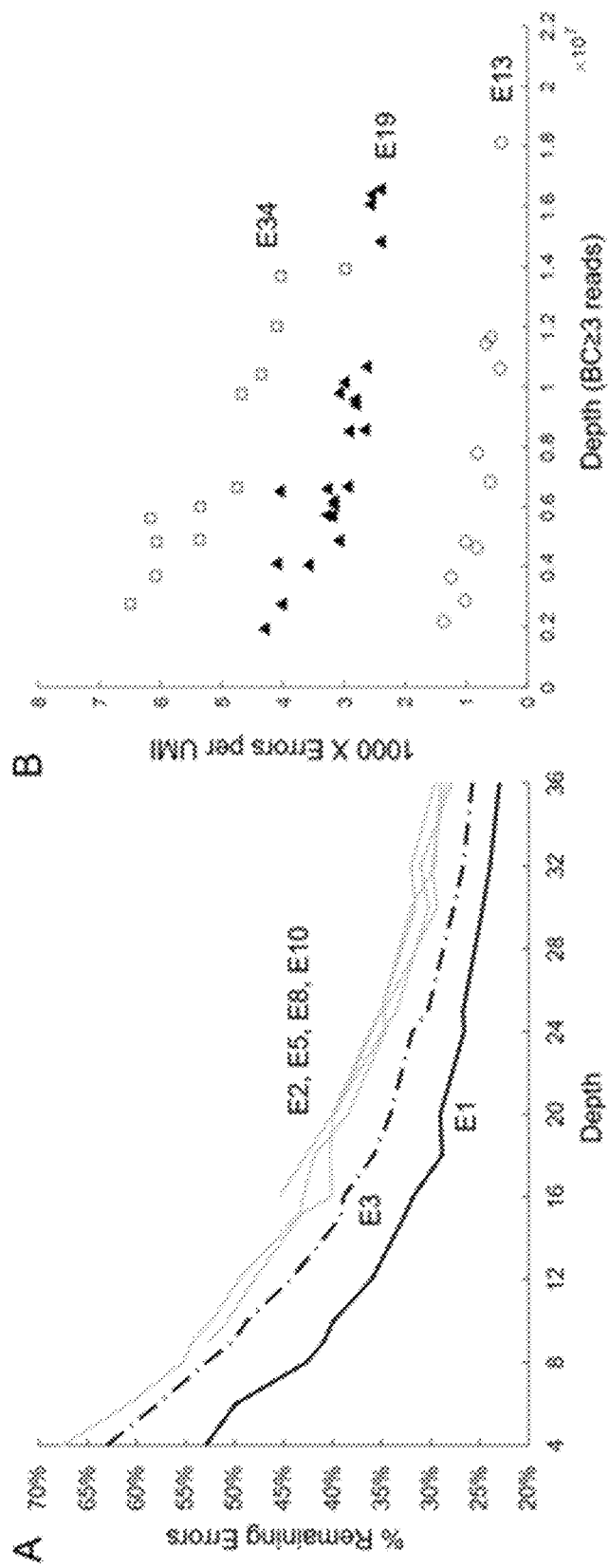
FIG. 11A is a graph showing the simulation results of SubDivision Seq with 1-10 elements per UMI subclone.
FIG. 11B is a graph of experimental evidence supporting the benefit of a larger number of UMI clones at a specified sequencing depth.

Example 8. The Relationship Between the Number of Elements and the Number of UMI Subclones in SubDivision Seq Through simulating 1-10 elements per UMI up to 100 UMI clusters, it was confirmed that the lowest number of errors happened with 1 element (FIG. 11A). 3 elements was the second most powerful, while 2 elements and the rest fell in a group that behaved similarly. To reach the same level of error reduction, the sequencing depth became higher rapidly if an element number other than one was used. Except for 2 elements, the results demonstrated that, at the same level of sequencing depth, a larger number of UMI subclones benefited error reduction. Three groups of cfDNA libraries were sequenced at various element numbers and sequencing depth (FIG. 11B). The results, supporting the findings from the simulation, indicated that a larger number of UMI clusters benefited error reduction.

Example 9. Additional Simulations and Comparison with Duplex Seq

To simulate the base errors happened in the early stages of DNA manipulations, 44% of random errors were created and assigned into 4 DNA fragments, each of these fragments were replicated 25 times to form a 100×150 base matrix. To simulate the asymmetrical errors happened on the sense and antisense strands, an additional 50% errors, created in a 100×150 matrix, were assigned into the base matrix to form the matrix of sense strands; an additional 57% errors, also created in a 100×150 matrix, were assigned into the base matrix to form the matrix of antisense strands.

Firstly, the case of one UMI subclone was first investigated. UMIs with elements of 2 to 100 were assigned among the matrix. The errors were reduced by finding consensus in sense strands along, in antisense strands along, and in a randomly mixed pool of sense and antisense strands. The results were averaged among multiple UMIs with identical number of elements. It was found that the effects of error reduction by these three methods were was similar (FIG. 12A). With 7% original difference in the number of errors on both strands, the difference of remaining errors on sense and antisense stands were fewer than 4%, while they differed from the mixed pool of both strands by fewer than 2%.

Secondly, two UMI subclones were investigated. In this case, consensus sequences were deduced from sense and antisense strand separately, the corresponding sense and antisense strands were matched and a second round of consensus was deduced (representing Duplex Seq). In comparison, sense and antisense strands were randomly mixed and used to deduce a first consensus sequence, then any two first consensus sequences were used to deduce a second consensus sequence. It was found that these two methods generated very close results in error reduction, with fewer than 3% difference in the remaining errors (FIG. 12B).

To investigate the effect of the number of UMI subclones on error reduction, Duplex Seq was compared with SubDivision seq with 2 elements per UMI subclones (FIG. 12C). In this case, Duplex's larger number of elements per UMI cluster was compared with SubDivision's larger number of UMI subclones, while the total depth is identical. It was found that SubDivision outperformed Duplex, indicating the number of UMI subclones is more effective in error reduction. In a big picture (FIG. 12D), SubDivision seq showed a sharp advantage over Duplex Seq, especially with 1 and 3 elements per UMI subclones and the sequencing depth was 50 and below. The error reduction effect of SubDivision Seq started to converge when the element number became 50 and larger.

Example 10. The Length of UMI in the Adaptor

UMI collision refers to the occurrence of an identical UMI is assigned onto ≥2 DNA molecules. This situation happens when the number of the variety of the available UMIs is lower by a factor than the number of the DNA molecules. The probability of UMI collision is calculated by the formula:

$$P = 1 - \left(1 - \frac{T}{2B}\right)^{(T-1)}$$

where T is the total number of DNA molecules per reaction (e.g., the number of DNA targets in a haploid genome per nanogram of DNA times DNA input by nanograms times PCR efficiency), B is the total number of the variety of UMIs (e.g., 4^length of UMI).

Figure 13A:
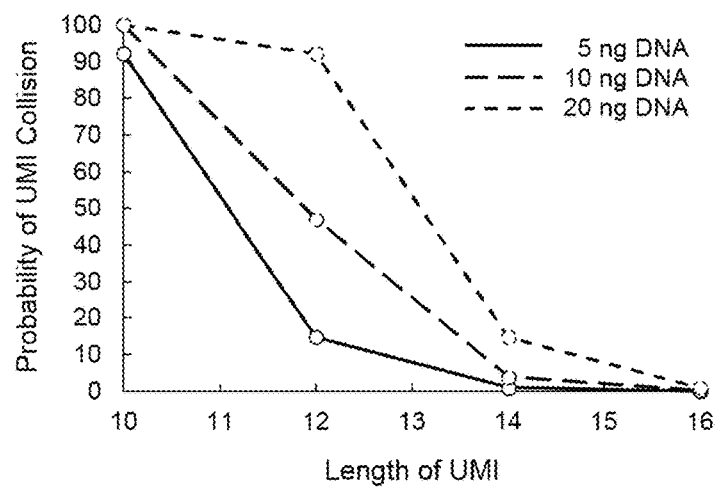
FIGS. 13A-13C are graphs showing the length of UMI in the adaptor.
Figure 13B:
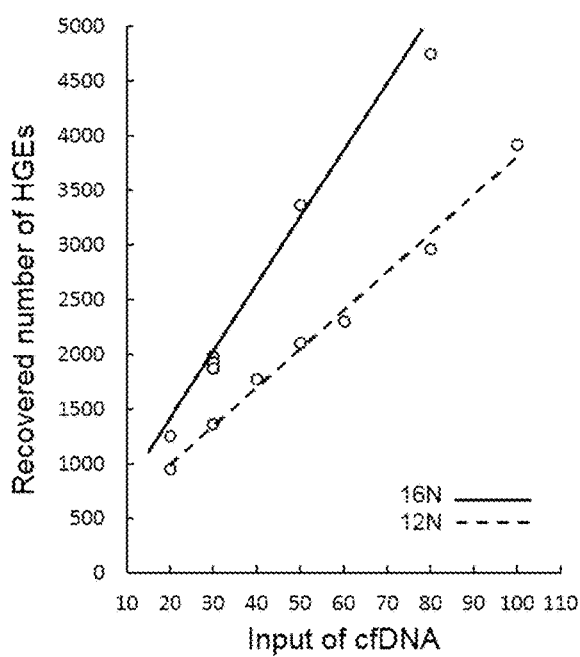
Figure 13C:
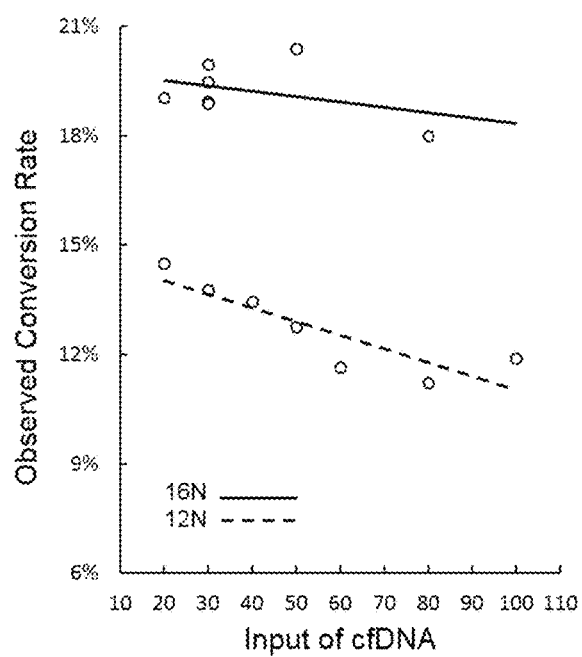

Considering the amount of input DNA spans a wide range, the probability of UMI collision was estimated with 5, 10 and 20 ng of human genomic DNA (FIG. 13A). It was found that a UMI comprised of 16 random bases was necessary and sufficient to suppress UMI collision. This conclusion was further confirmed by two groups of libraries made from 20-100 ng of cfDNA, one group was made with 12-base UMI (4^12 varieties), while the other with 16-base UMI (4^16 varieties). After sequencing the libraries, the recovered numbers of haploid genomes were compared between the two groups (FIG. 13B). Larger numbers of haploid genomes were recovered with 16-base UMI than with 12-base UMI, indicating a large number of DNA molecules were attached with a unique UMI when the number of the variety of the available UMIs was larger. It was noted that there was some UMI collision at 80 ng of cfDNA even with 16-base UMI. The conversion efficiency was additionally compared between these two groups of libraries (FIG. 13C). Here it demonstrated that UMI collision happened evidently with 12-base UMI, and it became severer when the amount of input cfDNA was larger.

Example 11. The Number of UMI Errors that are Allowed to be Corrected

Figure 14:
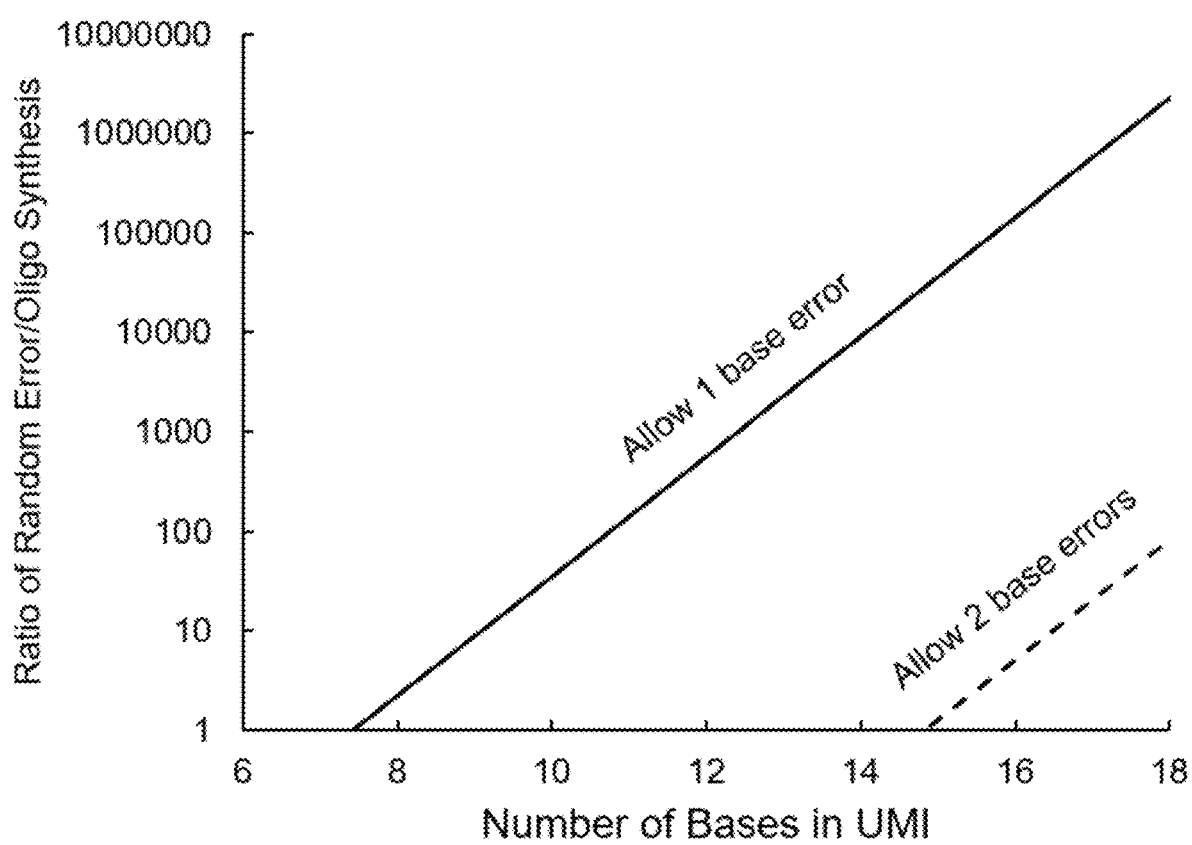
FIG. 14 is a graph showing only one UMI error is allowed for UMI containing 12-18 bases.

Base errors happen in the UMI region of DNA molecules during library preparation and sequencing, rendering an artificially high number of 1-element UMI clusters. To estimate the number of errors that could be allowed to assign a UMI into a UMI cluster, the probabilities of base errors and the chance of a similar occurrence derived from oligo synthesis were estimated. The probability of finding N base errors that randomly occur on UMI of length L during library preparation and sequencing is approximated by Poisson process. The probability of inherent base occurrence formed by oligo synthesis is estimated by the binomial equation:

$$P = \frac{L!}{m!(L-m)!}\left(\frac{1}{4}\right)^m\left(\frac{3}{4}\right)^{L-m}$$

where in a pool of synthesized random bases (UMI) of length L, the probability (P) of finding m identical bases in the same positions on any two oligos of length L is calculated. It was found that the chance of a single base random error was over 142,900-fold higher than the probability that this base change was due to oligo synthesis, while for changes of two bases, the difference was only 5-fold (FIG. 14). One base error was allowed to assign a UMI into a UMI cluster for a 16-base UMI (the same is true for 12 to 18-base UMIs).

Example 12. Low Depth Leads to Low Errors in UMI

The required sequencing depth is a function of the amount of input DNA, the conversion efficiency of target DNA to library and the number of DNA amplicons defined by the panel of the target specific primers. Generally, when there is a large amount of input DNA and the conversion efficiency is high, a large quantity of UMI clusters are obtained, and this requires high depth in sequencing to support the number of UMI clusters and the number of elements. To evaluate the effect of sequencing depth on the amount of single elements, a set of libraries was made and sequenced repeatedly in increasingly higher depths. The depth was defined as the average reads per nanogram of input DNA per amplicon. It was found that the depth of ≥4000 reads generated an extra amount of single element compared to depth of about 2000 reads (FIG. 15A). The same results were confirmed with a set of genomic DNA libraries, also sequenced repeatedly in increasingly higher depths (FIG. 15B). It is assumed that when the same libraries were sequenced in increasingly higher depths, the number of elements per UMI increases and the element distribution moves the to the right of the curve, and the number of single elements would have declined (FIG. 15C). Therefore, these extra single elements are most likely the artificial products generated from the errors in UMI region. Fewer single elements were observed with low sequencing depth in many samples collectively (FIG. 15D). This results suggests that a small number of elements per UMI cluster favors producing fewer errors in UMI.

This finding disfavor the requirements of Duplex Seq and ordinary UMI technologies, which require a large number of elements per UMI cluster (and discard all single elements) to reduce the number of errors. However, it is beneficial to SubDivision Seq, which requires a large number of UMI clusters, but the lowest number of elements.

It should be appreciated that all combinations of the foregoing concepts and additional concepts discussed in greater detail below (provided such concepts are not mutually inconsistent) are contemplated as being part of the inventive subject matter disclosed herein and may be used to achieve the benefits described herein.

The process parameters and sequence of steps described and/or illustrated herein are given by way of example only and can be varied as desired. For example, while the steps illustrated and/or described herein may be shown or discussed in a particular order, these steps do not necessarily need to be performed in the order illustrated or discussed. The various example methods described and/or illustrated herein may also omit one or more of the steps described or illustrated herein or include additional steps in addition to those disclosed.

Any of the methods (including user interfaces) described herein may be implemented as software, hardware or firmware, and may be described as a non-transitory computer-readable storage medium storing a set of instructions capable of being executed by a processor (e.g., computer, tablet, smartphone, etc.), that when executed by the processor causes the processor to control perform any of the steps, including but not limited to: displaying, communicating with the user, analyzing, modifying parameters (including timing, frequency, intensity, etc.), determining, alerting, or the like. For example, any of the methods described herein may be performed, at least in part, by an apparatus including one or more processors having a memory storing a non-transitory computer-readable storage medium storing a set of instructions for the processes(s) of the method.

Section headings used herein are for organizational purposes only and are not to be construed as limiting the described subject matter in any way.

While various embodiments have been described and/or illustrated herein in the context of fully functional computing systems, one or more of these example embodiments may be distributed as a program product in a variety of forms, regardless of the particular type of computer-readable media used to actually carry out the distribution. The embodiments disclosed herein may also be implemented using software modules that perform certain tasks. These software modules may include script, batch, or other executable files that may be stored on a computer-readable storage medium or in a computing system. In some embodiments, these software modules may configure a computing system to perform one or more of the example embodiments disclosed herein.

As described herein, the computing devices and systems described and/or illustrated herein broadly represent any type or form of computing device or system capable of executing computer-readable instructions, such as those contained within the modules described herein. In their most basic configuration, these computing device(s) may each comprise at least one memory device and at least one physical processor.

The term "memory" or "memory device," as used herein, generally represents any type or form of volatile or non-volatile storage device or medium capable of storing data and/or computer-readable instructions. In one example, a memory device may store, load, and/or maintain one or more of the modules described herein. Examples of memory devices comprise, without limitation, Random Access Memory (RAM), Read Only Memory (ROM), flash memory, Hard Disk Drives (HDDs), Solid-State Drives (SSDs), optical disk drives, caches, variations or combinations of one or more of the same, or any other suitable storage memory.

In addition, the term "processor" or "physical processor," as used herein, generally refers to any type or form of hardware-implemented processing unit capable of interpreting and/or executing computer-readable instructions. In one example, a physical processor may access and/or modify one or more modules stored in the above-described memory device. Examples of physical processors comprise, without limitation, microprocessors, microcontrollers, Central Processing Units (CPUs), Field-Programmable Gate Arrays (FPGAs) that implement softcore processors, Application-Specific Integrated Circuits (ASICs), portions of one or more of the same, variations or combinations of one or more of the same, or any other suitable physical processor.

Although illustrated as separate elements, the method steps described and/or illustrated herein may represent portions of a single application. In addition, in some embodiments one or more of these steps may represent or correspond to one or more software applications or programs that, when executed by a computing device, may cause the computing device to perform one or more tasks, such as the method step.

In addition, one or more of the devices described herein may transform data, physical devices, and/or representations of physical devices from one form to another. Additionally or alternatively, one or more of the modules recited herein may transform a processor, volatile memory, non-volatile memory, and/or any other portion of a physical computing device from one form of computing device to another form of computing device by executing on the computing device, storing data on the computing device, and/or otherwise interacting with the computing device.

The term "computer-readable medium," as used herein, generally refers to any form of device, carrier, or medium capable of storing or carrying computer-readable instructions. Examples of computer-readable media comprise, without limitation, transmission-type media, such as carrier waves, and non-transitory-type media, such as magnetic-storage media (e.g., hard disk drives, tape drives, and floppy disks), optical-storage media (e.g., Compact Disks (CDs), Digital Video Disks (DVDs), and BLU-RAY disks), electronic-storage media (e.g., solid-state drives and flash media), and other distribution systems.

A person of ordinary skill in the art will recognize that any process or method disclosed herein can be modified in many ways. The process parameters and sequence of the steps described and/or illustrated herein are given by way of example only and can be varied as desired. For example, while the steps illustrated and/or described herein may be shown or discussed in a particular order, these steps do not necessarily need to be performed in the order illustrated or discussed.

The various exemplary methods described and/or illustrated herein may also omit one or more of the steps described or illustrated herein or comprise additional steps in addition to those disclosed. Further, a step of any method as disclosed herein can be combined with any one or more steps of any other method as disclosed herein.

The processor as described herein can be configured to perform one or more steps of any method disclosed herein. Alternatively or in combination, the processor can be configured to combine one or more steps of one or more methods as disclosed herein.

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one embodiment, the features and elements so described or shown can apply to other embodiments. It will also be appreciated by those of skill in the art that references to a structure or feature that is disposed "adjacent" another feature may have portions that overlap or underlie the adjacent feature.

Terminology used herein is for the purpose of describing particular embodiments only and is not intended to be limiting of the invention. For example, as used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items and may be abbreviated as "/".

Spatially relative terms, such as "under", "below", "lower", "over", "upper" and the like, may be used herein for ease of description to describe one element's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

Although the terms "first" and "second" may be used herein to describe various features/elements (including steps), these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings of the present invention.

Throughout this specification and the claims which follow, unless the context requires otherwise, the word "comprise", and variations such as "comprises" and "comprising" means various components can be co-jointly employed in the methods and articles (e.g., compositions and apparatuses including device and methods). For example, the term "comprising" will be understood to imply the inclusion of any stated elements or steps but not the exclusion of any other elements or steps.

In general, any of the apparatuses and methods described herein should be understood to be inclusive, but all or a sub-set of the components and/or steps may alternatively be exclusive, and may be expressed as "consisting of" or alternatively "consisting essentially of" the various components, steps, sub-components or sub-steps.

As used herein in the specification and claims, including as used in the examples and unless otherwise expressly specified, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical values given herein should also be understood to include about or approximately that value, unless the context indicates otherwise. For example, if the value "10" is disclosed, then "about 10" is also disclosed. Any numerical range recited herein is intended to include all sub-ranges subsumed therein. It is also understood that when a value is disclosed that "less than or equal to" the value, "greater than or equal to the value" and possible ranges between values are also disclosed, as appropriately understood by the skilled artisan. For example, if the value "X" is disclosed the "less than or equal to X" as well as "greater than or equal to X" (e.g., where X is a numerical value) is also disclosed. It is also understood that the throughout the application, data is provided in a number of different formats, and that this data, represents endpoints and starting points, and ranges for any combination of the data points. For example, if a particular data point "10" and a particular data point "15" are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

Although various illustrative embodiments are described above, any of a number of changes may be made to various embodiments without departing from the scope of the invention as described by the claims. For example, the order in which various described method steps are performed may often be changed in alternative embodiments, and in other alternative embodiments one or more method steps may be skipped altogether. Optional features of various device and system embodiments may be included in some embodiments and not in others. Therefore, the foregoing description is provided primarily for exemplary purposes and should not be interpreted to limit the scope of the invention as it is set forth in the claims.

The examples and illustrations included herein show, by way of illustration and not of limitation, specific embodiments in which the subject matter may be practiced. As mentioned, other embodiments may be utilized and derived there from, such that structural and logical substitutions and changes may be made without departing from the scope of this disclosure. Such embodiments of the inventive subject matter may be referred to herein individually or collectively by the term "invention" merely for convenience and without intending to voluntarily limit the scope of this application to any single invention or inventive concept, if more than one is, in fact, disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

Tables

TABLE 1

List of adaptors and universal primers.

Single-stranded 5' adaptor without UMI:
/5AmMC6/CCTACACGACGCTCTTCCGATCTrNrNrNrN

Single-stranded 5' adaptor with UMI:
/5AmMC6/CCTACACGACGCTCTTCCGATCTNNNNNNNNNNNNNrNrNrNrN Single-stranded 5' adaptor with UMI and sample barcode:
/5AmMC6/AATGATACGGCGACCACCGAGATCTACAC-NNNNNNNN-
ACACTCTTTCCCTACACGACGCTCTTCCGATCTNNNNNNNNNNNNNrNrNrNrN Single-stranded 3' adaptor with UMI:
NNNNNNNNNNNNNNNNNAGATCGGAAGAGCGTCGTGTAGG/3ddC/

Universal primer for the first round of PCR:
CCTACACGACGCTCTTCCGATCT

Universal primer with Us for the first round of PCR:
CCTACACGACGC/ideoxyU/CT/ideoxyU/CCGA/ideoxyU/CT Universal primers for the second round of PCR:
5'AATGATACGGCGACCACCGAGATCTACAC-NNNNNNNN-ACACTCTTTCCCTACACGACGCTCTTCCGATC*T
5'CAAGCAGAAGACGGCATACGAGAT-NNNNNNNN-GTGACTGGAGTTCAGACGTGTGCTCTTCCGATC*T

TABLE 2

List of a panel of target specific primers.

TTCAGACGTGTGCTCTTCCGATCTNNNNCAAGAGTTACGGGATTCCATTCAT

TTCAGACGTGTGCTCTTCCGATCTNNNGGTGAAACCTGTTTGTTGGACATAC

TTCAGACGTGTGCTCTTCCGATCTNNNNTTGCTGGTGTGAAATGACTGAGTAC

TTCAGACGTGTGCTCTTCCGATCTNNNNCAATCCCTGCCCCGGTTCA

TTCAGACGTGTGCTCTTCCGATCTNNNNTCAGTTAATTTTGGTTACATCCCTCTCT

TTCAGACGTGTGCTCTTCCGATCTNNNNTCTGGTAGAACAGTTCTTCACTGAAAAT

TTCAGACGTGTGCTCTTCCGATCTNNNNTCAGGATTGCCTTTACCACTC

TTCAGACGTGTGCTCTTCCGATCTNNNGAACCTTTACCACACTGCTGAACC

TTCAGACGTGTGCTCTTCCGATCTNNNNACTTACCTGTGACTCCATAGAAAATCTT

TTCAGACGTGTGCTCTTCCGATCTNNNNTGGAAGATCCAATCCATTTTTGTTGT

TTCAGACGTGTGCTCTTCCGATCTNNNCGTCTTAGTGTAATACTGTAGTGGTCAT

TTCAGACGTGTGCTCTTCCGATCTNNNGACTCTATCTTCATTATTTGGGAGCTTA

TABLE 2-continued

List of a panel of target specific primers.

TTCAGACGTGTGCTCTTCCGATCTNNNCCTGATGGGCAGATTACAGTG

TTCAGACGTGTGCTCTTCCGATCTNNNAGAGGAATGCAGCTTGTACTGG

TTCAGACGTGTGCTCTTCCGATCTNNNCATGTGTAGAAAGCAGATTTCTCCAT

TTCAGACGTGTGCTCTTCCGATCTNNNGCCTAGTCCCTGGCTGGAC

TTCAGACGTGTGCTCTTCCGATCTNNNGAAGAAGATGTGGAAAAGTCCCAATG

TTCAGACGTGTGCTCTTCCGATCTNNNCACTACAACTACATGTGTAACAGTTCC

TTCAGACGTGTGCTCTTCCGATCTNNNCCTCCTCAGCATCTTATCCGA

TTCAGACGTGTGCTCTTCCGATCTNNNGACCCAGGTCCAGATGAAGC

TTCAGACGTGTGCTCTTCCGATCTNNNCTGCACAGCGTCTCCGAGT

TTCAGACGTGTGCTCTTCCGATCTNNNCTTACGGGAGGGAAGTCAAAG

TTCAGACGTGTGCTCTTCCGATCTNNNTCTTTGTGTTCCCGGACATAGT

TTCAGACGTGTGCTCTTCCGATCTNNNTGTGAGTGGATGGGTAAAACCTA

TTCAGACGTGTGCTCTTCCGATCTNNNCAGAAATGCATCAAGCTTCTGTTC

TTCAGACGTGTGCTCTTCCGATCTNNNGCAGAGCGTCACAGCCG

TTCAGACGTGTGCTCTTCCGATCTNNNTTCTCCCTCTGCAGAGTTGTTA

TTCAGACGTGTGCTCTTCCGATCTNNNTGACACTGCTGGAACTTCG

TTCAGACGTGTGCTCTTCCGATCTNNNGGGACCTTACCTTATACACCGT

TTCAGACGTGTGCTCTTCCGATCTNNNCACAGCAAAGCAGAAACTCAC

TTCAGACGTGTGCTCTTCCGATCTNNNCTCCTTCTGCATGGTATTCTTTCTC

TTCAGACGTGTGCTCTTCCGATCTNNNCTTTACAGATGAAAGGACTTTGGCT

TTCAGACGTGTGCTCTTCCGATCTNNNCGGTAGTCTACAGATTCATTTGAAACC

TTCAGACGTGTGCTCTTCCGATCTNNNCTTGCCATCATTGTCCAACAAAG

TTCAGACGTGTGCTCTTCCGATCTNNNCTTTACTTACTACACCTCAGATATATTTCTTCA

TTCAGACGTGTGCTCTTCCGATCTNNNGCTGGACGTGCGCGATG

TTCAGACGTGTGCTCTTCCGATCTNNNGAGACTCACAAGAATTTTCTCCAGTAC

TTCAGACGTGTGCTCTTCCGATCTNNNCGTTTGCATCACTAACACTACTATCA

TTCAGACGTGTGCTCTTCCGATCTNNNCATATCATAGACCTTGGTAGCAGTCT

TTCAGACGTGTGCTCTTCCGATCTNNNAGCAAGAAGTTATGGAATTCCTTTTATTGA

TTCAGACGTGTGCTCTTCCGATCTNNNTCTGAAGATGTACCTATGGTCCTAGTA

TTCAGACGTGTGCTCTTCCGATCTNNNGAGAAACCTGTCTCTTGGATATTCTC

TTCAGACGTGTGCTCTTCCGATCTNNNTGACTGAATATAAACTTGTGGTAGTTGGA

TTCAGACGTGTGCTCTTCCGATCTNNNTAGAGTGTGCGTGGCTCT

TTCAGACGTGTGCTCTTCCGATCTNNNCCACAAAATCGTGTCCTGGTAG

TTCAGACGTGTGCTCTTCCGATCTNNNGCTGTCACCTCTTGGTTGTG

TTCAGACGTGTGCTCTTCCGATCTNNNGTCTCCGCATCGTGTACTTC

TTCAGACGTGTGCTCTTCCGATCTNNNGTCTAAGATTTCTTTGTTGGCTTTGG

TTCAGACGTGTGCTCTTCCGATCTNNNCAGAAGGCGGGAGACATATG

TTCAGACGTGTGCTCTTCCGATCTNNNACCATAACTCCACACATCACTCT

TTCAGACGTGTGCTCTTCCGATCTNNNCACGGTCTGGGAAGTGTTT

TABLE 2-continued

List of a panel of target specific primers.

TTCAGACGTGTGCTCTTCCGATCTNNNGAACTTGGTCTCAAAGATTCCAGAA

TTCAGACGTGTGCTCTTCCGATCTNNNACTTGCGGCGTTCATCG

---

What is claimed is:

1. A method of reducing base errors in sequencing double-stranded DNA targets, wherein each primary clone of a DNA target is subdivided into subclones along the course of DNA amplifications, wherein base errors are reduced by finding consensus sequence in each subclone and then in each primer clone, the method comprising:
    forming primary clones from double-stranded DNA molecules by:
        ligating an adapter to both ends of each of a plurality of double-stranded DNA molecules, wherein the adapter comprises a unique molecular identifier (UMI) and a first universal primer binding site for PCR amplification, and the UMI comprises 12 or more bases including degenerate or semi-degenerate base sequences, and
        amplifying the adapter-DNA complexes with a first universal primer, resulting in each strand of the DNA molecule producing a clone of itself;
    subdividing each primary clone into subclones comprising:
        annealing and extending a plurality of target-specific primers to the primary clones, wherein each of the target-specific primer comprises a target-specific region, a UMI and a second universal primer binding site for PCR amplification, resulting in each primary clone being subdivided into multiple subclones defined by the UMIs on the target-specific primers on one side of the resulting molecules, while each primary clone is still identifiable by the UMI from the adapter on the other side of the resulting molecules,
        enzymatically removing single-stranded regions from 3' ends in the primary clones, and
        amplifying the resulting products using the first universal primer and a second universal primer;
    sequencing the resulting products; and
    removing base errors after sequencing, comprising:
        sorting sequences into primary clones by UMIs on the adapters on one side of the molecules, then sorting each primary clone into subclones by the UMIs on the target-specific primers on the other side of the molecules, and
        deducing consensus sequence from each subclone, then deducing consensus sequence in each primary clone from the consensus sequences obtained from the subclones within each primary clone.

2. The method of claim 1, wherein ligating the adapter further comprises blunting ends and phosphorylating the 5' ends of the DNA molecules.

3. The method of claim 1, wherein ligating the adapter comprises ligating ssDNA adapter to 5' end of the DNA molecules.

4. The method of claim 1, wherein ligating the adapter comprises ligating ssDNA adapter to 3' end of the DNA molecules.

5. The method of claim 1, wherein ligating the adapter comprises ligating dsDNA adapter to the double strands of the DNA molecules.

6. The method of claim 1, wherein ligating the adapter comprises ligating one strand of dsDNA adapter to 5' end of the DNA molecules.

7. The method of claim 1, wherein ligating the adapter comprises ligating one strand of dsDNA adapter to 3' end of the DNA molecules.

8. The method of claim 1, wherein ligating the adapter comprises tagging a ssDNA adapter by template switching.

9. The method of claim 1, wherein the degenerate or semi-degenerate bases in UMI of the adapter have between 8 to 20 random bases.

10. The method of claim 1, wherein amplifying the adapter-DNA complexes comprises amplifying with one universal primer by PCR or linear amplification.

11. The method of claim 1, wherein amplifying the adapter-DNA complexes comprises amplifying with a pair of universal primers by PCR.

12. The method of claim 1, wherein one or both of the universal primers have one or multiple Us replacing Ts.

13. The method of claim 1, wherein the degenerate or semi-degenerate bases in the UMI of the target-specific primer have between 8 to 20 random bases.

14. The method of claim 1, wherein the degenerate or semi-degenerate bases in the UMI of the target-specific primer have between 0 and 20 random bases.

15. The method of claim 1, wherein the plurality of target-specific primers is a panel of reverse primers, or a panel of forward primers, or a panel of both forward and reverse primers.

16. The method of claim 1, wherein the number of the plurality of target-specific primers is 2-100,000.

17. The method of claim 1, wherein enzymatically removing the single-stranded regions comprises removing single stranded DNA regions and single stranded DNA by using 3' to 5' single-stranded DNA specific exonuclease.

18. The method of claim 1, wherein enzymatically removing the single-stranded regions further comprises, for U-containing universal primers, creating nicks in double stranded DNA and breaks in single stranded DNA at the sites of Us by using UDG and APE 1, or UDG and fpg, or UDG and Endo IV.

19. The method of claim 1, wherein enzymatically removing the single-stranded regions further comprises, for U-containing universal primers, removing single stranded DNA regions and single stranded DNA by using 3' to 5' single-strand DNA specific exonuclease, and creating nicks in double stranded DNA and breaks in single stranded DNA at the sites of Us by using UDG and APE 1, or UDG and fpg, or UDG and Endo IV.

20. The method of claim 1, wherein amplifying the resulting products includes adding sample barcodes.

21. The method of claim 1, further comprising hybridization capture after amplifying the adapter-DNA complexes.

22. The method of claim 1, wherein deducing consensus sequence further comprises calculating mutation frequency based on the number of clones of a specific mutation.

23. A method of reducing base errors in sequencing double-stranded DNA targets, wherein each primary clone of a DNA target is subdivided into subclones along the course of DNA amplifications, wherein base errors are reduced by finding consensus sequence in each subclone and then in each primary clone, the method comprising:
    forming primary clones from double-stranded DNA molecules by:
        ligating an adapter to both ends of each of a plurality of double-stranded target DNA molecules, wherein the adapter comprises a first universal primer binding site for PCR amplification, wherein each primary clone is identified by the nucleotide sequences at both ends and the length of the DNA molecule, and
        amplifying the adapter-target complexes with the universal primer binding site, resulting in each strand of the target molecule producing a clone of itself;

subdividing each primary clone into subclones by:
  annealing and extending a plurality of target-specific primers to the primary clones, wherein each of the target-specific primers comprises a target-specific region, a unique molecular identifier (UMI) and a second universal primer binding site for PCR amplification, resulting in each primary clone being subdivided into multiple subclones defined by the UMIs on the target-specific primers of the resulting molecules,
  enzymatically removing single-stranded regions from 3' ends in the primary clones, and
  amplifying the resulting products using the first and second universal primer binding sites;
sequencing the resulting products; and
removing base errors after sequencing by:
  sorting sequences into primary clones by the nucleotide sequences and the lengths of the target molecules, then sorting each primary clone into subclones by the UMIs on the target-specific primers, and
  deducing consensus sequence from each subclone, then deducing consensus sequence in each primary clone from the consensus sequences obtained from the subclones within each primary clone.

24. A method of reducing base errors in sequencing double-stranded DNA targets, wherein each primary clone of DNA target is subdivided into subclones along the course of DNA amplifications, wherein base errors are reduced by finding consensus sequence in each subclone and then in each primary clone, the method comprising:
  forming primary unique molecular identifier (UMI) clones from double-stranded DNA molecules by:
    ligating an adapter to both ends of each of a plurality of double-stranded DNA molecules, wherein the adapter comprises a UMI, a first universal primer binding site for PCR amplification and a sample barcode, wherein the UMI comprises 12 or more bases including degenerate or semi-degenerate base sequence;
    amplifying the adapter-DNA complexes with a first universal primer, resulting in each strand producing a clone of itself;
  pooling samples and target enrichment by hybridization capture, including pooling together the amplified plurality of DNA molecules from multiple samples amplifying the adapter-DNA, followed by hybridization and capturing with a plurality of target-specific oligos, wherein each of the target-specific oligo is tagged with biotin moiety for capturing with streptavidin-coupled magnetic beads;
  subdividing each primary UMI clone into UMI subclones by:
    annealing and extending a plurality of target-specific primers to the primary UMI clones, wherein each of the target-specific primers comprises a target-specific region, a UMI and a second universal primer binding site for PCR amplification, resulting in each primary clone being subdivided into multiple subclones defined by the UMIs on the target-specific primers on one side of the resulting molecules, while each primary clone is still identifiable by the UMI from the adapter on the other side of the resulting molecules;
    enzymatically removing single-stranded regions from 3' ends in the primary clones; and
    amplifying the resulting products using the first universal primer and a second universal primer;
  sequencing the resulting products; and
  removing base errors after sequencing by:
    sorting sequences into primary UMI clones by UMI on one side of the molecules and the sequences of the plurality of the amplified targets, then sorting each primary clone into subclones by the UMI on the other side of the molecules, and
    deducing consensus sequence from each subclone, then deducing consensus sequence in each primary clone from the consensus sequences obtained from the subclones within each primary clone.

* * * * *

SEQUENCE LISTING

<160> NUMBER OF SEQ ID NOS: 61

<210> SEQ ID NO 1
<211> LENGTH: 27
<212> TYPE: DNA
<213> ORGANISM: Artificial Sequence
<220> FEATURE:
<223> OTHER INFORMATION: Single-stranded 5' adaptor without UMI
<220> FEATURE:
<221> NAME/KEY: misc_feature
<222> LOCATION: (24)..(27)
<223> OTHER INFORMATION: The nucleotides are Ribonucleotides

<400> SEQUENCE: 1
cctacacgac gctcttccga tctnnnn                              27

<210> SEQ ID NO 2
<211> LENGTH: 39
<212> TYPE: DNA
<213> ORGANISM: Artificial Sequence
<220> FEATURE:
<223> OTHER INFORMATION: Single-stranded 5' adaptor with UMI
<220> FEATURE:
<221> NAME/KEY: misc_feature
<222> LOCATION: (24)..(35)
<223> OTHER INFORMATION: n is a, c, g, or t
<220> FEATURE:
<221> NAME/KEY: misc_feature
<222> LOCATION: (36)..(39)
<223> OTHER INFORMATION: The nucleotides are Ribonucleotides

<400> SEQUENCE: 2
cctacacgac gctcttccga tctnnnnnnn nnnnnnnn                   39

<210> SEQ ID NO 3
<211> LENGTH: 86
<212> TYPE: DNA
<213> ORGANISM: Artificial Sequence
<220> FEATURE:
<223> OTHER INFORMATION: Single-stranded 5' adaptor with UMI and sample
      barcode
<220> FEATURE:
<221> NAME/KEY: misc_feature
<222> LOCATION: (30)..(37)
<223> OTHER INFORMATION: n is a, c, g, or t
<220> FEATURE:
<221> NAME/KEY: misc_feature
<222> LOCATION: (71)..(82)
<223> OTHER INFORMATION: n is a, c, g, or t
<220> FEATURE:
<221> NAME/KEY: misc_feature
<222> LOCATION: (83)..(86)
<223> OTHER INFORMATION: The nucleotides are Ribonucleotides

<400> SEQUENCE: 3
aatgatacgg cgaccaccga gatctacacn nnnnnnnaca ctctttccct acacgacgct     60
cttccgatct nnnnnnnnnn nnnnnn                                         86

<210> SEQ ID NO 4

```
<211> LENGTH: 40
<212> TYPE: DNA
<213> ORGANISM: Artificial Sequence
<220> FEATURE:
<223> OTHER INFORMATION: Single-stranded 3' adaptor with UMI
<220> FEATURE:
<221> NAME/KEY: misc_feature
<222> LOCATION: (1)..(16)
<223> OTHER INFORMATION: n is a, c, g, or t
<220> FEATURE:
<221> NAME/KEY: modified_base
<222> LOCATION: (40)..(40)
<223> OTHER INFORMATION: C is Dideoxy Cytosine

<400> SEQUENCE: 4
nnnnnnnnnn nnnnnnagat cggaagagcg tcgtgtaggc                          40

<210> SEQ ID NO 5
<211> LENGTH: 23
<212> TYPE: DNA
<213> ORGANISM: Artificial Sequence
<220> FEATURE:
<223> OTHER INFORMATION: Universal primer for the first round of PCR

<400> SEQUENCE: 5
cctacacgac gctcttccga tct                                            23

<210> SEQ ID NO 6
<211> LENGTH: 23
<212> TYPE: DNA
<213> ORGANISM: Artificial Sequence
<220> FEATURE:
<223> OTHER INFORMATION: Universal primer with Us for the first round of
      PCR
<220> FEATURE:
<221> NAME/KEY: misc_feature
<222> LOCATION: (13)..(13)
<223> OTHER INFORMATION: The nucleotide is Dideoxyuridine
<220> FEATURE:
<221> NAME/KEY: misc_feature
<222> LOCATION: (16)..(16)
<223> OTHER INFORMATION: The nucleotide is Dideoxyuridine
<220> FEATURE:
<221> NAME/KEY: misc_feature
<222> LOCATION: (21)..(21)
<223> OTHER INFORMATION: The nucleotide is Dideoxyuridine

<400> SEQUENCE: 6
cctacacgac gcnctnccga nct                                            23

<210> SEQ ID NO 7
<211> LENGTH: 69
<212> TYPE: DNA
<213> ORGANISM: Artificial Sequence
<220> FEATURE:
<223> OTHER INFORMATION: Universal primers for the second round of PCR
<220> FEATURE:
<221> NAME/KEY: misc_feature
<222> LOCATION: (30)..(37)
<223> OTHER INFORMATION: n is a, c, g, or t

<400> SEQUENCE: 7
aatgatacgg cgaccaccga gatctacacn nnnnnnnaca ctctttccct acacgacgct    60
cttccgatc                                                            69

<210> SEQ ID NO 8
<211> LENGTH: 65
<212> TYPE: DNA
<213> ORGANISM: Artificial Sequence
<220> FEATURE:
```

```
<223> OTHER INFORMATION: Universal primers for the second round of PCR
<220> FEATURE:
<221> NAME/KEY: misc_feature
<222> LOCATION: (25)..(32)
<223> OTHER INFORMATION: n is a, c, g, or t

<400> SEQUENCE: 8
caagcagaag acggcatacg agatnnnnnn nngtgactgg agttcagacg tgtgctcttc    60
cgatc                                                                65

<210> SEQ ID NO 9
<211> LENGTH: 51
<212> TYPE: DNA
<213> ORGANISM: Artificial Sequence
<220> FEATURE:
<223> OTHER INFORMATION: Target specific primer
<220> FEATURE:
<221> NAME/KEY: misc_feature
<222> LOCATION: (25)..(27)
<223> OTHER INFORMATION: n is a, c, g, or t

<400> SEQUENCE: 9
ttcagacgtg tgctcttccg atctnnncaa gagttacggg attccattca t            51

<210> SEQ ID NO 10
<211> LENGTH: 52
<212> TYPE: DNA
<213> ORGANISM: Artificial Sequence
<220> FEATURE:
<223> OTHER INFORMATION: Target specific primer
<220> FEATURE:
<221> NAME/KEY: misc_feature
<222> LOCATION: (25)..(27)
<223> OTHER INFORMATION: n is a, c, g, or t

<400> SEQUENCE: 10
ttcagacgtg tgctcttccg atctnnnggt gaaacctgtt tgttggacat ac           52

<210> SEQ ID NO 11
<211> LENGTH: 52
<212> TYPE: DNA
<213> ORGANISM: Artificial Sequence
<220> FEATURE:
<223> OTHER INFORMATION: Target specific primer
<220> FEATURE:
<221> NAME/KEY: misc_feature
<222> LOCATION: (25)..(27)
<223> OTHER INFORMATION: n is a, c, g, or t

<400> SEQUENCE: 11
ttcagacgtg tgctcttccg atctnnnttg ctggtgtgaa atgactgagt ac           52

<210> SEQ ID NO 12
<211> LENGTH: 46
<212> TYPE: DNA
<213> ORGANISM: Artificial Sequence
<220> FEATURE:
<223> OTHER INFORMATION: Target specific primer
<220> FEATURE:
<221> NAME/KEY: misc_feature
<222> LOCATION: (25)..(27)
<223> OTHER INFORMATION: n is a, c, g, or t

<400> SEQUENCE: 12
ttcagacgtg tgctcttccg atctnnncaa tccctgcccc ggttca                  46

<210> SEQ ID NO 13
<211> LENGTH: 55
```

```
<212> TYPE: DNA
<213> ORGANISM: Artificial Sequence
<220> FEATURE:
<223> OTHER INFORMATION: Target specific primer
<220> FEATURE:
<221> NAME/KEY: misc_feature
<222> LOCATION: (25)..(27)
<223> OTHER INFORMATION: n is a, c, g, or t

<400> SEQUENCE: 13
ttcagacgtg tgctcttccg atctnnntca gttaattttg gttacatccc tctct    55

<210> SEQ ID NO 14
<211> LENGTH: 55
<212> TYPE: DNA
<213> ORGANISM: Artificial Sequence
<220> FEATURE:
<223> OTHER INFORMATION: Target specific primer
<220> FEATURE:
<221> NAME/KEY: misc_feature
<222> LOCATION: (25)..(27)
<223> OTHER INFORMATION: n is a, c, g, or t

<400> SEQUENCE: 14
ttcagacgtg tgctcttccg atctnnntct ggtagaacag ttcttcactg aaaat    55

<210> SEQ ID NO 15
<211> LENGTH: 48
<212> TYPE: DNA
<213> ORGANISM: Artificial Sequence
<220> FEATURE:
<223> OTHER INFORMATION: Target specific primer
<220> FEATURE:
<221> NAME/KEY: misc_feature
<222> LOCATION: (25)..(27)
<223> OTHER INFORMATION: n is a, c, g, or t

<400> SEQUENCE: 15
ttcagacgtg tgctcttccg atctnnntca ggattgcctt taccactc    48

<210> SEQ ID NO 16
<211> LENGTH: 50
<212> TYPE: DNA
<213> ORGANISM: Artificial Sequence
<220> FEATURE:
<223> OTHER INFORMATION: Target specific primer
<220> FEATURE:
<221> NAME/KEY: misc_feature
<222> LOCATION: (25)..(27)
<223> OTHER INFORMATION: n is a, c, g, or t

<400> SEQUENCE: 16
ttcagacgtg tgctcttccg atctnnngaa ctttaccaca ctgctgaacc    50

<210> SEQ ID NO 17
<211> LENGTH: 55
<212> TYPE: DNA
<213> ORGANISM: Artificial Sequence
<220> FEATURE:
<223> OTHER INFORMATION: Target specific primer
<220> FEATURE:
<221> NAME/KEY: misc_feature
<222> LOCATION: (25)..(27)
<223> OTHER INFORMATION: n is a, c, g, or t

<400> SEQUENCE: 17
ttcagacgtg tgctcttccg atctnnnact tacctgtgac tccatagaaa atctt    55

<210> SEQ ID NO 18
```

-continued

```
<211> LENGTH: 53
<212> TYPE: DNA
<213> ORGANISM: Artificial Sequence
<220> FEATURE:
<223> OTHER INFORMATION: Target specific primer
<220> FEATURE:
<221> NAME/KEY: misc_feature
<222> LOCATION: (25)..(27)
<223> OTHER INFORMATION: n is a, c, g, or t

<400> SEQUENCE: 18
ttcagacgtg tgctcttccg atctnnntgg aagatccaat ccattttttgt tgt        53

<210> SEQ ID NO 19
<211> LENGTH: 55
<212> TYPE: DNA
<213> ORGANISM: Artificial Sequence
<220> FEATURE:
<223> OTHER INFORMATION: Target specific primer
<220> FEATURE:
<221> NAME/KEY: misc_feature
<222> LOCATION: (25)..(27)
<223> OTHER INFORMATION: n is a, c, g, or t

<400> SEQUENCE: 19
ttcagacgtg tgctcttccg atctnnncgt cttagtgtaa tactgtagtg gtcat      55

<210> SEQ ID NO 20
<211> LENGTH: 55
<212> TYPE: DNA
<213> ORGANISM: Artificial Sequence
<220> FEATURE:
<223> OTHER INFORMATION: Target specific primer
<220> FEATURE:
<221> NAME/KEY: misc_feature
<222> LOCATION: (25)..(27)
<223> OTHER INFORMATION: n is a, c, g, or t

<400> SEQUENCE: 20
ttcagacgtg tgctcttccg atctnnngac tctatcttca ttatttggga gctta      55

<210> SEQ ID NO 21
<211> LENGTH: 48
<212> TYPE: DNA
<213> ORGANISM: Artificial Sequence
<220> FEATURE:
<223> OTHER INFORMATION: Target specific primer
<220> FEATURE:
<221> NAME/KEY: misc_feature
<222> LOCATION: (25)..(27)
<223> OTHER INFORMATION: n is a, c, g, or t

<400> SEQUENCE: 21
ttcagacgtg tgctcttccg atctnnncct gatgggcaga ttacagtg              48

<210> SEQ ID NO 22
<211> LENGTH: 49
<212> TYPE: DNA
<213> ORGANISM: Artificial Sequence
<220> FEATURE:
<223> OTHER INFORMATION: Target specific primer
<220> FEATURE:
<221> NAME/KEY: misc_feature
<222> LOCATION: (25)..(27)
<223> OTHER INFORMATION: n is a, c, g, or t

<400> SEQUENCE: 22
ttcagacgtg tgctcttccg atctnnnaga ggaatgcagc ttgtactgg             49
```

```
<210> SEQ ID NO 23
<211> LENGTH: 53
<212> TYPE: DNA
<213> ORGANISM: Artificial Sequence
<220> FEATURE:
<223> OTHER INFORMATION: Target specific primer
<220> FEATURE:
<221> NAME/KEY: misc_feature
<222> LOCATION: (25)..(27)
<223> OTHER INFORMATION: n is a, c, g, or t

<400> SEQUENCE: 23
ttcagacgtg tgctcttccg atctnnncat gtgtagaaag cagatttctc cat         53

<210> SEQ ID NO 24
<211> LENGTH: 46
<212> TYPE: DNA
<213> ORGANISM: Artificial Sequence
<220> FEATURE:
<223> OTHER INFORMATION: Target specific primer
<220> FEATURE:
<221> NAME/KEY: misc_feature
<222> LOCATION: (25)..(27)
<223> OTHER INFORMATION: n is a, c, g, or t

<400> SEQUENCE: 24
ttcagacgtg tgctcttccg atctnnngcc tagtccctgg ctggac                  46

<210> SEQ ID NO 25
<211> LENGTH: 53
<212> TYPE: DNA
<213> ORGANISM: Artificial Sequence
<220> FEATURE:
<223> OTHER INFORMATION: Target specific primer
<220> FEATURE:
<221> NAME/KEY: misc_feature
<222> LOCATION: (25)..(27)
<223> OTHER INFORMATION: n is a, c, g, or t

<400> SEQUENCE: 25
ttcagacgtg tgctcttccg atctnnngaa gaagatgtgg aaaagtccca atg          53

<210> SEQ ID NO 26
<211> LENGTH: 54
<212> TYPE: DNA
<213> ORGANISM: Artificial Sequence
<220> FEATURE:
<223> OTHER INFORMATION: Target specific primer
<220> FEATURE:
<221> NAME/KEY: misc_feature
<222> LOCATION: (25)..(27)
<223> OTHER INFORMATION: n is a, c, g, or t

<400> SEQUENCE: 26
ttcagacgtg tgctcttccg atctnnncac tacaactaca tgtgtaacag ttcc         54

<210> SEQ ID NO 27
<211> LENGTH: 48
<212> TYPE: DNA
<213> ORGANISM: Artificial Sequence
<220> FEATURE:
<223> OTHER INFORMATION: Target specific primer
<220> FEATURE:
<221> NAME/KEY: misc_feature
<222> LOCATION: (25)..(27)
<223> OTHER INFORMATION: n is a, c, g, or t

<400> SEQUENCE: 27
ttcagacgtg tgctcttccg atctnnncct cctcagcatc ttatccga                48
```

```
<210> SEQ ID NO 28
<211> LENGTH: 47
<212> TYPE: DNA
<213> ORGANISM: Artificial Sequence
<220> FEATURE:
<223> OTHER INFORMATION: Target specific primer
<220> FEATURE:
<221> NAME/KEY: misc_feature
<222> LOCATION: (25)..(27)
<223> OTHER INFORMATION: n is a, c, g, or t

<400> SEQUENCE: 28
ttcagacgtg tgctcttccg atctnnngac ccaggtccag atgaagc          47

<210> SEQ ID NO 29
<211> LENGTH: 46
<212> TYPE: DNA
<213> ORGANISM: Artificial Sequence
<220> FEATURE:
<223> OTHER INFORMATION: Target specific primer
<220> FEATURE:
<221> NAME/KEY: misc_feature
<222> LOCATION: (25)..(27)
<223> OTHER INFORMATION: n is a, c, g, or t

<400> SEQUENCE: 29
ttcagacgtg tgctcttccg atctnnnctg cacagcgtct ccgagt           46

<210> SEQ ID NO 30
<211> LENGTH: 48
<212> TYPE: DNA
<213> ORGANISM: Artificial Sequence
<220> FEATURE:
<223> OTHER INFORMATION: Target specific primer
<220> FEATURE:
<221> NAME/KEY: misc_feature
<222> LOCATION: (25)..(27)
<223> OTHER INFORMATION: n is a, c, g, or t

<400> SEQUENCE: 30
ttcagacgtg tgctcttccg atctnnnctt acgggaggga agtcaaag         48

<210> SEQ ID NO 31
<211> LENGTH: 49
<212> TYPE: DNA
<213> ORGANISM: Artificial Sequence
<220> FEATURE:
<223> OTHER INFORMATION: Target specific primer
<220> FEATURE:
<221> NAME/KEY: misc_feature
<222> LOCATION: (25)..(27)
<223> OTHER INFORMATION: n is a, c, g, or t

<400> SEQUENCE: 31
ttcagacgtg tgctcttccg atctnnntct tgtgttccc ggacatagt         49

<210> SEQ ID NO 32
<211> LENGTH: 50
<212> TYPE: DNA
<213> ORGANISM: Artificial Sequence
<220> FEATURE:
<223> OTHER INFORMATION: Target specific primer
<220> FEATURE:
<221> NAME/KEY: misc_feature
<222> LOCATION: (25)..(27)
<223> OTHER INFORMATION: n is a, c, g, or t

<400> SEQUENCE: 32
ttcagacgtg tgctcttccg atctnnntgt gagtggatgg gtaaaaccta       50
```

<210> SEQ ID NO 33
<211> LENGTH: 51
<212> TYPE: DNA
<213> ORGANISM: Artificial Sequence
<220> FEATURE:
<223> OTHER INFORMATION: Target specific primer
<220> FEATURE:
<221> NAME/KEY: misc_feature
<222> LOCATION: (25)..(27)
<223> OTHER INFORMATION: n is a, c, g, or t

<400> SEQUENCE: 33
ttcagacgtg tgctcttccg atctnnncag aaatgcatca agcttctgtt c    51

<210> SEQ ID NO 34
<211> LENGTH: 44
<212> TYPE: DNA
<213> ORGANISM: Artificial Sequence
<220> FEATURE:
<223> OTHER INFORMATION: Target specific primer
<220> FEATURE:
<221> NAME/KEY: misc_feature
<222> LOCATION: (25)..(27)
<223> OTHER INFORMATION: n is a, c, g, or t

<400> SEQUENCE: 34
ttcagacgtg tgctcttccg atctnnngca gagcgtcaca gccg    44

<210> SEQ ID NO 35
<211> LENGTH: 49
<212> TYPE: DNA
<213> ORGANISM: Artificial Sequence
<220> FEATURE:
<223> OTHER INFORMATION: Target specific primer
<220> FEATURE:
<221> NAME/KEY: misc_feature
<222> LOCATION: (25)..(27)
<223> OTHER INFORMATION: n is a, c, g, or t

<400> SEQUENCE: 35
ttcagacgtg tgctcttccg atctnnnttc tccctctgca gagttgtta    49

<210> SEQ ID NO 36
<211> LENGTH: 46
<212> TYPE: DNA
<213> ORGANISM: Artificial Sequence
<220> FEATURE:
<223> OTHER INFORMATION: Target specific primer
<220> FEATURE:
<221> NAME/KEY: misc_feature
<222> LOCATION: (25)..(27)
<223> OTHER INFORMATION: n is a, c, g, or t

<400> SEQUENCE: 36
ttcagacgtg tgctcttccg atctnnntga cactgctgga acttcg    46

<210> SEQ ID NO 37
<211> LENGTH: 49
<212> TYPE: DNA
<213> ORGANISM: Artificial Sequence
<220> FEATURE:
<223> OTHER INFORMATION: Target specific primer
<220> FEATURE:
<221> NAME/KEY: misc_feature
<222> LOCATION: (25)..(27)
<223> OTHER INFORMATION: n is a, c, g, or t -continued

<210> SEQ ID NO 37
<400> SEQUENCE: 37
ttcagacgtg tgctcttccg atctnnnggg accttacctt atacaccgt            49

<210> SEQ ID NO 38
<211> LENGTH: 48
<212> TYPE: DNA
<213> ORGANISM: Artificial Sequence
<220> FEATURE:
<223> OTHER INFORMATION: Target specific primer
<220> FEATURE:
<221> NAME/KEY: misc_feature
<222> LOCATION: (25)..(27)
<223> OTHER INFORMATION: n is a, c, g, or t

<400> SEQUENCE: 38
ttcagacgtg tgctcttccg atctnnncac agcaaagcag aaactcac              48

<210> SEQ ID NO 39
<211> LENGTH: 52
<212> TYPE: DNA
<213> ORGANISM: Artificial Sequence
<220> FEATURE:
<223> OTHER INFORMATION: Target specific primer
<220> FEATURE:
<221> NAME/KEY: misc_feature
<222> LOCATION: (25)..(27)
<223> OTHER INFORMATION: n is a, c, g, or t

<400> SEQUENCE: 39
ttcagacgtg tgctcttccg atctnnnctc cttctgcatg gtattctttc tc         52

<210> SEQ ID NO 40
<211> LENGTH: 52
<212> TYPE: DNA
<213> ORGANISM: Artificial Sequence
<220> FEATURE:
<223> OTHER INFORMATION: Target specific primer
<220> FEATURE:
<221> NAME/KEY: misc_feature
<222> LOCATION: (25)..(27)
<223> OTHER INFORMATION: n is a, c, g, or t

<400> SEQUENCE: 40
ttcagacgtg tgctcttccg atctnnnctt tacagatgaa aggactttgg ct         52

<210> SEQ ID NO 41
<211> LENGTH: 54
<212> TYPE: DNA
<213> ORGANISM: Artificial Sequence
<220> FEATURE:
<223> OTHER INFORMATION: Target specific primer
<220> FEATURE:
<221> NAME/KEY: misc_feature
<222> LOCATION: (25)..(27)
<223> OTHER INFORMATION: n is a, c, g, or t

<400> SEQUENCE: 41
ttcagacgtg tgctcttccg atctnnncgg tagtctacag attcatttga aacc       54

<210> SEQ ID NO 42
<211> LENGTH: 50
<212> TYPE: DNA
<213> ORGANISM: Artificial Sequence
<220> FEATURE:
<223> OTHER INFORMATION: Target specific primer
<220> FEATURE:
<221> NAME/KEY: misc_feature
<222> LOCATION: (25)..(27)

<223> OTHER INFORMATION: n is a, c, g, or t

<400> SEQUENCE: 42
ttcagacgtg tgctcttccg atctnnnctt gccatcattg tccaacaaag                50

<210> SEQ ID NO 43
<211> LENGTH: 60
<212> TYPE: DNA
<213> ORGANISM: Artificial Sequence
<220> FEATURE:
<223> OTHER INFORMATION: Target specific primer
<220> FEATURE:
<221> NAME/KEY: misc_feature
<222> LOCATION: (25)..(27)
<223> OTHER INFORMATION: n is a, c, g, or t

<400> SEQUENCE: 43
ttcagacgtg tgctcttccg atctnnnctt tacttactac acctcagata tatttcttca    60

<210> SEQ ID NO 44
<211> LENGTH: 44
<212> TYPE: DNA
<213> ORGANISM: Artificial Sequence
<220> FEATURE:
<223> OTHER INFORMATION: Target specific primer
<220> FEATURE:
<221> NAME/KEY: misc_feature
<222> LOCATION: (25)..(27)
<223> OTHER INFORMATION: n is a, c, g, or t

<400> SEQUENCE: 44
ttcagacgtg tgctcttccg atctnnngct ggacgtgcgc gatg                     44

<210> SEQ ID NO 45
<211> LENGTH: 54
<212> TYPE: DNA
<213> ORGANISM: Artificial Sequence
<220> FEATURE:
<223> OTHER INFORMATION: Target specific primer
<220> FEATURE:
<221> NAME/KEY: misc_feature
<222> LOCATION: (25)..(27)
<223> OTHER INFORMATION: n is a, c, g, or t

<400> SEQUENCE: 45
ttcagacgtg tgctcttccg atctnnngag actcacaaga attttctcca gtac           54

<210> SEQ ID NO 46
<211> LENGTH: 53
<212> TYPE: DNA
<213> ORGANISM: Artificial Sequence
<220> FEATURE:
<223> OTHER INFORMATION: Target specific primer
<220> FEATURE:
<221> NAME/KEY: misc_feature
<222> LOCATION: (25)..(27)
<223> OTHER INFORMATION: n is a, c, g, or t

<400> SEQUENCE: 46
ttcagacgtg tgctcttccg atctnnncgt ttgcatcact aacactacta tca            53

<210> SEQ ID NO 47
<211> LENGTH: 53
<212> TYPE: DNA
<213> ORGANISM: Artificial Sequence
<220> FEATURE:
<223> OTHER INFORMATION: Target specific primer
<220> FEATURE:
<221> NAME/KEY: misc_feature

```
<222> LOCATION: (25)..(27)
<223> OTHER INFORMATION: n is a, c, g, or t

<400> SEQUENCE: 47
ttcagacgtg tgctcttccg atctnnncat atcatagacc ttggtagcag tct         53

<210> SEQ ID NO 48
<211> LENGTH: 57
<212> TYPE: DNA
<213> ORGANISM: Artificial Sequence
<220> FEATURE:
<223> OTHER INFORMATION: Target specific primer
<220> FEATURE:
<221> NAME/KEY: misc_feature
<222> LOCATION: (25)..(27)
<223> OTHER INFORMATION: n is a, c, g, or t

<400> SEQUENCE: 48
ttcagacgtg tgctcttccg atctnnnagc aagaagttat ggaattcctt ttattga     57

<210> SEQ ID NO 49
<211> LENGTH: 54
<212> TYPE: DNA
<213> ORGANISM: Artificial Sequence
<220> FEATURE:
<223> OTHER INFORMATION: Target specific primer
<220> FEATURE:
<221> NAME/KEY: misc_feature
<222> LOCATION: (25)..(27)
<223> OTHER INFORMATION: n is a, c, g, or t

<400> SEQUENCE: 49
ttcagacgtg tgctcttccg atctnnntct gaagatgtac ctatggtcct agta        54

<210> SEQ ID NO 50
<211> LENGTH: 53
<212> TYPE: DNA
<213> ORGANISM: Artificial Sequence
<220> FEATURE:
<223> OTHER INFORMATION: Target specific primer
<220> FEATURE:
<221> NAME/KEY: misc_feature
<222> LOCATION: (25)..(27)
<223> OTHER INFORMATION: n is a, c, g, or t

<400> SEQUENCE: 50
ttcagacgtg tgctcttccg atctnnngag aaacctgtct cttggatatt ctc         53

<210> SEQ ID NO 51
<211> LENGTH: 56
<212> TYPE: DNA
<213> ORGANISM: Artificial Sequence
<220> FEATURE:
<223> OTHER INFORMATION: Target specific primer
<220> FEATURE:
<221> NAME/KEY: misc_feature
<222> LOCATION: (25)..(27)
<223> OTHER INFORMATION: n is a, c, g, or t

<400> SEQUENCE: 51
ttcagacgtg tgctcttccg atctnnntga ctgaatataa acttgtggta gttgga      56

<210> SEQ ID NO 52
<211> LENGTH: 45
<212> TYPE: DNA
<213> ORGANISM: Artificial Sequence
<220> FEATURE:
<223> OTHER INFORMATION: Target specific primer
<220> FEATURE:
```

```
<221> NAME/KEY: misc_feature
<222> LOCATION: (25)..(27)
<223> OTHER INFORMATION: n is a, c, g, or t

<400> SEQUENCE: 52
ttcagacgtg tgctcttccg atctnnntag agtgtgcgtg gctct            45

<210> SEQ ID NO 53
<211> LENGTH: 49
<212> TYPE: DNA
<213> ORGANISM: Artificial Sequence
<220> FEATURE:
<223> OTHER INFORMATION: Target specific primer
<220> FEATURE:
<221> NAME/KEY: misc_feature
<222> LOCATION: (25)..(27)
<223> OTHER INFORMATION: n is a, c, g, or t

<400> SEQUENCE: 53
ttcagacgtg tgctcttccg atctnnncca caaaatcgtg tcctggtag        49

<210> SEQ ID NO 54
<211> LENGTH: 47
<212> TYPE: DNA
<213> ORGANISM: Artificial Sequence
<220> FEATURE:
<223> OTHER INFORMATION: Target specific primer
<220> FEATURE:
<221> NAME/KEY: misc_feature
<222> LOCATION: (25)..(27)
<223> OTHER INFORMATION: n is a, c, g, or t

<400> SEQUENCE: 54
ttcagacgtg tgctcttccg atctnnngct gtcacctctt ggttgtg          47

<210> SEQ ID NO 55
<211> LENGTH: 47
<212> TYPE: DNA
<213> ORGANISM: Artificial Sequence
<220> FEATURE:
<223> OTHER INFORMATION: Target specific primer
<220> FEATURE:
<221> NAME/KEY: misc_feature
<222> LOCATION: (25)..(27)
<223> OTHER INFORMATION: n is a, c, g, or t

<400> SEQUENCE: 55
ttcagacgtg tgctcttccg atctnnngtc tccgcatcgt gtacttc          47

<210> SEQ ID NO 56
<211> LENGTH: 53
<212> TYPE: DNA
<213> ORGANISM: Artificial Sequence
<220> FEATURE:
<223> OTHER INFORMATION: Target specific primer
<220> FEATURE:
<221> NAME/KEY: misc_feature
<222> LOCATION: (25)..(27)
<223> OTHER INFORMATION: n is a, c, g, or t

<400> SEQUENCE: 56
ttcagacgtg tgctcttccg atctnnngtc taagatttct tgttggctt tgg    53

<210> SEQ ID NO 57
<211> LENGTH: 47
<212> TYPE: DNA
<213> ORGANISM: Artificial Sequence
<220> FEATURE:
<223> OTHER INFORMATION: Target specific primer
```

-continued

```
<220> FEATURE:
<221> NAME/KEY: misc_feature
<222> LOCATION: (25)..(27)
<223> OTHER INFORMATION: n is a, c, g, or t

<400> SEQUENCE: 57
ttcagacgtg tgctcttccg atctnnncag aaggcgggag acatatg               47

<210> SEQ ID NO 58
<211> LENGTH: 50
<212> TYPE: DNA
<213> ORGANISM: Artificial Sequence
<220> FEATURE:
<223> OTHER INFORMATION: Target specific primer
<220> FEATURE:
<221> NAME/KEY: misc_feature
<222> LOCATION: (25)..(27)
<223> OTHER INFORMATION: n is a, c, g, or t

<400> SEQUENCE: 58
ttcagacgtg tgctcttccg atctnnnacc ataactccac acatcactct            50

<210> SEQ ID NO 59
<211> LENGTH: 46
<212> TYPE: DNA
<213> ORGANISM: Artificial Sequence
<220> FEATURE:
<223> OTHER INFORMATION: Target specific primer
<220> FEATURE:
<221> NAME/KEY: misc_feature
<222> LOCATION: (25)..(27)
<223> OTHER INFORMATION: n is a, c, g, or t

<400> SEQUENCE: 59
ttcagacgtg tgctcttccg atctnnncac ggtctgggaa gtgttt                46

<210> SEQ ID NO 60
<211> LENGTH: 52
<212> TYPE: DNA
<213> ORGANISM: Artificial Sequence
<220> FEATURE:
<223> OTHER INFORMATION: Target specific primer
<220> FEATURE:
<221> NAME/KEY: misc_feature
<222> LOCATION: (25)..(27)
<223> OTHER INFORMATION: n is a, c, g, or t

<400> SEQUENCE: 60
ttcagacgtg tgctcttccg atctnnngaa cttggtctca aagattccag aa         52

<210> SEQ ID NO 61
<211> LENGTH: 44
<212> TYPE: DNA
<213> ORGANISM: Artificial Sequence
<220> FEATURE:
<223> OTHER INFORMATION: Target specific primer
<220> FEATURE:
<221> NAME/KEY: misc_feature
<222> LOCATION: (25)..(27)
<223> OTHER INFORMATION: n is a, c, g, or t

<400> SEQUENCE: 61
ttcagacgtg tgctcttccg atctnnnact tgcggcgttc atcg                  44
```